United States Patent
Son et al.

(10) Patent No.: US 11,311,195 B2
(45) Date of Patent: *Apr. 26, 2022

(54) ELECTRONIC DEVICE, AND METHOD FOR ANALYZING FACE INFORMATION IN ELECTRONIC DEVICE

(71) Applicant: Samsung Electronics Co., Ltd., Suwon-si (KR)

(72) Inventors: Joo-Young Son, Yongin-si (KR); Jin-Ho Kim, Suwon-si (KR); Woo-Sung Kang, Hwaseong-si (KR); Yun-Jung Kim, Seongnam-si (KR); Hong-Il Kim, Yongin-si (KR); Jae-Won Son, Suwon-si (KR); Won-Suk Chang, Hwaseong-si (KR); In-Ho Choi, Hwaseong-si (KR); Dae-Young Hyun, Suwon-si (KR); Tae-Hwa Hong, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 69 days.

This patent is subject to a terminal disclaimer.

(21) Appl. No.: 16/848,489

(22) Filed: Apr. 14, 2020

(65) Prior Publication Data

US 2020/0242334 A1 Jul. 30, 2020

Related U.S. Application Data

(63) Continuation of application No. 14/928,402, filed on Oct. 30, 2015, now Pat. No. 10,664,686.

(30) Foreign Application Priority Data

Nov. 4, 2014 (KR) .................. 10-2014-0152239
Jun. 29, 2015 (KR) .................. 10-2015-0092549

(51) Int. Cl.
*A61B 5/00* (2006.01)
*G06K 9/00* (2006.01)
(Continued)

(52) U.S. Cl.
CPC .......... *A61B 5/0077* (2013.01); *A61B 5/1176* (2013.01); *A61B 5/442* (2013.01);
(Continued)

(58) Field of Classification Search
CPC .... G06K 9/6215; G06K 9/03; G06K 2209/01; G06F 16/24558
See application file for complete search history.

(56) References Cited

U.S. PATENT DOCUMENTS 6,571,003 B1   5/2003  Hillebrand et al.
8,345,114 B2   1/2013  Ciuc et al.
(Continued)

FOREIGN PATENT DOCUMENTS

CN    1355680 A    6/2002
CN    1795827 A    7/2006
(Continued)

OTHER PUBLICATIONS

Hiroyuki Nishiyama et al., "Design of a Cognitive User-Support System for Skin Progress Analysis Using a Smart Phone", Faculty of Sci. and Tech. Tokyo University of Science, Tokyo, Japan.
(Continued)

*Primary Examiner* — Pinalben Patel
(74) *Attorney, Agent, or Firm* — Jefferson IP Law, LLP

(57) ABSTRACT

A method for analyzing face information in an electronic device is provided. The method includes detecting at least one face region from an image that is being captured by a camera module, zooming in the at least one detected face
(Continued)

region, and analyzing the at least one detected and zoomed in face region according to at least one analysis item.

15 Claims, 53 Drawing Sheets

(51) Int. Cl.

| | | |
|---|---|---|
| G06F 3/01 | (2006.01) | |
| H04N 5/232 | (2006.01) | |
| G16H 15/00 | (2018.01) | |
| G16H 50/20 | (2018.01) | |
| A61B 5/1171 | (2016.01) | |
| G06T 7/90 | (2017.01) | |
| G16H 30/20 | (2018.01) | |
| G06F 1/16 | (2006.01) | |
| G06F 3/0488 | (2013.01) | |
| G16H 30/40 | (2018.01) | |
| G06F 3/04883 | (2022.01) | |

(52) U.S. Cl.
CPC ............ *A61B 5/444* (2013.01); *A61B 5/7275* (2013.01); *G06F 3/017* (2013.01); *G06K 9/0061* (2013.01); *G06K 9/00248* (2013.01); *G06K 9/00281* (2013.01); *G06T 7/90* (2017.01); *G16H 15/00* (2018.01); *G16H 30/20* (2018.01); *G16H 50/20* (2018.01); *H04N 5/23218* (2018.08); *H04N 5/23293* (2013.01); *H04N 5/23296* (2013.01); *A61B 5/443* (2013.01); *A61B 5/6898* (2013.01); *A61B 5/743* (2013.01); *A61B 2576/00* (2013.01); *A61B 2576/02* (2013.01); *G06F 1/1626* (2013.01); *G06F 3/04883* (2013.01); *G06T 2207/30201* (2013.01); *G16H 30/40* (2018.01)

(56) References Cited

U.S. PATENT DOCUMENTS

| | | | |
|---|---|---|---|
| 8,384,793 B2 | 2/2013 | Ciuc et al. | |
| 8,493,464 B2 | 7/2013 | Pien | |
| 8,681,241 B2 | 3/2014 | Ciuc et al. | |
| 8,902,326 B2 | 12/2014 | Ciuc et al. | |
| 9,007,480 B2 | 4/2015 | Ciuc et al. | |
| 10,664,686 B2 * | 5/2020 | Son ........................ | G16H 15/00 |
| 2003/0063801 A1 | 4/2003 | Rubinstenn et al. | |
| 2004/0028263 A1 | 2/2004 | Sakamoto | |
| 2004/0170337 A1 * | 9/2004 | Simon ..................... | G06T 11/00 |
| | | | 382/254 |
| 2006/0050933 A1 | 3/2006 | Adam et al. | |
| 2006/0092315 A1 | 5/2006 | Payonk et al. | |
| 2006/0229912 A1 | 10/2006 | Negishi et al. | |
| 2008/0294013 A1 | 11/2008 | Gobeyn et al. | |
| 2009/0028380 A1 | 1/2009 | Hillebrand et al. | |
| 2009/0136101 A1 | 5/2009 | Chhibber et al. | |
| 2009/0201365 A1 | 8/2009 | Fukuoka et al. | |
| 2009/0303342 A1 * | 12/2009 | Corcoran ................ | G06K 9/00 |
| | | | 348/222.1 |
| 2010/0026831 A1 | 2/2010 | Ciuc et al. | |
| 2010/0026832 A1 | 2/2010 | Ciuc et al. | |
| 2010/0026833 A1 | 2/2010 | Ciuc et al. | |
| 2010/0232704 A1 | 9/2010 | Thorn | |
| 2010/0239119 A1 * | 9/2010 | Bazakos ............ | G06K 9/00261 |
| | | | 382/103 |
| 2011/0043662 A1 | 2/2011 | Kim | |
| 2011/0311112 A1 | 12/2011 | Matsuyama et al. | |
| 2012/0133753 A1 | 5/2012 | Chang et al. | |
| 2012/0275668 A1 | 11/2012 | Chou et al. | |
| 2013/0123647 A1 | 5/2013 | Bhatnagar et al. | |
| 2013/0188073 A1 | 7/2013 | Ciuc et al. | |
| 2013/0194261 A1 | 8/2013 | Cummins et al. | |
| 2013/0229549 A1 | 9/2013 | Ciuc et al. | |
| 2014/0085233 A1 | 3/2014 | Sudo | |
| 2014/0119642 A1 | 5/2014 | Lee et al. | |
| 2014/0192134 A1 | 7/2014 | Jung et al. | |
| 2014/0313303 A1 | 10/2014 | Davis et al. | |
| 2015/0297129 A1 * | 10/2015 | Gilbert ................... | A61B 5/411 |
| | | | 600/306 |
| 2016/0331308 A1 | 11/2016 | Zhou | |
| 2017/0061609 A1 * | 3/2017 | Son ..................... | G06Q 30/0641 |
| 2019/0340774 A1 * | 11/2019 | Patwardhan ........... | A61B 5/442 |
| 2021/0289128 A1 * | 9/2021 | Dong ................. | G06K 9/00255 |

FOREIGN PATENT DOCUMENTS

| | | |
|---|---|---|
| CN | 1866010 A | 11/2006 |
| CN | 1961820 A | 5/2007 |
| CN | 101027678 A | 8/2007 |
| CN | 101083940 A | 12/2007 |
| CN | 101170945 A | 4/2008 |
| CN | 101755288 A | 6/2010 |
| CN | 101996044 A | 3/2011 |
| CN | 102036607 A | 4/2011 |
| CN | 102782727 A | 11/2012 |
| CN | 103164615 A | 6/2013 |
| CN | 103340604 A | 10/2013 |
| CN | 103634551 A | 3/2014 |
| CN | 104063464 A | 9/2014 |
| FR | 2952519 A1 | 5/2011 |
| JP | 2004-157771 A | 6/2004 |
| JP | 2007-133518 A | 5/2007 |
| JP | 2011-090258 A | 5/2011 |
| KR | 10-2009-0067914 A | 6/2009 |
| KR | 10-2014-0070906 A | 6/2014 |
| KR | 10-1417811 B1 | 7/2014 |
| WO | 0076398 A1 | 12/2000 |

OTHER PUBLICATIONS

Chinese Office Action dated Mar. 4, 2020, issued in Chinese Application No. 201510736495.9.

Chinese Office Action dated Oct. 9, 2020, issued in Chinese Application No. 201510736495.9.

KIPO Office Action dated Oct. 8, 2021, issued in Korean Application No. 10-2015-0092549.

* cited by examiner

ELECTRONIC DEVICE, AND METHOD FOR ANALYZING FACE INFORMATION IN ELECTRONIC DEVICE

CROSS-REFERENCE TO RELATED APPLICATION(S)

This application is a continuation application of prior application Ser. No. 14/928,402, filed on Oct. 30, 2015, which was based on and claimed priority under 35 U.S.C. § 119(a) of a Korean patent application filed on Nov. 4, 2014 in the Korean Intellectual Property Office and assigned Serial number 10-2014-0152239, and of a Korean patent application filed on Jun. 29, 2015 in the Korean Intellectual Property Office and assigned Serial number 10-2015-0092549, the entire disclosure of each of which is hereby incorporated by reference.

TECHNICAL FIELD

The present disclosure relates to an electronic device, and a method for analyzing face information in the electronic device. More particularly, the present disclosure relates to a method for analyzing face information in the electronic device, in which once face information (e.g., a face region) is identified, the identified region may be zoomed in or the focus may be automatically set on the region during capturing, without any user's control action.

BACKGROUND

A variety of electronic devices have been developed to provide various functions. For example, an electronic device (e.g., a smart phone) has been designed to provide not only a function of capturing images, but also a function of recognizing the captured objects.

The electronic device may be provided with a display so that the user may more effectively use or enjoy the various functions. For example, the recent smart phone may be provided with a display (e.g., a touch screen), the front of which is sensitive to a touch.

Various applications (or Apps) may be installed and run in the electronic device. In order to run and control the applications in the electronic device, various input units (e.g., a touch screen, a button, a mouse, a keyboard, a sensor, and the like.) may be used.

In order to analyze an object (e.g., a face region) being captured, the electronic device may obtain an image, the object in which is zoomed in or finely captured. On the other hand, in order to obtain the zoomed in or finely captured image, the user may determine or identify an object to be captured and determine whether the focus is set on a detailed region of each object, thereby enabling the shooting function (or capturing function) of the electronic device.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect the present disclosure is to provide an electronic device and a method for analyzing face information in the electronic device, in which once face information (e.g., a face region) is identified, the identified region may be zoomed in or the focus may be automatically set on the region during capturing, without any user's control action.

In accordance with an aspect of the present disclosure, a method for analyzing face information in an electronic device is provided. The method includes detecting at least one face region from an image that is being captured by a camera module, zooming in the at least one detected face region, and analyzing the zoomed in face region according to at least one analysis item.

In accordance with another aspect of the present disclosure, an electronic device is provided. The electronic device includes a camera module, a display configured to display an image that is being captured by the camera module, and a controller configured to detect at least one face region from the image, control the camera module to zoom in the at least one detected face region, and analyze the at least one detected and zoomed in face region according to at least one analysis item.

In accordance with another aspect of the present disclosure, a method for analyzing face information in an electronic device is provided. The method includes detecting at least one face region from at least one stored image and analyzing the at least one detected face region according to at least one analysis item.

In accordance with another aspect of the present disclosure, an electronic device is provided. The electronic device includes a camera module configured to capture an image and a controller configured to detect at least one face region from at least one image that is captured by the camera module and stored, and analyze the at least one detected face region according to at least one analysis item.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, like reference numerals will be understood to refer to like parts, components, and structures.

DETAILED DESCRIPTION

Figure 1:
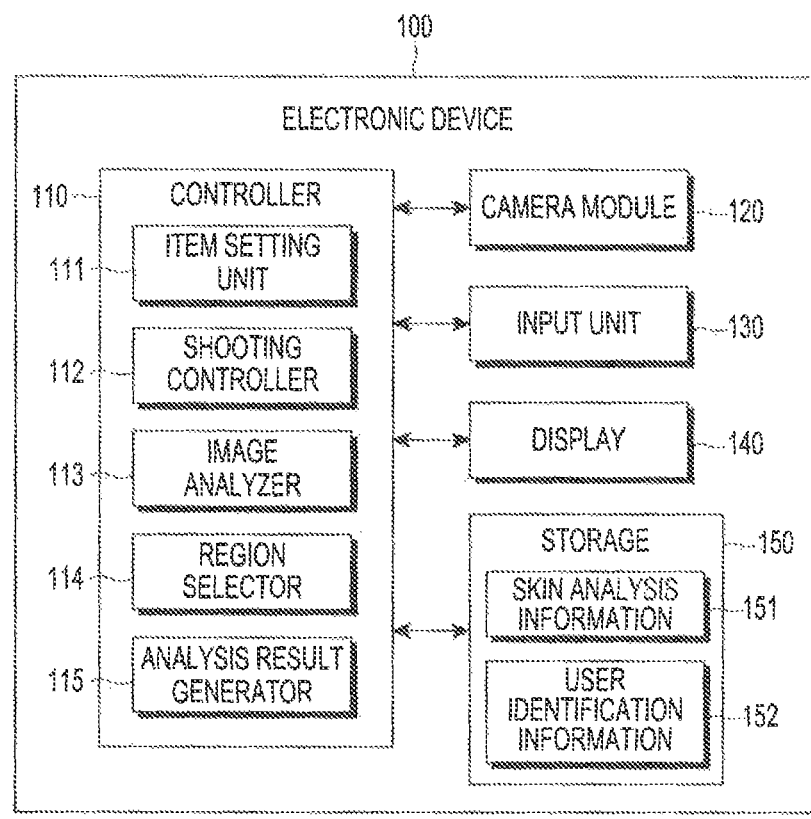
FIG. 1 is a block diagram illustrating a configuration of an electronic device according to various embodiments of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

The terms "comprise" and/or "comprising" as herein used specify the presence of disclosed functions, operations, or components, but do not preclude the presence or addition of one or more other functions, operations, or components. It will be further understood that the terms "comprise" and/or "have," when used in this specification, specify the presence of stated features, integers, operations, elements, and/or components, but do not preclude the presence or addition of one or more other features, integers, operations, elements, components, and/or groups thereof.

As used herein, the term "A or B" or "at least one of A and/or B" includes any and all combinations of one or more of the associated listed items. For examples, "A or B" or "at least one of A or/and B" each may include A, or include B, or include both A and B.

Ordinal numbers as herein used, such as "first", "second", and the like, may modify various components of various embodiments of the present disclosure, but do not limit those components. For example, these terms do not limit the order and/or importance of the components. These terms are only used to distinguish one component from another. For example, a first user device and a second user device are different user devices from each other. For example, according to various embodiments of the present disclosure, a first component may be denoted a second component, and vice versa without departing from the scope of the present disclosure.

When a component is "connected to" or "coupled to" another component, the component may be directly connected or coupled to the other component, or other component(s) may intervene therebetween. In contrast, when a component is "directly connected to" or "directly coupled to" another component, no other intervening components may intervene therebetween.

The terms as used herein are provided merely to describe some embodiments thereof, but not to limit the present disclosure.

Unless otherwise defined, all terms including technical and scientific terms used herein have the same meaning as commonly understood by one of ordinary skill in the art to which the various embodiments of the present disclosure belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

An electronic device according to various embodiments of the present disclosure may be a camera module. For example, the electronic device may include at least one of a smart phone, a tablet personal computer (PC), a mobile phone, a video phone, an e-book reader, a desktop PC, a laptop PC, a netbook computer, a personal digital assistant (PDA), a portable multimedia player (PMP), a Moving Picture Experts Group phase 1 or phase 2 (MPEG-1 or MPEG-2) audio layer 3 (MP3) player, a mobile medical device, a camera, or a wearable device (e.g., a head-mounted-device (HMD), such as electronic glasses, electronic clothing, electronic bracelet, electronic necklace, electronic application accessory (or appcessory), electronic tattoo, a smart watch, and the like).

In various embodiments of the present disclosure, the electronic device may be a smart home appliance with a camera module. The smart home appliance may include at least one of, for example, a television (TV), a digital video disc (DVD) player, an audio player, a refrigerator, an air conditioner, a cleaner, an oven, a microwave oven, a washer, an air purifier, a set-top box, a TV box (e.g., Samsung HomeSync™, Apple TV™, or Google TV™), game consoles, an electronic dictionary, an electronic key, a camcorder, or an electronic photo frame.

In various embodiments of the present disclosure, the electronic device may include a camera module, and may further include at least one of various medical devices (e.g., magnetic resonance angiography (MRA), magnetic resonance imaging (MRI), computed tomography (CT), a camcorder, a ultrasonic device, and the like), a navigation device, a global positioning system (GPS) receiver, an event data recorder (EDR), a flight data recorder (FDR), an automotive infotainment device, a marine electronic device (e.g., a marine navigation device, a gyro compass, and the like), avionics, a security device, a car head unit, an industrial or household robot, an automatic teller's machine (ATM) for banks, point of sales (POS) for shops, and the like.

In various embodiments of the present disclosure, the electronic device may include at least one of a part of the furniture or building/structure, an electronic board, an electronic signature receiving device, a projector or various meters (e.g., a water meter, an electricity meter, a gas meter, a radio wave meter, and the like), each of which includes a camera module. The electronic device according to various embodiments of the present disclosure may be one or a combination of the above-described devices. Further, the electronic device according to various embodiments of the present disclosure may be a flexible device. It will be apparent to those skilled in the art that the electronic device according to various embodiments of the present disclosure is not limited to the above-described devices.

In accordance with various embodiments of the present disclosure, the face information that can be analyzed by the electronic device may include skin information of face regions, such as eyes, nose, brow, cheek, and the like.

In accordance with various embodiments of the present disclosure, the electronic device may analyze skin information according to at least one analysis item. For example, items for analyzing the face information may include items for measuring a variety of skin conditions, such as pores, acne, pigmentation, skin tone, dark circles, wrinkles, and the like.

In accordance with various embodiments of the present disclosure, an operation in which the electronic device performs fine shooting may include an operation in which in order to finely capture any one region in a specific image, the focus is set on the region and the region is zoomed in, during the capturing.

The electronic device according to various embodiments of the present disclosure will be described below with reference to the accompanying drawings. As used herein, the term 'user' may refer to a person who uses the electronic device, or a device (e.g., an intelligent electronic device) that uses the electronic device.

FIG. 1 is a block diagram illustrating a configuration of an electronic device according to various embodiments of the present disclosure.

Referring to FIG. 1, an electronic device 100 may include at least one of a controller 110, a camera module 120, an input unit 130, a display 140, or a storage 150.

The controller 110 may include at least one of an item setting unit 111, a shooting controller 112, an image analyzer 113, a region selector 114, or an analysis result generator 115, and may control the overall operation of the electronic device 100.

The item setting unit 111 may identify a specific face region in a captured image, and select at least one item for analyzing the skin conditions of the identified face region. For example, if a region around the eyes is identified in the captured image, the item setting unit 111 may set wrinkles, dark circles, and the like, as an item for analyzing the skin conditions of the region around the eyes. As another example, if a cheek region is identified in the captured image, the item setting unit 111 may set pigmentation, dots, freckles, skin tone, and the like, as an item for analyzing the skin conditions of the cheek region.

Upon identifying a specific face region in the shooting mode, the shooting controller 112 may control the camera module 120 so that the identified face region may be zoomed in or finely captured. For example, the shooting controller 112 may control the camera module 120 so as to set the focus on or zoom in at least one region identified as a face region during the capturing, in the captured image identified through the camera module 120.

The image analyzer 113 may select at least one item for analyzing a specific face region in the image, and analyze the face region according to the selected item. For example, the image analyzer 113 may analyze the region around the eyes, which is identified in the captured image, according to the selected item (e.g., wrinkles or dark circles). For example, the image analyzer 113 may analyze the depth or the number of wrinkles or the width or color of dark circles in the identified region around the eyes.

The region selector 114 may determine whether a face region is identified in a specific image. According to various embodiments of the present disclosure, if a specific face region is identified, the region selector 114 may control the camera module 120 so as to set the focus on or zoom in the face region during the capturing.

The analysis result generator 115 may determine a result of the face information analyzed by the image analyzer 113, generate a screen including the determined result, and display the generated screen.

According to various embodiments of the present disclosure, the analysis result generator 115 may represent the analysis item or analysis result for each face region in various ways, to generate a screen of the analyzed face information. For example, the analysis result generator 115 may generate a screen of the face information so that each analysis item may be displayed in a different color (for example, the acne may be displayed in red and the pigmentation may be displayed in blue). Further, by determining the previous analysis result, the analysis result generator 115 may display the improved face region in green or blue and the worsened face region in red, to generate a screen of the face information.

According to various embodiments of the present disclosure, if a region corresponding to a specific face region, or a region that is distinguished in a different color according to the analysis item or analysis result is selected from the captured image, the analysis result generator 115 may provide an image obtained by zooming in or analyzing the selected face region. For example, the analysis result generator 115 may control the display 140 so as to display the generated image.

The camera module 120 may capture an image. According to various embodiments of the present disclosure, the camera module 120 may be controlled by the controller 110 so as to set the focus on and zoom in a region identified as a specific face region, during the capturing.

The display 140 may display an image that is being captured by the camera module 120.

According to various embodiments of the present disclosure, if a specific region is selected from the displayed image, the display 140 may display an image obtained by zooming in or finely capturing the region. For example, as the electronic device 100 selects a specific region, the zoomed in image may be an image obtained by zooming in and capturing the selected region. As the electronic device 100 selects a specific region, the zoomed in image may be an image, in which the focus is set on the selected region and the selected region is zoomed in, during the capturing.

The storage 150 may include skin analysis information 151 or user identification information 152. The skin analysis information 151 may include skin analysis information of a specific face region according to the analysis item.

The skin analysis information 151 may include information obtained by analyzing the skin conditions of a specific region for each item. For example, the skin analysis information 151 may include information obtained by determining the presence/absence of pigmentation, skin tone, dots or acne in a specific face region, the previously analyzed information for each item, or history information that shows the skin analysis result for each face region in a time sequence.

The user identification information 152 may include face information for a specific user. For example, the image analyzer 113 may compare an 'eye' region identified in the captured image with the previously stored 'eye' image of another user, using the user identification information 152. As for user identification information 152, based on the comparison result in the image analyzer 113, the analysis result for the face region identified in the captured image may be stored in the face information about the user including the same face region.

For example, an electronic device according to various embodiments of the present disclosure may include a camera module, a display configured to display an image that is being captured by the camera module, and a controller configured to detect at least one face region from the image, control the camera module to zoom in the at least one detected face region, and analyze the zoomed in face region according to at least one analysis item.

The at least one face region according to various embodiments of the present disclosure may include a region around at least one of eyes, nose, cheeks, mouth or brow.

The at least one analysis item according to various embodiments of the present disclosure may include at least one of wrinkles, acne, pigmentation, skin tone, dark circles or pores.

The controller according to various embodiments of the present disclosure may analyze at least one of thickness, size, number, width or color for each analysis item in the zoomed in face region.

Upon detecting an input of a gesture for a specific region in the image, the controller according to various embodiments of the present disclosure may control the display to display an image obtained by zooming in a region where the gesture is detected.

The controller according to various embodiments of the present disclosure may detect a face region for at least one predetermined analysis item from the image, and analyze the detected face region according to the predetermined analysis item.

Upon detecting the at least one face region, the controller according to various embodiments of the present disclosure may control the display to display a screen for the zoomed in face region.

The controller according to various embodiments of the present disclosure may control the camera module to finely capture the at least one detected face region upon detecting a predetermined action.

The predetermined action according to various embodiments of the present disclosure may include any one of an action of running an application in which the camera module is enabled, an action of enabling the electronic device 100 in a locked state, or an action of positioning the electronic device 100 at a specific angle or in a specific direction.

The controller according to various embodiments of the present disclosure may determine a pre-stored analysis result for a specific face region or analysis item, compare the determined pre-stored analysis result with a result of the analysis, and control the display to display a screen including a result of the comparison.

Figure 2:
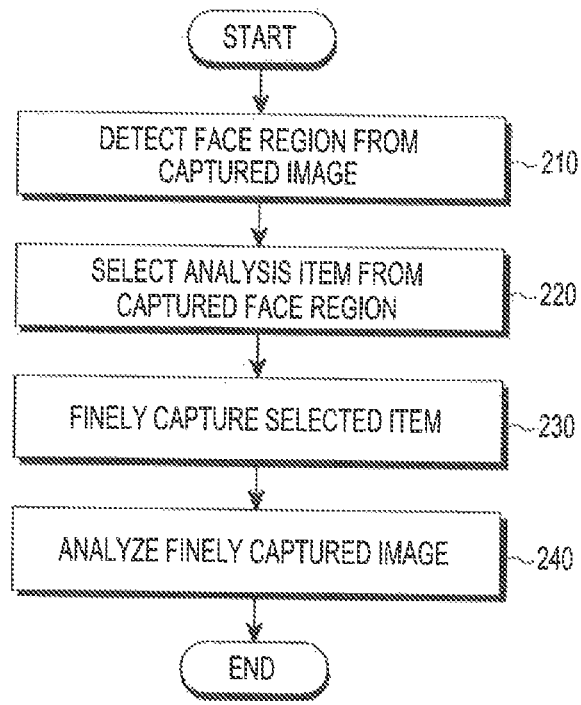
FIGS. 2, 3, and 4 are flowcharts illustrating an operation of analyzing skin information in an electronic device according to various embodiments of the present disclosure.

FIG. 2 is a flowchart illustrating an operation of analyzing skin information in an electronic device according to various embodiments of the present disclosure.

Referring to FIG. 2, in operation 210, the electronic device may detect a face region from a captured image.

In operation 220, the electronic device may select an analysis item from the captured face region.

In operation 230, the electronic device may finely capture the selected item. For example, the electronic device may set the focus on and zoom in the selected item during the capturing.

In operation 240, the electronic device may analyze the zoomed in image. According to various embodiments of the present disclosure, the electronic device may compare the zoomed in image with the previously stored result value. For example, the electronic device may compare the zoomed in image with the previously stored result value to analyze the face region corresponding to the zoomed in image.

According to various embodiments of the present disclosure, if the user captures an image including a face region, the captured output image may include an image obtained by zooming in or finely capturing each face region included in the captured image, or an image including a result of analyzing the zoomed in or finely captured image. For example, by capturing a face region, the user may obtain an image obtained by zooming in or finely capturing each face region and a result of analyzing the zoomed in or finely captured image, without taking any additional action for face analysis.

At least one of operations 210 to 240 shown in FIG. 2 may be omitted, or at least one other operation may be added in between operations 210 to 240. Further, operations 210 to 240 in FIG. 2 may be performed in the depicted order, or at least one of operations 210 to 240 may be changed in execution order.

For example, a method for analyzing face information in an electronic device according to various embodiments of the present disclosure may include detecting at least one face region from an image that is being captured by a camera module, zooming in the at least one detected face region, and analyzing the zoomed in face region according to at least one analysis item. The at least one face region may include a region around at least one of eyes, nose, cheeks, mouth or brow. The at least one analysis item may include at least one of wrinkles, acne, pigmentation, skin tone, dark circles or pores.

The analyzing according to various embodiments of the present disclosure may include analyzing at least one of thickness, size, number, width or color for each analysis item in the zoomed in face region.

The method according to various embodiments of the present disclosure may further include, upon detecting an input of a gesture for a specific region in the image, displaying an image obtained by zooming in a region where the gesture is detected.

The method according to various embodiments of the present disclosure may further include detecting a face region for at least one predetermined analysis item from the image, and analyzing the detected face region according to the predetermined analysis item.

The method according to various embodiments of the present disclosure may further include, upon detecting the at least one face region, displaying a screen obtained by zooming in the detected face region.

The method according to various embodiments of the present disclosure may further include zooming in the at least one detected face region upon detecting a predetermined action. The predetermined action may include any one of an action of running an application in which the camera module is enabled, an action of enabling the electronic device in a locked state, and an action of positioning the electronic device at a specific angle or in a specific direction.

The method according to various embodiments of the present disclosure may further include determining a pre-stored analysis result for a specific face region or analysis item, and comparing the determined pre-stored analysis result with a result of the analysis, and displaying a result of the comparison.

Figure 3:
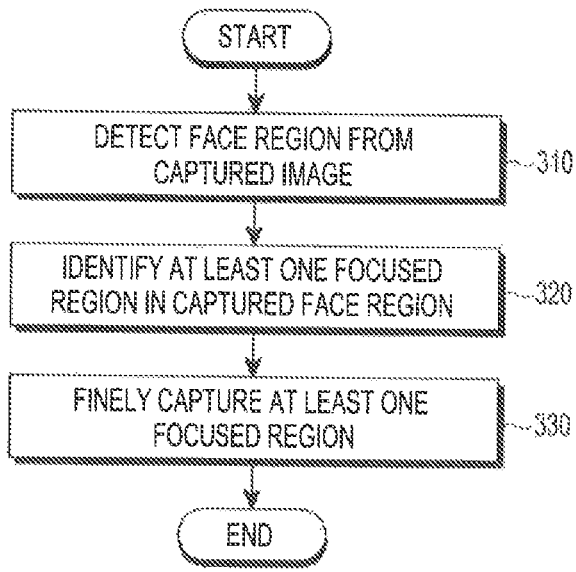

FIG. 3 is a flowchart illustrating an operation of analyzing skin information in an electronic device according to various embodiments of the present disclosure.

Referring to FIG. 3, in operation 310, the electronic device may detect a face region from a captured image.

In operation 320, the electronic device may identify at least one focused region in the captured face region.

In operation 330, the electronic device may zoom in or finely capture the at least one focused region. For example, as the focused region is zoomed in or finely captured, the output image may be an image obtained by setting the focus on and/or zooming in a specific region during the capturing.

Although the electronic device has performed an operation of identifying at least one focused region in operation 320 according to various embodiments of the present disclosure, the electronic device may zoom in or finely capture a detected face region, upon detecting the face region from the image that is captured in operation 310. In this case, operation 320 may be omitted.

At least one of operations 310 to 330 shown in FIG. 3 may be omitted, or at least one other operation may be added in between operations 310 to 330. Further, operations 310 to 330 in FIG. 3 may be performed in the depicted order, or at least one of operations 310 to 330 may be changed in execution order.

Figure 4:
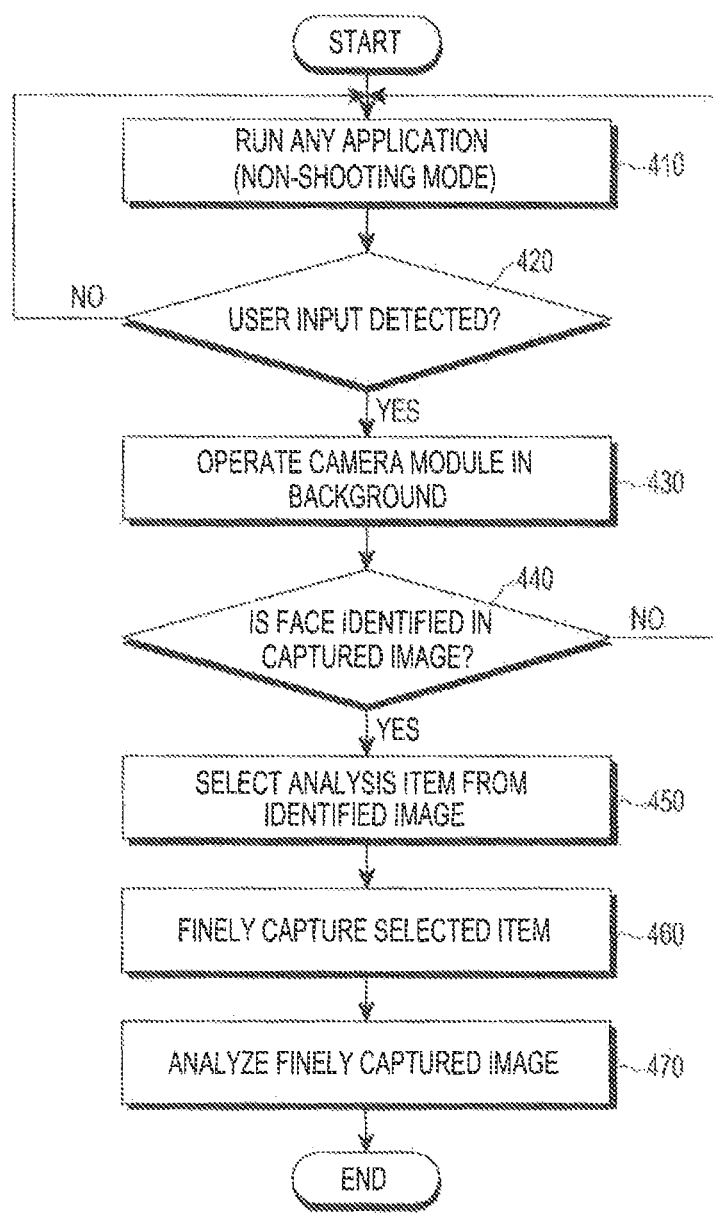

FIG. 4 is a flowchart illustrating an operation of analyzing skin information in an electronic device according to various embodiments of the present disclosure.

Referring to FIG. 4, in operation 410, the electronic device may determine whether any application is run, in the non-shooting mode.

In operation 420, the electronic device may determine whether a predetermined user input is detected.

If it is determined that the predetermined user input is not detected, the electronic device may perform again operation 410.

If it is determined that the predetermined user input is detected, the electronic device may control the camera module to operate in the background, in operation 430.

In operation 440, the electronic device may determine whether a face region is identified in the captured image.

If it is determined that the face region is not identified, the electronic device may perform again operation 410.

If it is determined that the face region is identified, the electronic device may select at least one analysis item for the identified image in operation 450. For example, the least one analysis item in the image may include at least one of the items for measuring various skin conditions, such as pores, acne, pigmentation, skin tone, dark circles, wrinkles, and the like.

In operation 460, the electronic device may control the camera module so as to zoom in or set focus on the selected item.

In operation 470, the electronic device may analyze the zoomed in image.

At least one of operations 410 to 470 shown in FIG. 4 may be omitted, or at least one other operation may be added in between operations 410 to 470. Further, operations 410 to 470 in FIG. 4 may be performed in the depicted order, or at least one of operations 410 to 470 may be changed in execution order.

FIGS. 5A, 5B, 5C, 5D, 5E, 5F, 5G, and 5H illustrate a face region and a situation in which the face region is partially zoomed in or finely captured according to various embodiments of the present disclosure.

Referring to FIGS. 5A, 5B, 5C, 5D, 5E, 5F, 5G, and 5H, according to various embodiments of the present disclosure, it is assumed that the electronic device is capturing or shooting the entire face. The electronic device may identify at least one face region in an image 500 that is being captured.

Figure 5A:
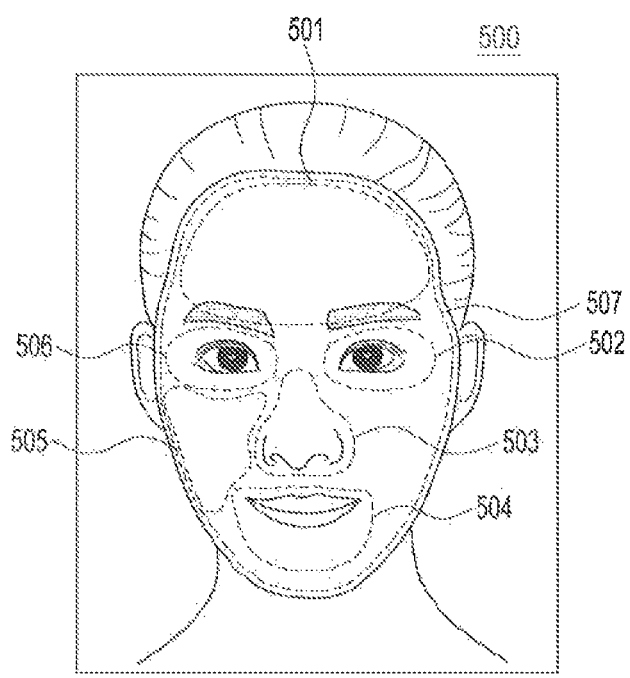
FIGS. 5A, 5B, 5C, 5D, 5E, 5F, 5G, and 5H illustrate a face region and a situation in which the face region is partially zoomed in or finely captured according to various embodiments of the present disclosure.

Referring to FIG. 5A, the electronic device may identify at least one of a brow 501, a right eye 502, a left eye 506, a nose 503, a mouth edge 504, a cheek 505 or a face 507 in the image 500 being captured.

According to various embodiments of the present disclosure, upon identifying at least one face region in the image 500 being captured, the electronic device may zoom in the region to capture an image obtained by partially zooming in or finely capturing the region.

Figure 5B:
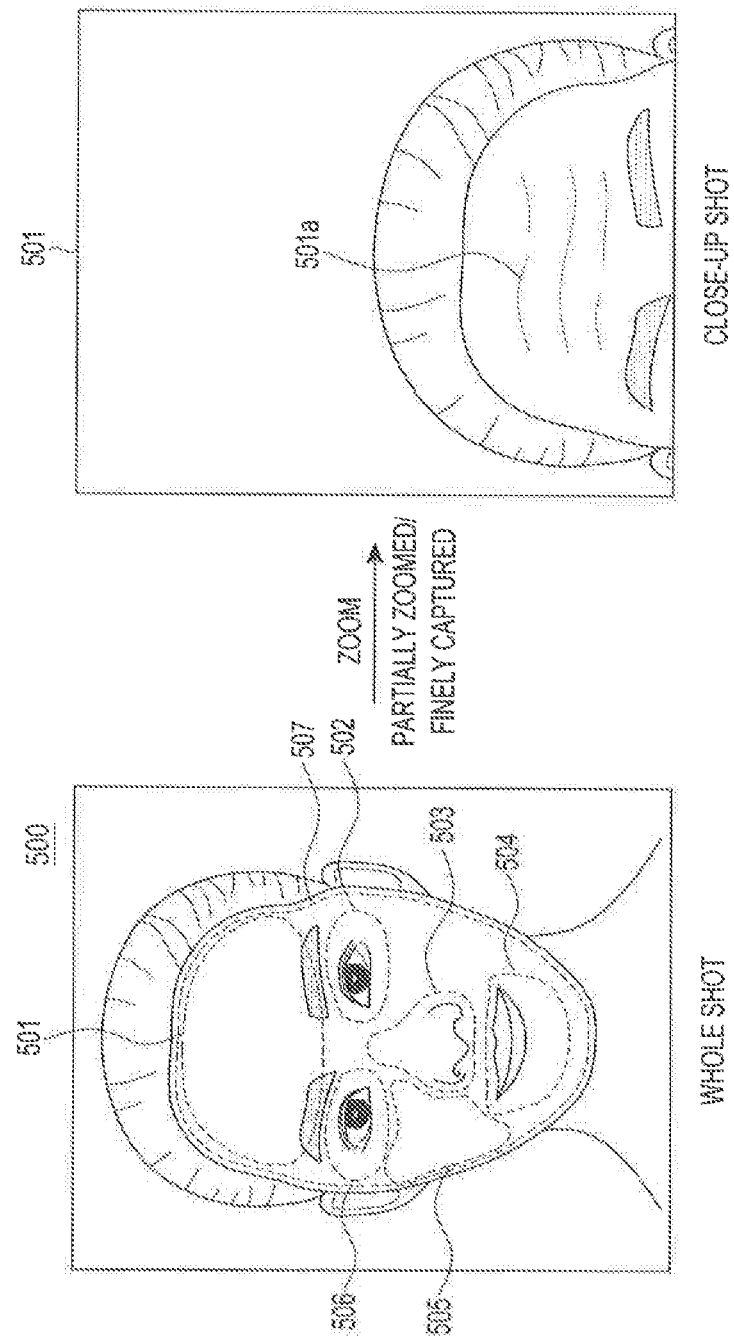

Referring to FIG. 5B, upon identifying the brow 501 in the image 500 being capture, the electronic device may zoom in a region of the brow 501 to partially zoom in or finely capture the region. The electronic device may obtain skin analysis information that is based on at least one analysis item, from the captured image obtained by partially zooming in the region of the brow 501. For example, the skin analysis information may include information about wrinkles 501a in the region of the brow 501.

Figure 5C:
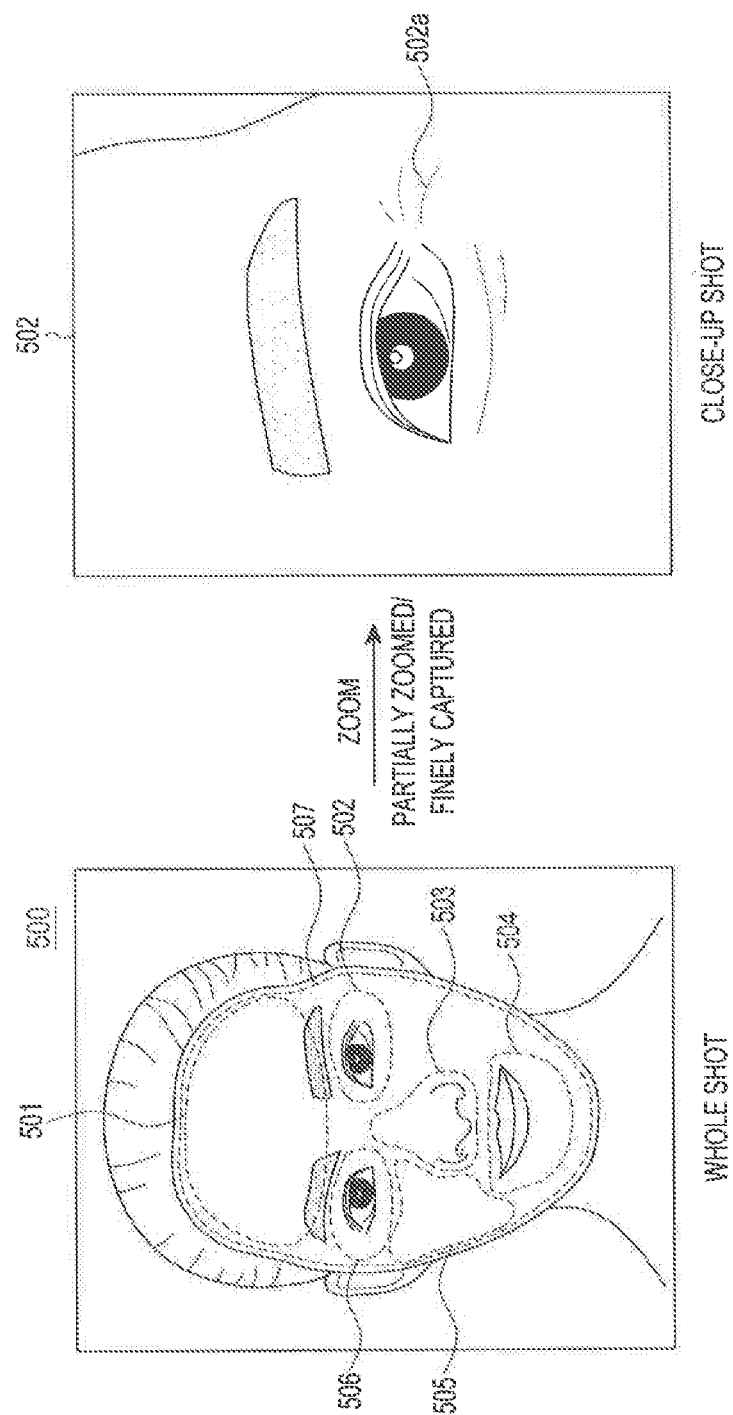

Referring to FIG. 5C, upon identifying the right eye 502 in the image 500 being captured, the electronic device may zoom in a region of the right eye 502 to partially zoom in or finely capture the region. The electronic device may obtain skin analysis information that is based on at least one analysis item, from the captured image obtained by partially zooming in the region of the right eye 502. For example, the skin analysis information may include information about wrinkles 502a in the region of the right eye 502.

Figure 5D:
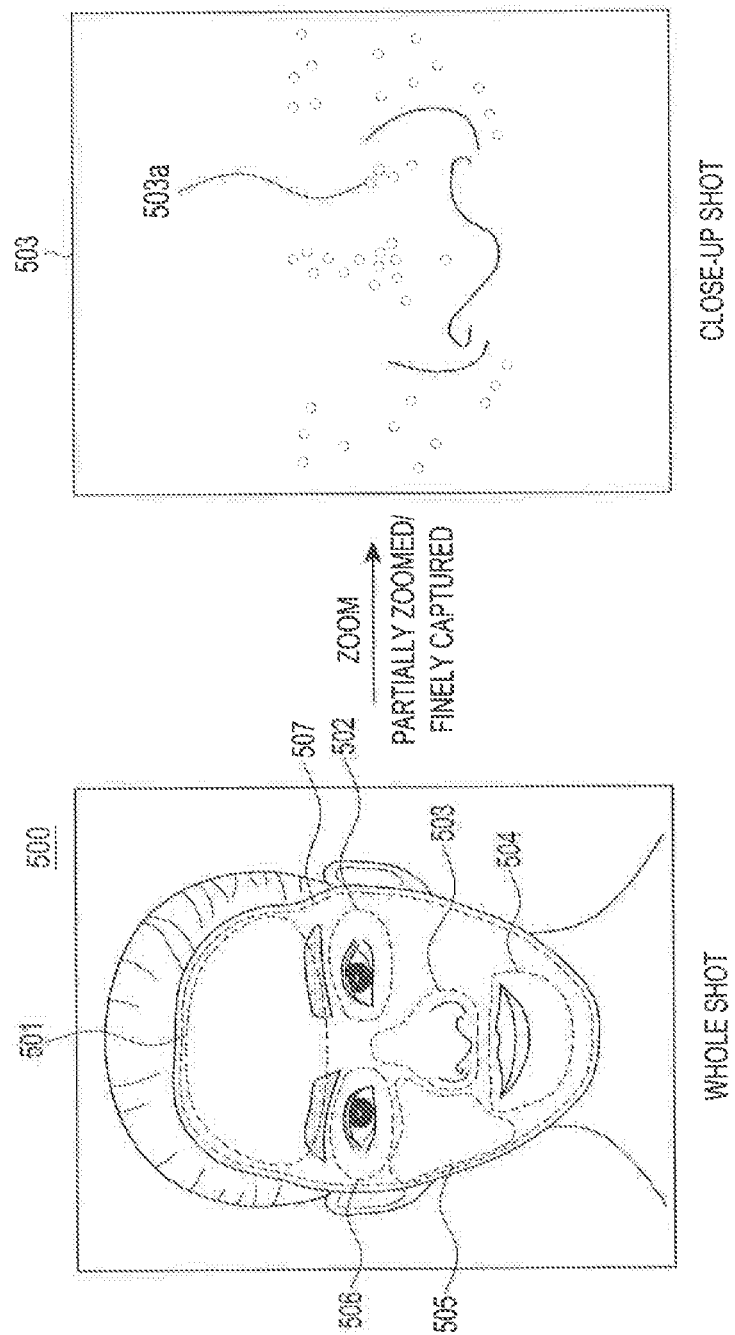

Referring to FIG. 5D, upon identifying the nose 503 in the image 500 being captured, the electronic device may zoom in a region of the nose 503 to partially zoom in or finely capture the region. The electronic device may obtain skin analysis information that is based on at least one analysis item, from the captured image obtained by partially zooming in the region of the nose 503. For example, the skin analysis information may include information about pores 503a in the region of the nose 503.

Figure 5E:
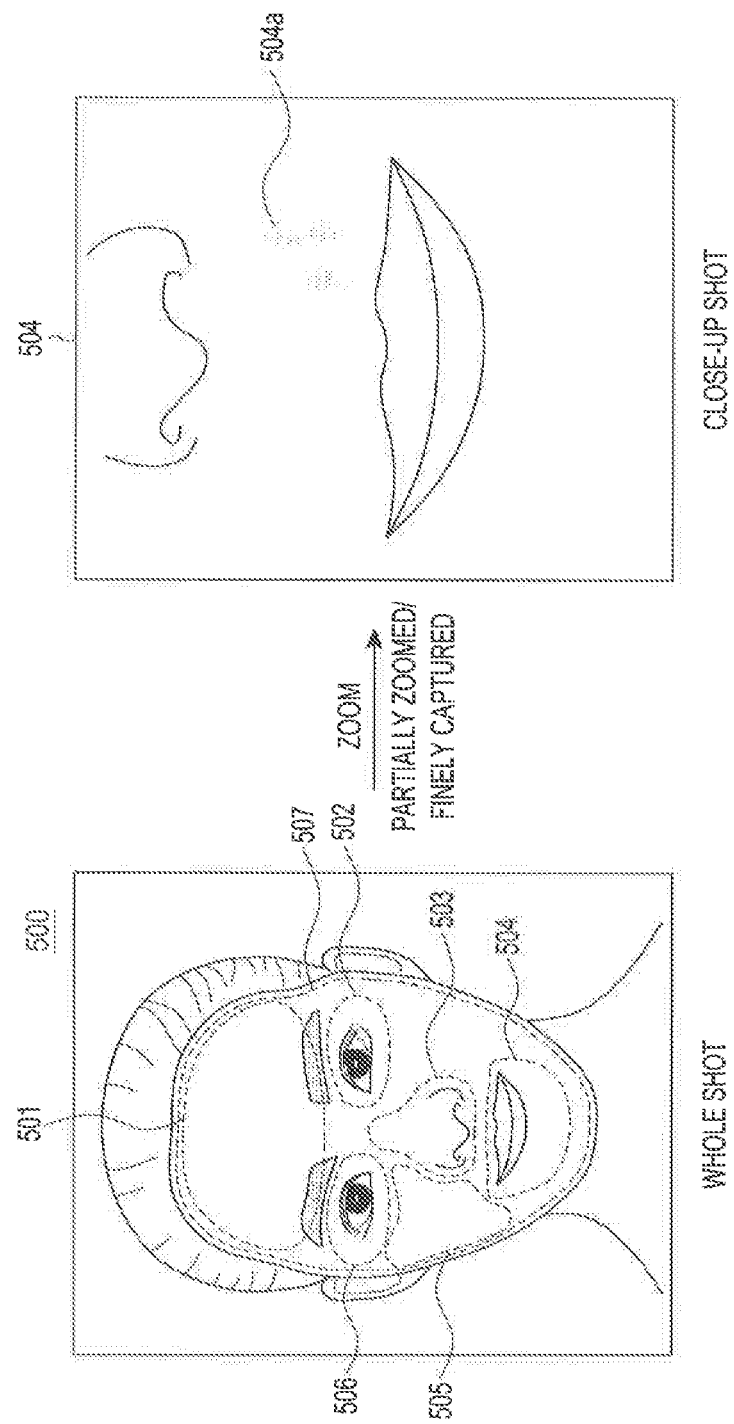

Referring to FIG. 5E, upon identifying the mouth edge 504 in the image 500 being captured, the electronic device may zoom in a region of the mouth edge 504 to partially zoom in or finely capture the region. The electronic device may obtain skin analysis information that is based on at least one analysis item, from the captured image obtained by partially zooming in the region of the mouth edge 504. For example, the skin analysis information may include information about pigmentation 504a in the region of the mouth edge 504.

Figure 5F:
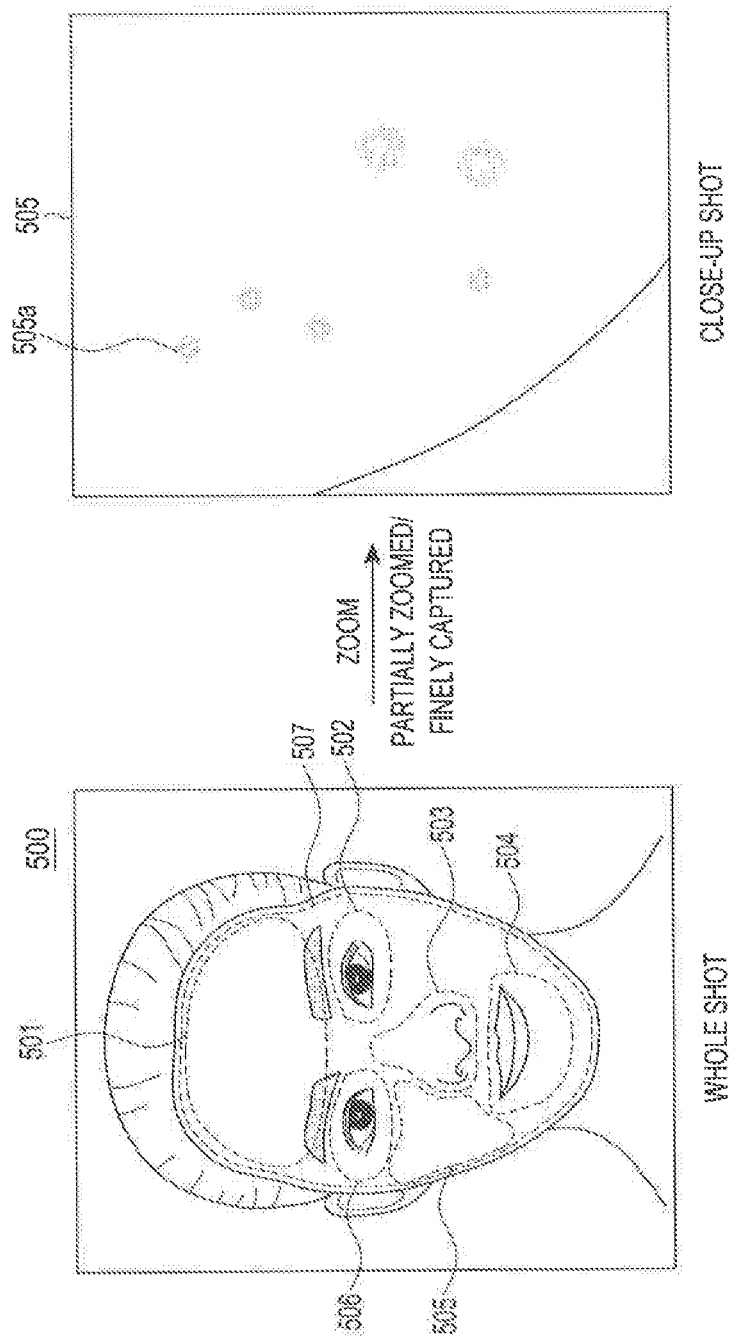

Referring to FIG. 5F, upon identifying the cheek 505 in the image 500 being captured, the electronic device may zoom in a region of the cheek 505 to partially zoom in or finely capture the region. The electronic device may obtain skin analysis information that is based on at least one analysis item, from the captured image obtained by partially zooming in the region of the cheek 505. For example, the skin analysis information may include information about acne 505a in the region of the cheek 505.

Figure 5G:
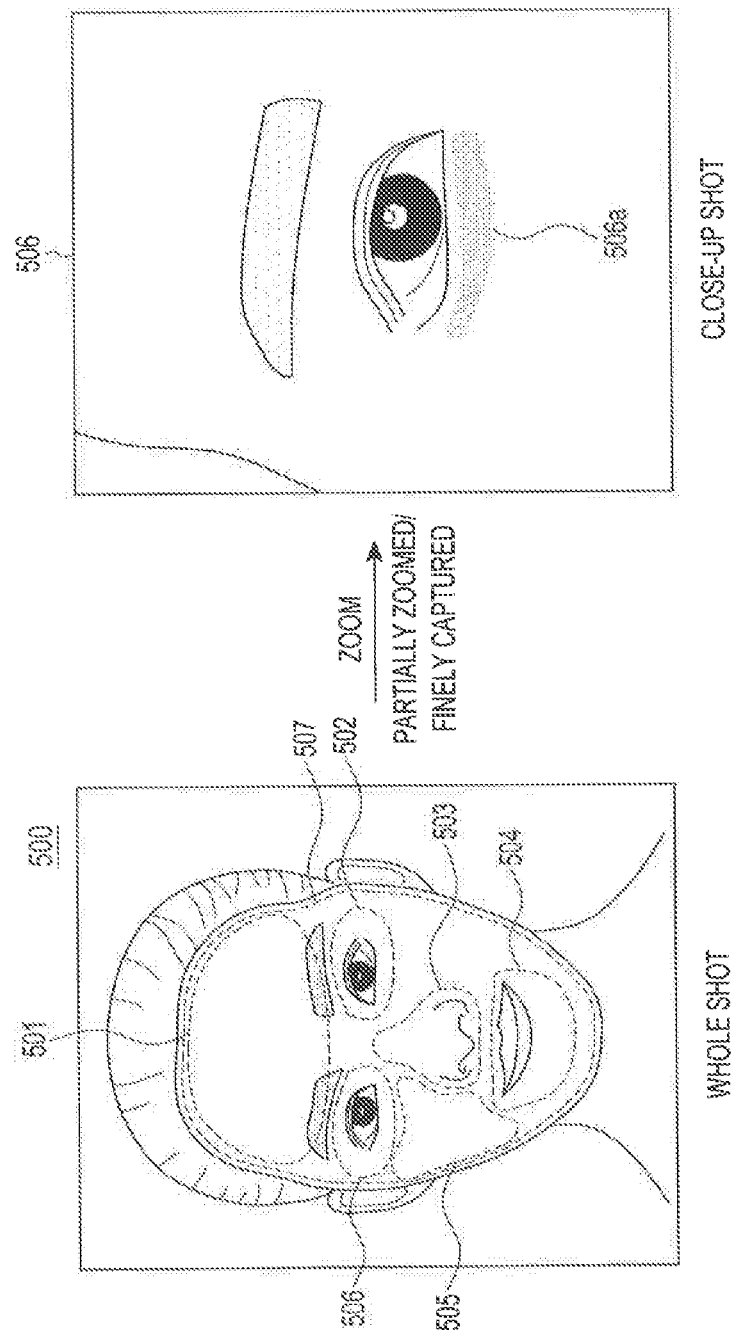

Referring to FIG. 5G, upon identifying the left eye 506 in the image 500 being captured, the electronic device may zoom in a region of the left eye 506 to partially zoom in or finely capture the region. The electronic device may obtain skin analysis information that is based on at least one analysis item, from the captured image obtained by partially zooming in the region of the left eye 506. For example, the skin analysis information may include information about dark circles 506a in the region of the left eye 506.

Figure 5H:
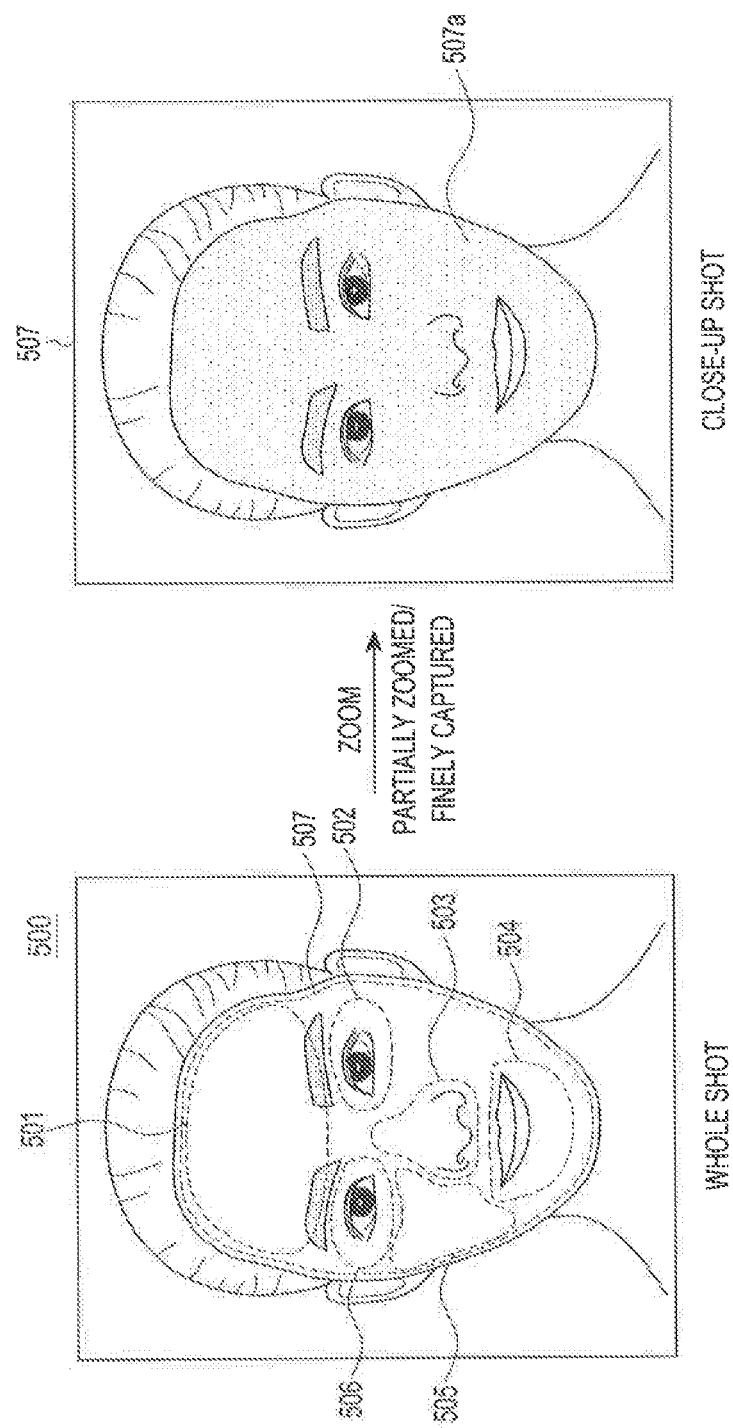

Referring to FIG. 5H, upon identifying the face 507 in the image 500 being captured, the electronic device may zoom in a region of the face 507 to partially zoom in or finely capture the region. The electronic device may obtain skin analysis information that is based on at least one analysis item, from the captured image obtained by partially zooming in the region of the face 507. For example, the skin analysis information may include information about skin tone 507a in the region of the face 507.

Figure 6:
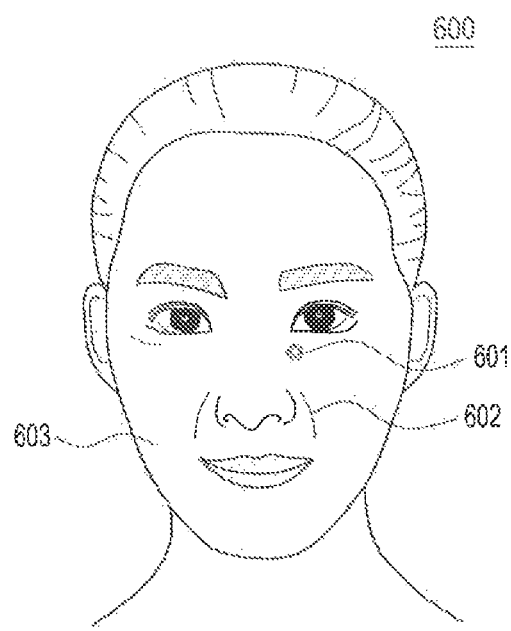
FIG. 6 illustrates face analysis items according to various embodiments of the present disclosure.

FIG. 6 illustrates face analysis items according to various embodiments of the present disclosure.

Referring to FIG. 6, the electronic device has captured an image 600 including at least one face region, and may identify at least one analysis item in the captured image 600. For example, the electronic device may identify acne 601, wrinkles 602 or pigmentation 603, as an analysis item.

Figure 7:
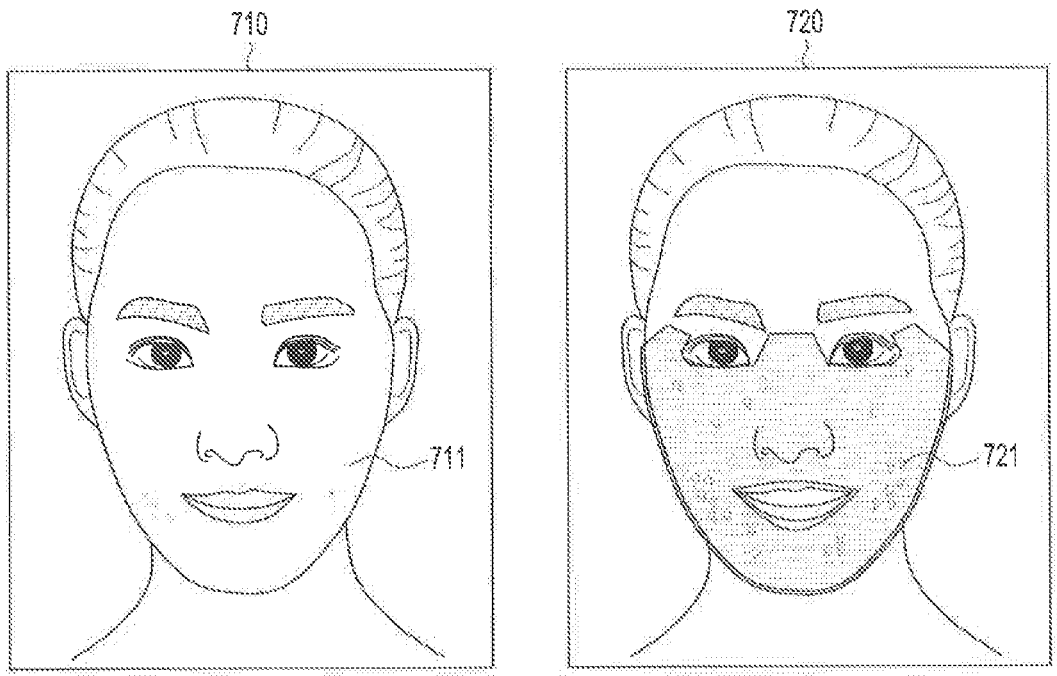
FIGS. 7, 8, 9, 10, and 11 illustrate an operation of analyzing face analysis items according to various embodiments of the present disclosure.

FIG. 7 illustrates an operation of analyzing a face analysis item according to various embodiments of the present disclosure.

Referring to FIG. 7, the electronic device may analyze pigmentation 711 among the analysis items in a captured image 710.

According to various embodiments of the present disclosure, the electronic device may generate an image 720 obtained by inverting the color of the pigmented part in the captured image. The electronic device may determine the color-inversed region in the image 720, thereby to identify at least one pigmented part 721. For example, the electronic device may determine whether the pigmentation has been improved or worsened than before, depending on the number of pigmented parts.

Figure 8:
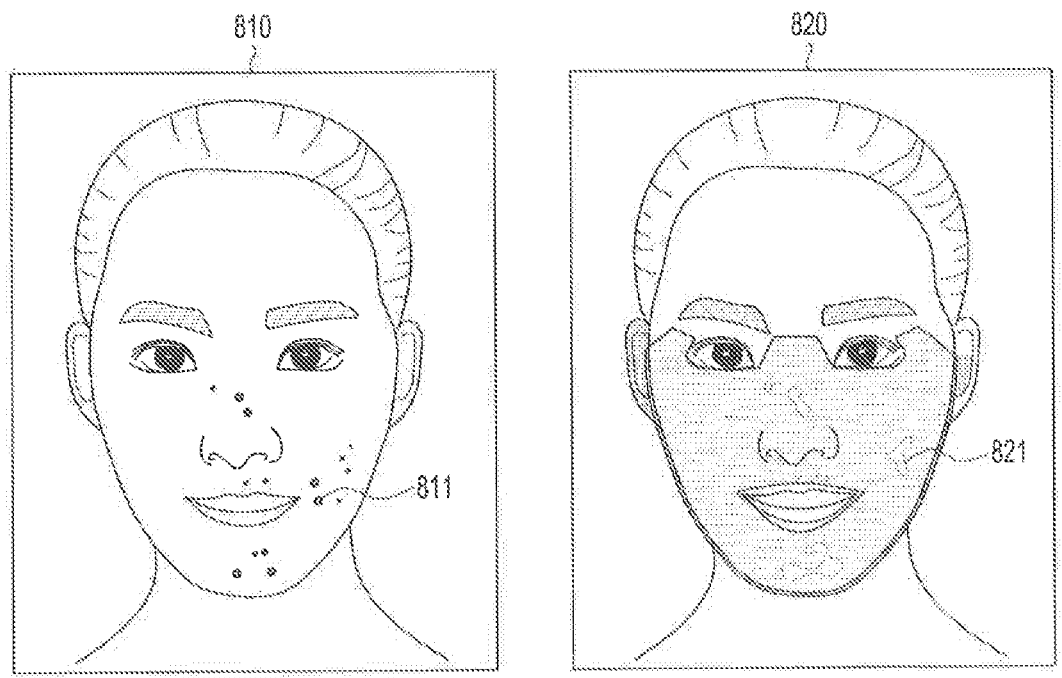

FIG. 8 illustrates an operation of analyzing a face analysis item according to various embodiments of the present disclosure.

Referring to FIG. 8, the electronic device may analyze acne 811 among the analysis items in a captured image 810.

According to various embodiments of the present disclosure, the electronic device may generate an image 820 obtained by inverting the color of the part where acne is identified in the captured image. For example, the electronic device may determine the color-inversed region in the image 820, thereby to identify at least one acne spots 821. For example, the electronic device may determine whether the acne has increased or decreased than before, depending on the number of acne spots.

Figure 9:
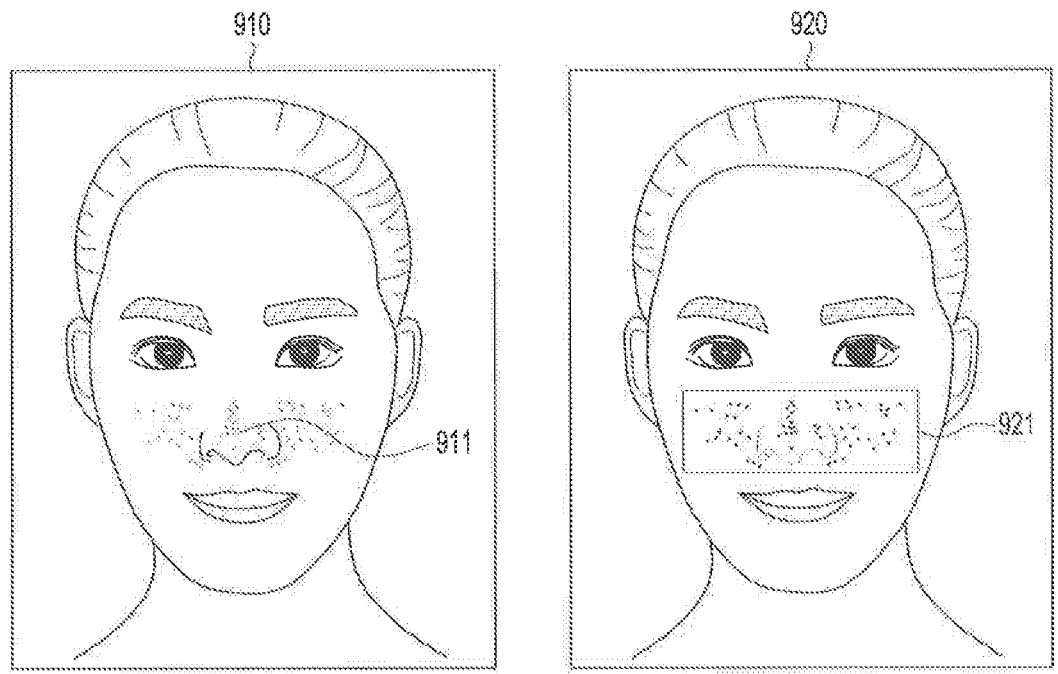

FIG. 9 illustrates an operation of analyzing a face analysis item according to various embodiments of the present disclosure.

Referring to FIG. 9, the electronic device may analyze pores 911 among the analysis items in a captured image 910.

According to various embodiments of the present disclosure, the electronic device may generate an image 920 obtained by darkening the color of the part where pores are identified in the captured image. For example, the electronic device may determine the color-darkened region 921 in the image 920, thereby to identify at least one pore. For example, the electronic device may determine whether the pores have increased or decreased than before, depending on the number of pores.

Figure 10:
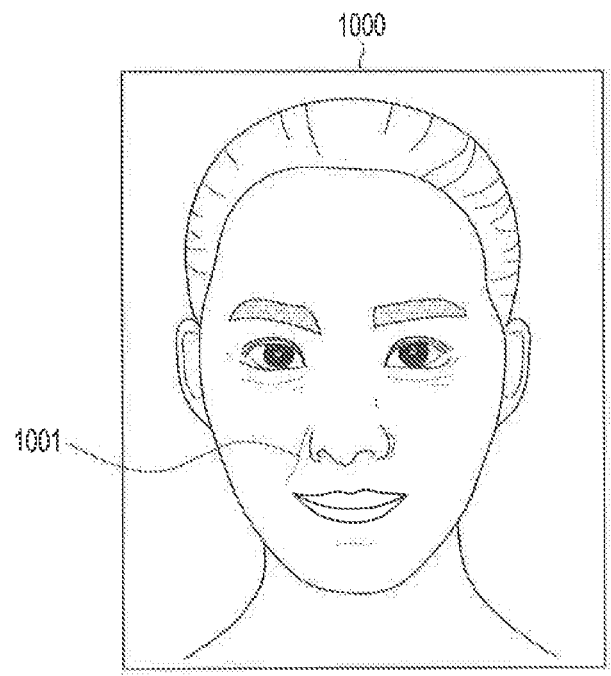

FIG. 10 illustrates an operation of analyzing a face analysis item according to various embodiments of the present disclosure.

Referring to FIG. 10, the electronic device may analyze wrinkles 1001 among the analysis items in a captured image 1000.

According to various embodiments of the present disclosure, the electronic device may represent wrinkle lines 1001 in a region where wrinkles are identified in the captured image 1000. For example, the electronic device may determine the presence/absence of wrinkles by determining at least one wrinkle line 1001 in the captured image 1000.

According to various embodiments of the present disclosure, the electronic device may determine the thickness or the number of at least one wrinkle line represented in the captured image. For example, the electronic device may determine whether the wrinkles have been deeper than before, depending on the thickness of the at least one wrinkle line, and may determine whether wrinkles have increased or decreased than before, depending on the number of wrinkle lines.

Figure 11:
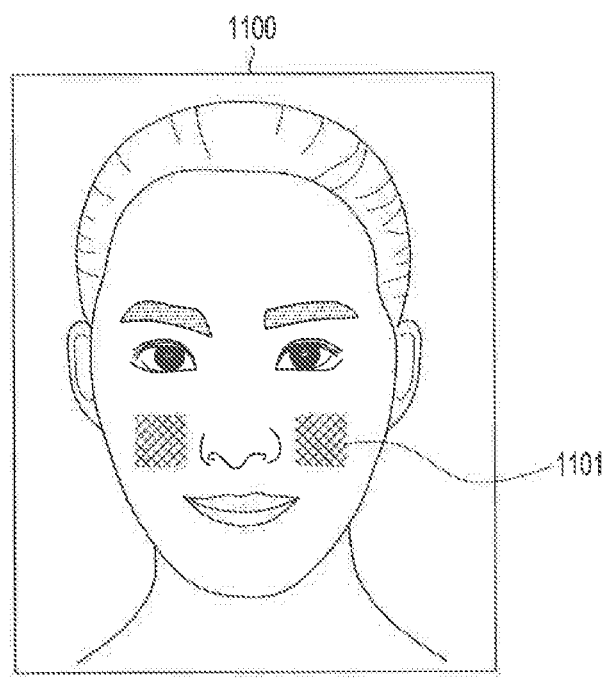

FIG. 11 illustrates an operation of analyzing a face analysis item according to various embodiments of the present disclosure.

Referring to FIG. 11, the electronic device may analyze skin tone 1101 among the analysis items in a captured image 1100.

According to various embodiments of the present disclosure, the electronic device may set a part of the skin as a skin tone analysis region 1101 in the captured image 1100. For example, by determining at least one skin tone analysis region 1101 in the captured image 1100, the electronic device may compare a value obtained by measuring the at least one skin tone analysis region 1101 with the previously measured skin tone value, or may obtain a measurement value for the skin tone analysis region.

According to various embodiments of the present disclosure, the electronic device may analyze the skin tone analysis region 1101 in the captured image 1100. For example, the electronic device may measure the color, contrast, brightness, color temperature, and the like, of the skin tone analysis region, thereby to determine whether the measured skin tone looks duller or brighter than the previously measured skin tone.

Figure 12:
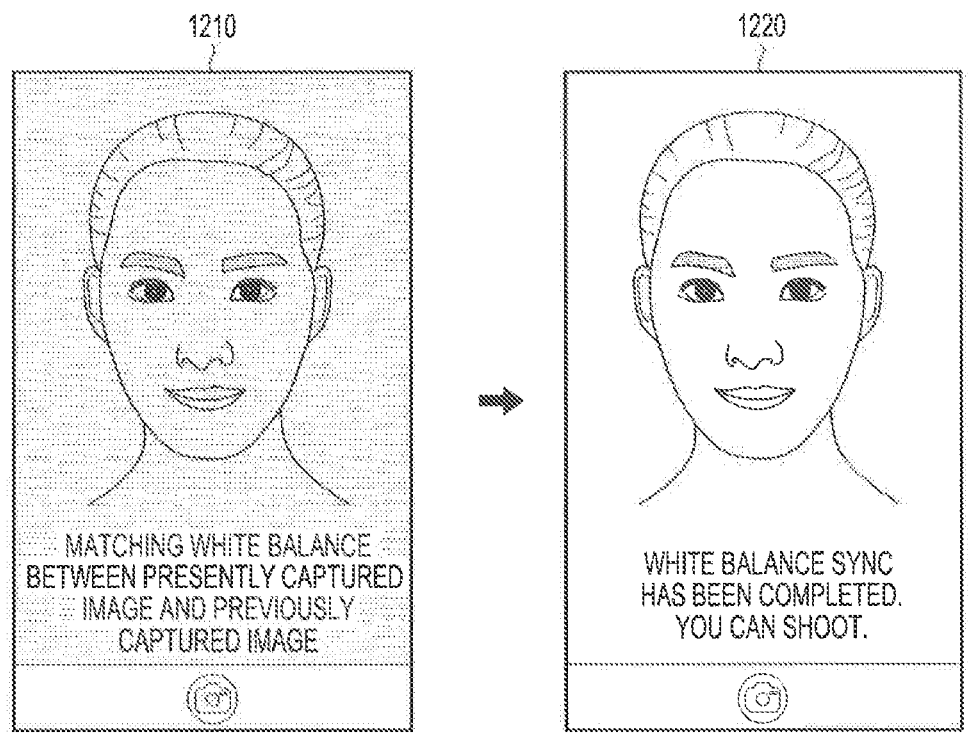
FIG. 12 illustrates a shooting operation for a face analysis according to various embodiments of the present disclosure.

FIG. 12 illustrates a shooting operation for a face analysis according to various embodiments of the present disclosure.

Referring to FIG. 12, it is assumed that the electronic device is capturing or shooting a face region for face analysis.

According to various embodiments of the present disclosure, the electronic device may determine the characteristics (e.g., resolution, image size, white balance, and the like) of the image presently being captured. The electronic device may compare the characteristics of the image presently being captured with the characteristics of the previously captured image. For example, if the characteristics (e.g., white balance) of the image presently being captured are not similar to the characteristics of the previously captured image, the electronic device may synchronize the characteristics of the image presently being captured with the characteristics of the previously captured image.

Referring to FIG. 12, the electronic device may display a screen 1210 indicating that the electronic device is matching the white balance of the image presently being captured with the white balance of the previously captured image. After synchronizing the characteristics of the image presently being captured with the characteristics of the previously captured image, the electronic device may display a screen 1220 indicating that shooting is possible because the synchronization of the white balance is completed.

According to various embodiments of the present disclosure, the user may determine on the screen 1220 that the current shooting situation in the electronic device is set to be similar to the previous shooting situation of the image for face analysis. Accordingly, it is possible to prevent the situation in which the analysis result for the face information may be different due to the causes, such as lighting, indoor/outdoor environment, weather, and the like, despite the same skin conditions.

Figure 13A:
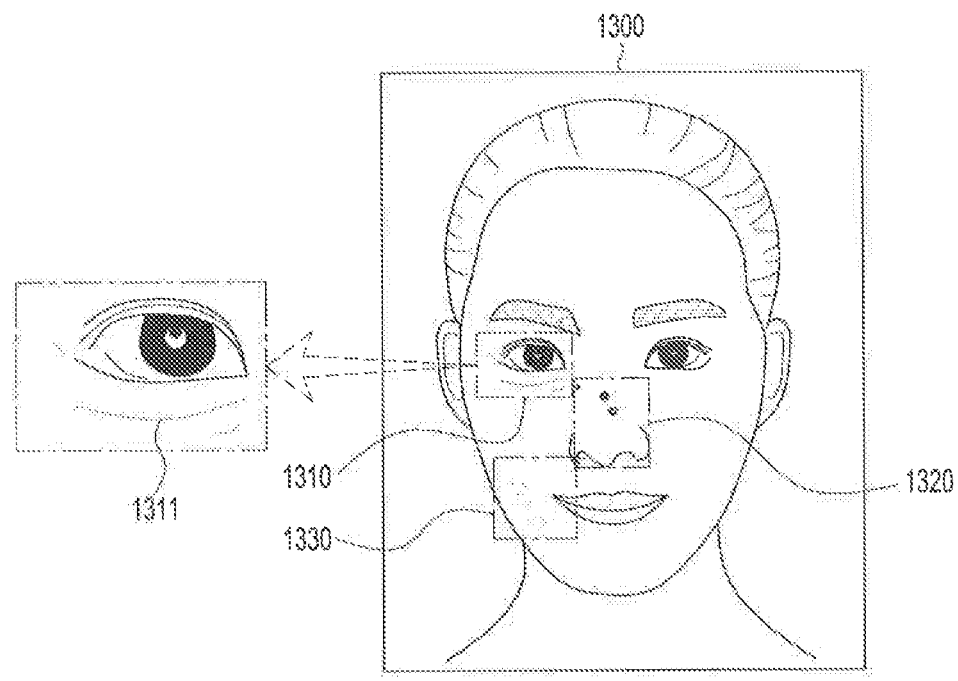
FIGS. 13A, 13B, and 13C illustrate a screen showing results of a face analysis according to various embodiments of the present disclosure.
Figure 13B:
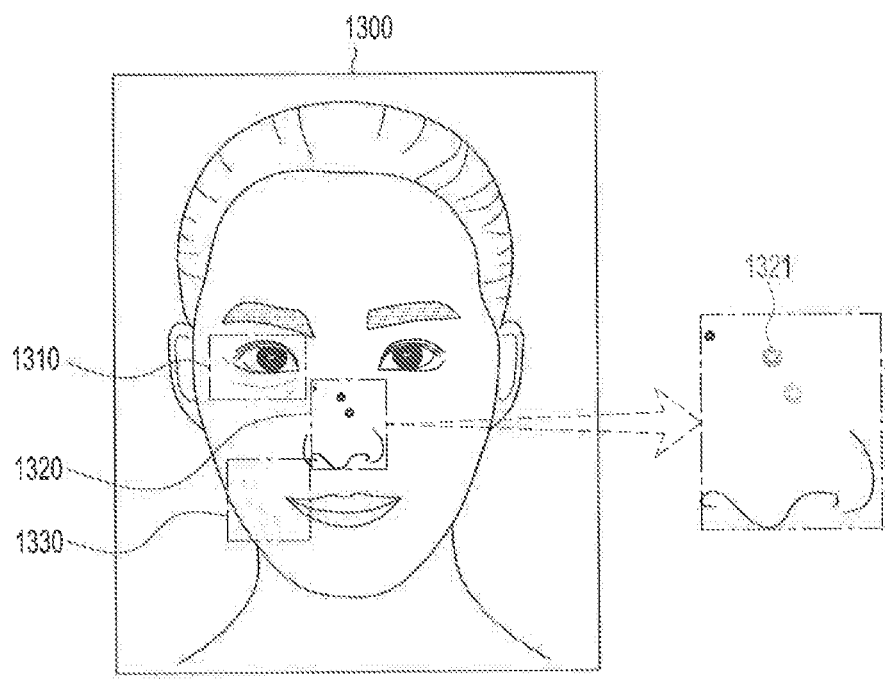
Figure 13C:
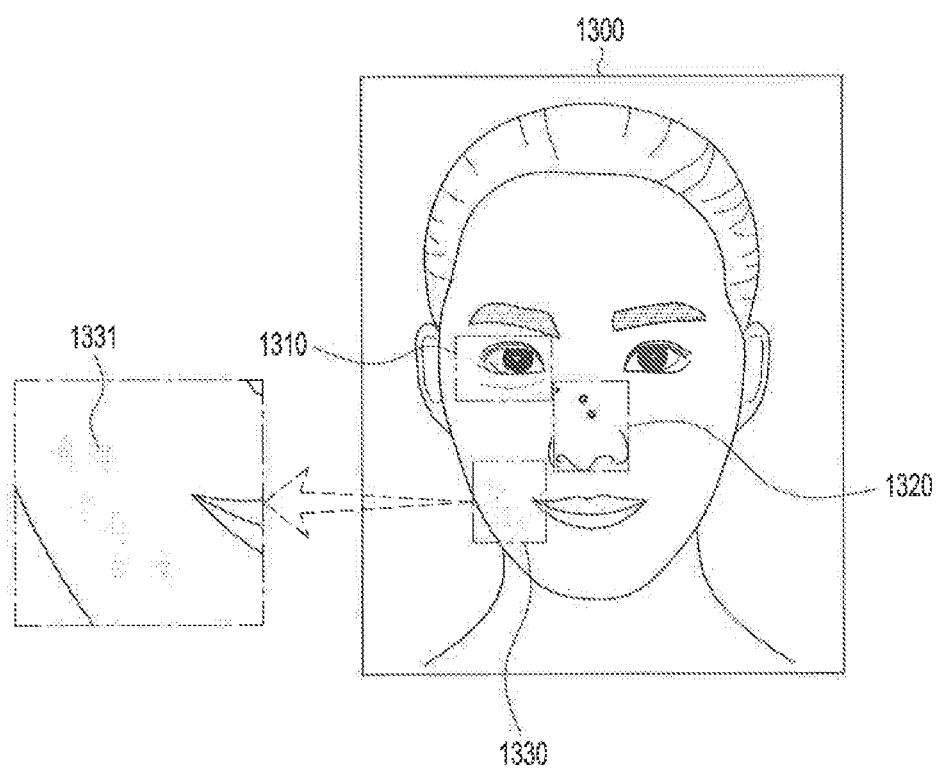

FIGS. 13A, 13B, and 13C illustrate a screen showing results of a face analysis according to various embodiments of the present disclosure.

Referring to FIGS. 13A, 13B, and 13C, according to various embodiments of the present disclosure, upon identifying at least one face region in a captured image, the electronic device may zoom in or finely capture the at least one face region. For example, the electronic device may generate an analysis result screen 1300 including the zoomed in or finely captured region in the face region corresponding to the captured image. For example, the analysis result screen 1300 may include a zoomed in or finely captured region for each of an eye 1310, a nose 1320 and a cheek 1330, which are identified as at least one face region.

Referring to FIG. 13A, the user may select the eye 1310 on the analysis result screen 1300. According to various embodiments of the present disclosure, the electronic device may output an image obtained by zooming in or finely capturing the eye 1310. For example, in the image obtained by zooming in or finely capturing the eye 1310, a line indicating at least one wrinkle 1311 around the eye 1310 may be displayed.

Referring to FIG. 13B, the user may select the nose 1320 on the analysis result screen 1300. According to various embodiments of the present disclosure, the electronic device may output an image obtained by zooming in or finely capturing the nose 1320. For example, in the image obtained by zooming in or finely capturing the nose 1320, at least one acne spot 1321 around the nose 1320 may be displayed.

Referring to FIG. 13C, the user may select the cheek 1330 on the analysis result screen 1300. According to various embodiments of the present disclosure, the electronic device may output an image obtained by zooming in or finely capturing the cheek 1330. For example, in the image obtained by zooming in or finely capturing the cheek 1330, the color of at least one pigmented part 1331 around the cheek 1330 may be displayed in a highlighted manner.

Figure 14:
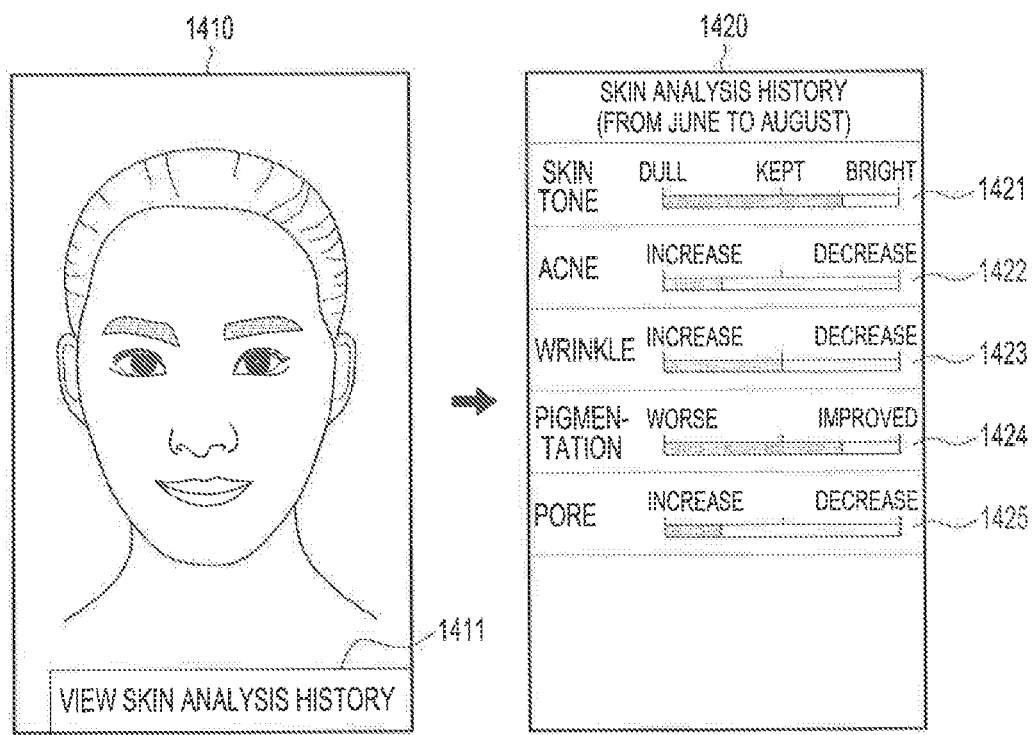
FIGS. 14, 15, 16, 17, and 18 illustrate a screen showing results of a skin analysis according to various embodiments of the present disclosure.

FIG. 14 illustrates a screen showing results of a skin analysis according to various embodiments of the present disclosure.

Referring to FIG. 14, an analysis result screen 1410 may include a selection item of View Skin Analysis History 1411 for showing the history of skin analysis results for each analysis item.

According to various embodiments of the present disclosure, if the View Skin Analysis History 1411 is selected, the electronic device may switch to a skin analysis history screen 1420.

The skin analysis history screen 1420 according to various embodiments of the present disclosure may show the history of skin analysis results for each of skin analysis items (e.g., skin tone, acne, wrinkles, pigmentation, pores, and the like) measured in a specific period (e.g., from June to August).

For example, a skin tone measurement result 1421 may show that the measured skin tone is brighter than before. An acne measurement result 1422 may show that the measured acne has increased than before. A wrinkle measurement result 1423 may show that the number of measured wrinkles is similar to the number of previous wrinkles. A pigmentation measurement result 1424 may show that the color of the pigmented parts is lighter than before. A pore measurement result 1425 may show that the number of pores has increased than before.

Figure 15:
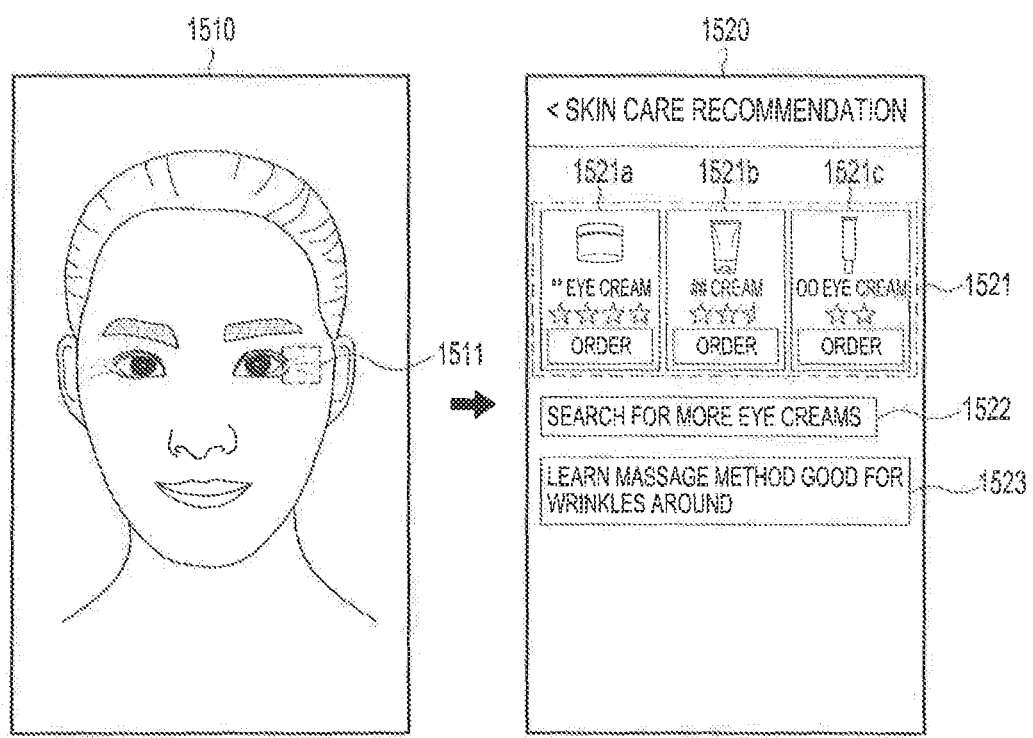

FIG. 15 illustrates a screen showing results of a skin analysis according to various embodiments of the present disclosure.

Referring to FIG. 15, according to various embodiments of the present disclosure, the electronic device may analyze a specific face region, and recommend ways to improve the face region depending on the analysis results.

Upon identifying a region around the eyes in a captured image 1510, the electronic device may analyze the skin conditions of the region around the eyes, and display the analysis results. For example, as a result of the analysis, the electronic device may determine that new wrinkles are identified or found around the eyes of a specific user or the number of wrinkles has increased than before.

According to various embodiments of the present disclosure, the electronic device may provide a skin care recommendation screen 1520 including ways to improve wrinkles. For example, if the user selects wrinkle marks 1511 in the captured image 1510, the electronic device may switch from the screen showing the captured image 1510 to the skin care recommendation screen 1520.

The skin care recommendation screen 1520 according to various embodiments of the present disclosure may include cosmetics 1521 which are good for wrinkles, a run button (or execution button) 1522 for searching for more eye creams, or a run button 1523 for recommending massage methods good for wrinkles around eyes. For example, the cosmetics 1521 which are good for wrinkles may include  eye cream 1521a, ##cream 1521b, or oo eye cream 1521**c, and may further include a run button by which the user can rate each cosmetic, or order specific cosmetic.

Figure 16:
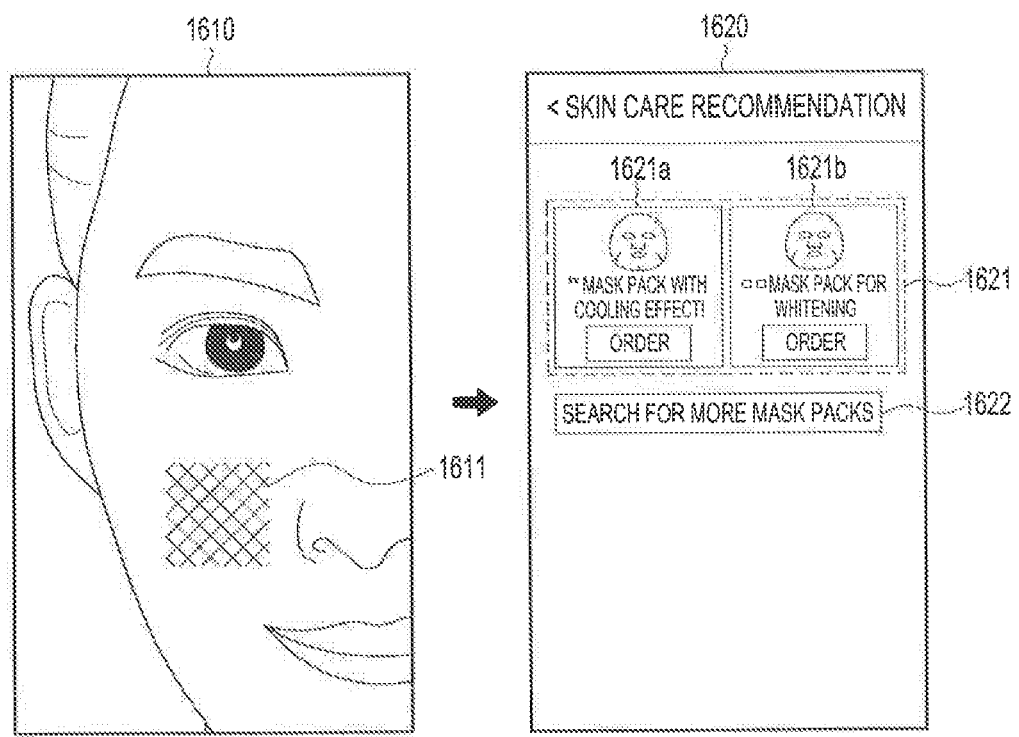

FIG. 16 illustrates a screen showing results of a skin analysis according to various embodiments of the present disclosure.

Referring to FIG. 16, according to various embodiments of the present disclosure, the electronic device may analyze a specific face region, and recommend ways to improve the face region depending on the analysis results. For example, as a result of the analysis, the electronic device may identify the part where the skin tones are changed around the cheeks of a specific user.

Upon identifying a region around the cheeks in a captured image 1610, the electronic device may display a skin tone analysis region 1611, in which skin tones for a specific region of the cheeks are analyzed.

According to various embodiments of the present disclosure, the electronic device may provide a skin care recommendation screen 1620 including ways to improve skin tones. For example, if the user selects the skin tone analysis region 1611 in the captured image 1610, the electronic device may switch from the screen showing the captured image 1610 to the skin care recommendation screen 1620.

The skin care recommendation screen 1620 according to various embodiments of the present disclosure may include mask packs 1621 which are good for improvement of skin tones, or a run button 1622 for searching for more mask packs. For example, the mask packs 1621 which are good for improvement of skin tones may include  mask pack 1621a or □□ mask pack 1621**b, and may further include a run button by which the user can go to a screen showing the characteristics of each mask pack, or order a specific mask pack.

Figure 17:
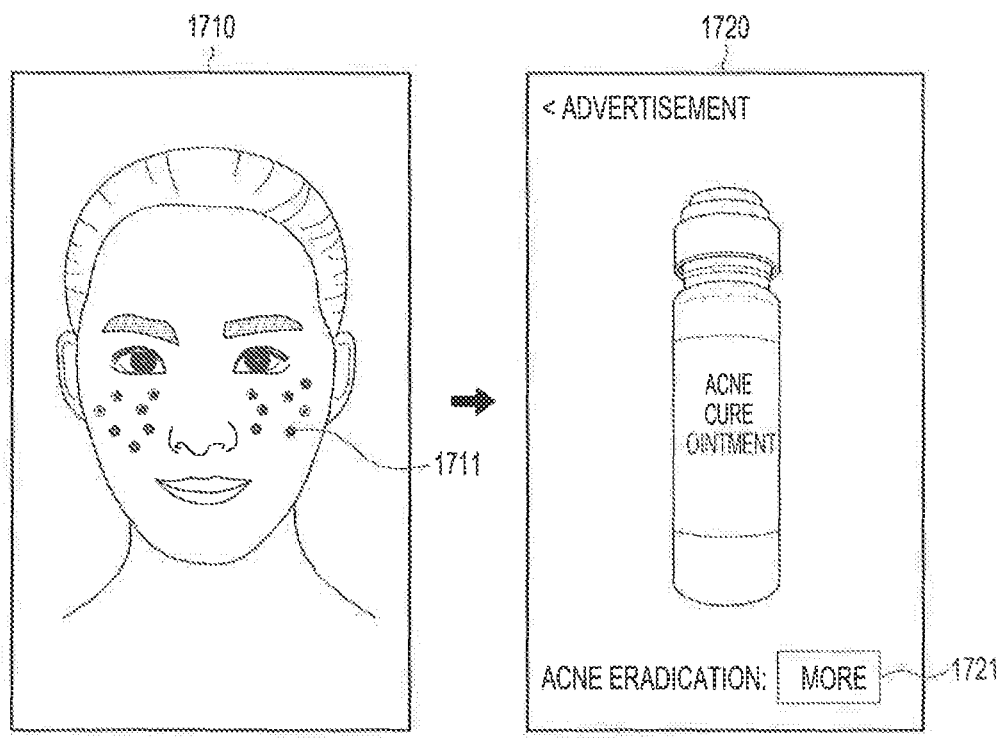

FIG. 17 illustrates a screen showing results of a skin analysis according to various embodiments of the present disclosure.

Referring to FIG. 17, according to various embodiments of the present disclosure, the electronic device may analyze a specific face region, and provide an advertising screen for a product capable of improving the face region depending on the analysis results.

Upon identifying a region around the cheeks or at least one acne spot in the region around the cheeks in a captured image 1710, the electronic device may display the identified acne 1711 in a highlighted manner.

According to various embodiments of the present disclosure, the electronic device may provide an advertising screen 1720 for advertising a product capable of improving the acne. For example, if the user selects the acne 1711 shown in the captured image 1710, the electronic device may switch from the screen showing the captured image 1710 to the advertising screen 1720.

The advertising screen 1720 according to various embodiments of the present disclosure may include an advertisement for acne treatment, or a 'More' run button 1721 for switching to a screen for description of the acne treatment.

Figure 18:
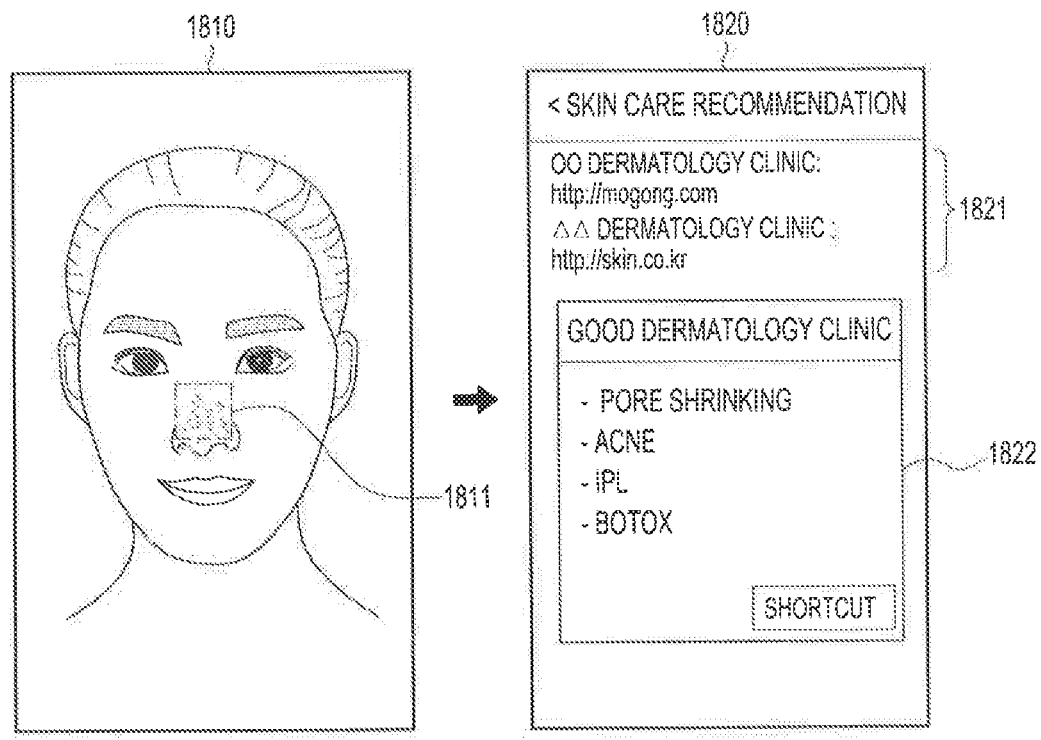

FIG. 18 illustrates a screen showing results of a skin analysis according to various embodiments of the present disclosure.

Referring to FIG. 18, according to various embodiments of the present disclosure, the electronic device may analyze a specific face region, and recommend ways to improve the face region depending on the analysis results.

Upon identifying the nose in a captured image 1810, the electronic device may display a pore analysis region 1811, in which the number of pores in the nose is analyzed.

According to various embodiments of the present disclosure, the electronic device may provide a skin care recommendation screen 1820 including ways to reduce the number of pores. For example, if the user selects the pore analysis region 1811 in the captured image 1810, the electronic device may switch from the screen showing the captured image 1810 to the skin care recommendation screen 1820.

The skin care recommendation screen 1820 according to various embodiments of the present disclosure may include information 1821 about the dermatology clinics known for pore treatment, or an advertisement 1822 for a specific dermatology clinic. For example, the advertisement 1822 for a specific dermatology clinic may include a screen showing medical departments of the dermatology clinic, or a shortcut run button for switching to an information screen of the dermatology clinic.

Figure 19:
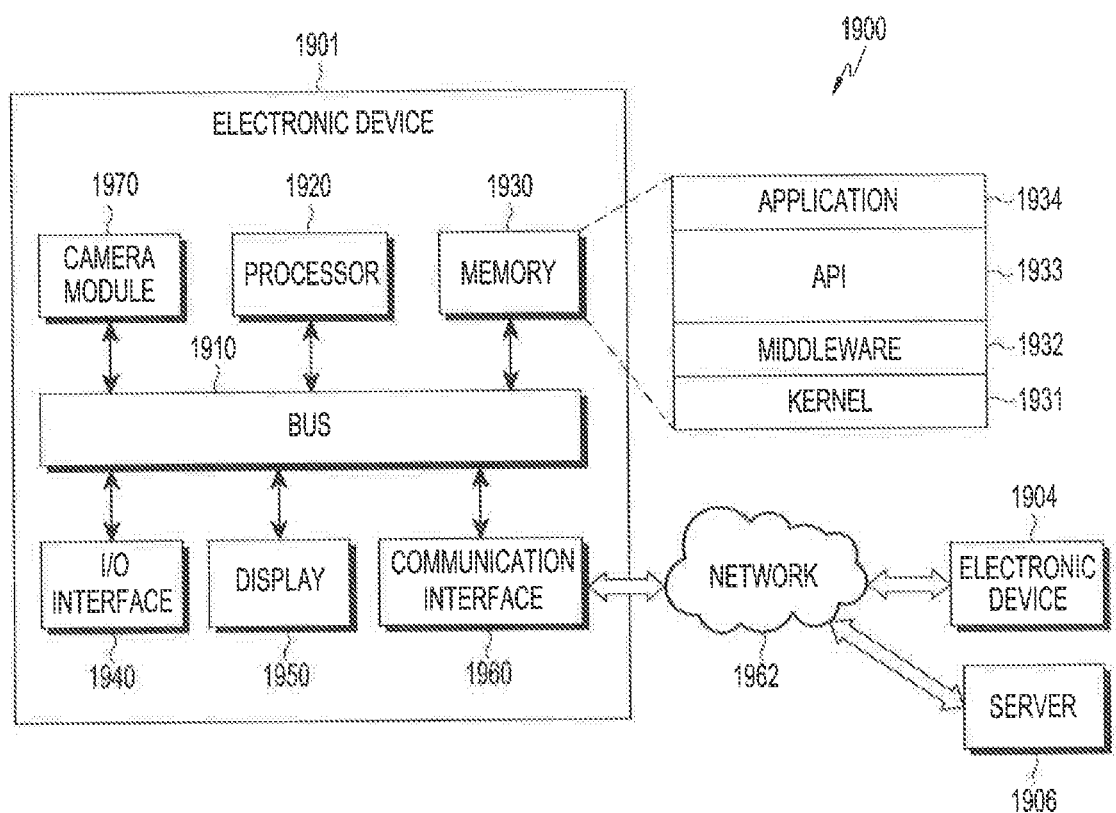
FIG. 19 illustrates a network environment according to various embodiments of the present disclosure.

FIG. 19 illustrates a network environment according to various embodiments of the present disclosure.

Referring to FIG. 19, a network environment 1900 may include at least one electronic device 1901 or 1904, or a server 1906. The at least one electronic device 1901 or 1904 may be connected to the server 1906 over a network 1962.

The electronic device 1901 may include a bus 1910, a processor 1920, a memory 1930, an input/output (I/O) interface 1940, a display 1950, a communication interface 1960, and a camera module 1970.

The bus 1910 may be a circuit that connects the above-described components to each other, and delivers communication information (e.g., a control message) between the above-described components.

The processor 1920 may, for example, receive a command from the above-described other components (e.g., the memory 1930, the I/O interface 1940, the display 1950, the communication unit 1960, the camera module 1970, and the like) through the bus 1910, decrypt the received command, and perform the operation or data processing based on the decrypted command.

The processor 1920 may control the overall operation of the electronic device 1901. According to various embodiments of the present disclosure, the processor 1920 may include at least one controller (e.g., the controller 110).

The memory 1930 may store the command or data that is received from or generated by the processor 1920 or other components (e.g., the I/O interface 1940, the display 1950, the communication interface 1960, the camera module 1970, and the like). The memory 1930 may include programming modules, such as, for example, a kernel 1931, a middleware 1932, an application programming interface (API) 1933 or an application(s) 1934. Each of the above-described programming modules may be configured by software, firmware, hardware or a combination thereof.

The kernel 1931 may control or manage the system resources (e.g., the bus 1910, the processor 1920, the memory 1930, and the like) used to execute the operation or function implemented in the other programming modules (e.g., the middleware 1932, the API 1933 or the application 1934). Further, the kernel 1931 may provide an interface by which the middleware 1932, the API 1933 or the application

1934 may access individual components of the electronic device 1901, and control or manage the individual components.

The middleware 1932 may perform an intermediary role so that the API 1933 or the application 1934 may communicate with the kernel 1931 thereby to exchange data with each other. Further, in response to work requests received from the application 1934, the middleware 1932 may, for example, perform control (e.g., scheduling or load balancing) for the work requests by using a method of assigning a priority capable of using the system resources (e.g., the bus 1910, the processor 1920, the memory 1930, and the like) of the electronic device 1901 to at least one of the application(s) 1934.

The API 1933 may include at least one interface or function (e.g., a command) for, for example, file control, window control, image processing, character control, and the like, as an interface by which the application 1934 controls a function provided in the kernel 1931 or the middleware 1932.

According to various embodiments of the present disclosure, the application 1934 may include a short message service (SMS)/multimedia messaging service (MMS) application, an E-mail application, a calendar application, an alarm application, a healthcare application (e.g., an application for measuring the amount of exercise or the blood glucose), or an environmental information application (e.g., an application for providing information about the pressure, humidity, temperature, and the like). Additionally or alternatively, the application 1934 may be an application related to information exchange between the electronic device 1901 and an external electronic device (e.g., the electronic device 1904). The application related to information exchange may include, for example, a notification relay application for relaying specific information to the external electronic device, or a device management application for managing the external electronic device.

For example, the notification relay application may include a function of delivering the notification information generated in other applications (e.g., the SMS/MMS application, the E-mail application, the healthcare application, the environmental information application, and the like) of the electronic device 1901 to the external electronic device (e.g., the electronic device 1904). Additionally or alternatively, the notification relay application may, for example, receive notification information from the external electronic device (e.g., the electronic device 1904), and provide the received notification information to the user. The device management application may, for example, manage (e.g., install, delete or update) a function (e.g., a function of controlling the turn-on/off of the external electronic device itself (or some of its parts), or the brightness (or resolution) of the display) for at least a part of the external electronic device (e.g., the electronic device 1904) communicating with the electronic device 1901, manage an application operating in the external electronic device, or manage the service (e.g., a call service or a messaging service) provided in the external electronic device.

According to various embodiments of the present disclosure, the application 1934 may include an application that is specified depending on the properties (e.g., the type of the electronic device) of the external electronic device (e.g., the electronic device 1904). For example, if the external electronic device is an MP3 player, the application 1934 may include an application related to music playback. Similarly, if the external electronic device is a mobile medical device, the application 1934 may include an application related to healthcare. In one embodiment of the present disclosure, the application 1934 may include at least one of an application specified in the electronic device 1901, or an application received from the external electronic device (e.g., the server 1906 or the electronic device 1904).

The I/O interface 1940 may deliver the command or data that is received from the user through an I/O device (e.g., a sensor, a keyboard or a touch screen), to the processor 1920, the memory 1930, the communication interface 1960 or the camera module 1970 through, for example, the bus 1910. For example, the I/O interface 1940 may provide the data for a user's touch made on the touch screen, to the processor 1920. Further, the I/O interface 1940 may output, through the I/O device (e.g., a speaker or a display), the command or data that is received from the processor 1920, the memory 1930, the communication interface 1960 or the camera module 1970 through, for example, the bus 1910. For example, the I/O interface 1940 may output the voice data processed by the processor 1920, to the user through the speaker.

The display 1950 may display a variety of information (e.g., multimedia data, text data, and the like), for the user.

The communication interface 1960 may connect communication between the electronic device 1901 to the external device (e.g., the electronic device 1904 or the server 1906). For example, the communication interface 1960 may be connected to the network 1962 by wireless communication or wired communication, to communicate with the external device. The wireless communication may include at least one of, for example, Wi-Fi, Bluetooth (BT), near field communication (NFC), GPS or cellular communication (e.g., long term evolution (LTE), LTE-advanced (LTE-A), code division multiple access (CDMA), wideband CDMA (WCDMA), universal mobile telecommunication system (UNITS), wireless broadband (WiBro), global system for mobile communications (GSM), and the like). The wired communication may include at least one of, for example, a universal serial bus (USB), a high definition multimedia interface (HDMI), recommended standard 232 (RS-232), or plain old telephone service (POTS).

The camera module 1970 may zoom in or finely capture a specific region by zooming in an image being captured, by being controlled based on the information obtained from other components (e.g., the processor 1920, the memory 1930, the I/O interface 1940, the communication interface 1960, and the like).

In an embodiment of the present disclosure, the network 1962 may be a telecommunications network. The telecommunications network may include at least one of a computer network, the Internet, Internet of things (IoT), or a telephone network. In one embodiment of the present disclosure, a protocol (e.g., a transport layer protocol, a data link layer protocol or a physical layer protocol) for communication between the electronic device 1901 and the external device may be supported by at least one of the application 1934, the API 1933, the middleware 1932, the kernel 1931 or the communication interface 1960.

According to various embodiments of the present disclosure, the electronic device may calculate the lighting environment of the image that is being captured using an auto white balance function (or a white balance auto setup function). For example, using the calculated lighting environment, the electronic device may capture an image so that the batch white balance may be set. Further, even in the shooting environment where there is no external light source, the electronic device may capture an image so that the batch white balance may be set, by adjusting the light source (e.g., a light emitting diode (LED) light source) included in the electronic device.

If the white balance is set according to the auto white balance function during capturing, a face region in the captured image may be set to a different color according to the white balance that is set to correspond to each captured image.

In order to set the color of the face region for multiple images in batches, it is possible to use only the light source included in the electronic device after blocking the external light source. However, an electronic device including the light source for implementing this method may be large and heavy for the user to carry.

According to various embodiments of the present disclosure, the electronic device may include a front camera or a rear camera. For example, if an image is captured using the front camera, the rear camera may calculate the shooting environment to set the white balance of an image to be captured so that an image may be captured in the constant shooting environment. A detailed description thereof will be made below with reference to FIGS. 20A, 20B, 20C, and 21.

Figure 20A:
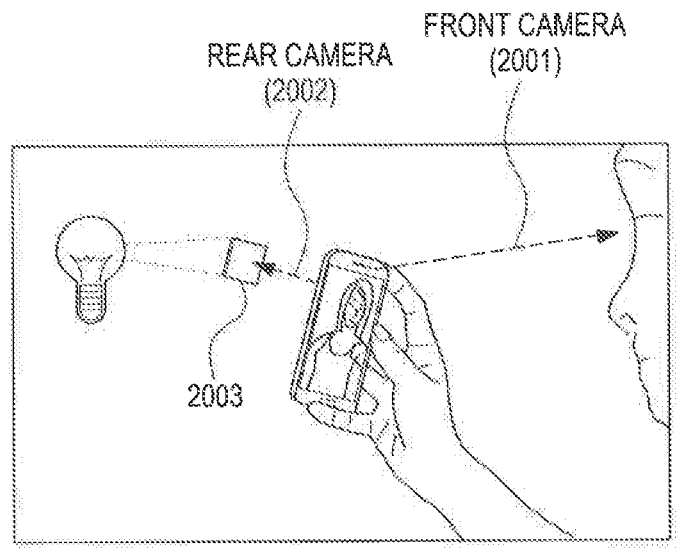
FIGS. 20A, 20B, and 20C illustrate a situation in which an electronic device analyzes a face according to various embodiments of the present disclosure.
Figure 20B:
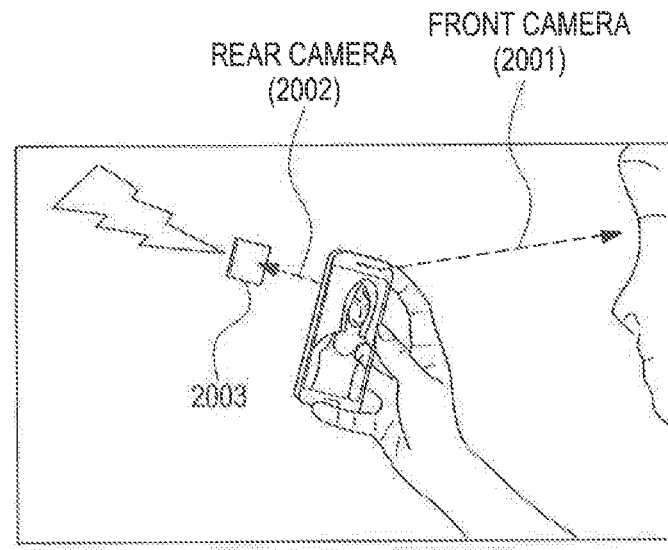
Figure 20C:
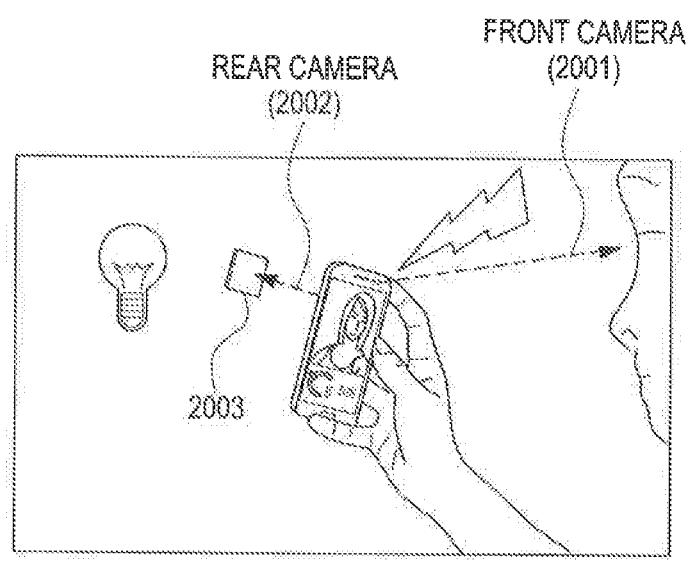

FIGS. 20A, 20B, and 20C illustrate a situation in which an electronic device analyzes face according to various embodiments of the present disclosure.

Referring to FIGS. 20A, 20B, and 20C, the electronic device may include a front camera 2001 or a rear camera 2002, and the rear camera 2002 may include a color balance card 2003.

According to various embodiments of the present disclosure, the electronic device may detect the lighting elements (or lighting components) of the surrounding environment in which the electronic device is capturing an image, using the color balance card 2003. For example, the color balance card 2003 may be equipment for shooting the correct color of the light by using the scattered reflection properties of the light, or may be equipment that is used for color correction. Although the color balance card 2003 is mounted in, for example, the rear camera 2002, the color balance card 2003 may be mounted in various other modules interworking with the electronic device.

According to various embodiments of the present disclosure, the electronic device may determine that the brightness of an image obtained through at least one camera module (e.g., the front camera 2001 or the rear camera 2002) is abnormal. For example, the case where the brightness of the image is determined to be abnormal may include a case where the light is brighter or darker than the set value, or a case where the face region cannot be obtained.

According to various embodiments of the present disclosure, if it is determined that the brightness of the image is abnormal, the electronic device may not store the image being captured by the camera module (e.g., the front camera 2001 or the rear camera 2002), determining that it is difficult to obtain an image.

Further, according to various embodiments of the present disclosure, if it is determined that the brightness of the image is abnormal, the electronic device may display a screen indicating the abnormality of the shooting situation, or output a sound alert indicating the abnormality of the shooting situation. Accordingly, the user may move the electronic device to the position where the normal shooting is possible. If it is determined that the normal shooting is possible, the electronic device may output again the screen or sound indicating that shooting is possible.

Referring to FIG. 20A, the electronic device may obtain an image including a face region using the front camera 2001, and calculate the lighting elements using the color balance card 2003 of the rear camera 2002.

According to various embodiments of the present disclosure, the electronic device may apply the calculated lighting elements to the obtained image including a face region. For example, as for the image to which the calculated lighting elements are applied, since the white balance is set regardless of the lighting components of the shooting surrounding, the image may be captured so as to correspond to the white balance of the face region of the previously stored image.

Referring to FIG. 20B, it is assumed that the electronic device is capturing or shooting an image using the front camera 2001. For example, the electronic device may analyze the image that is being captured by the front camera 2001.

According to various embodiments of the present disclosure, the electronic device may determine whether the lighting environment in which the electronic device is capturing an image is the extreme lighting environment (e.g., backlighting, low illuminance, overly bright lighting, and the like), depending on the result of analyzing the image. For example, if the lighting environment in which the electronic device is capturing an image using the front camera 2001 is determined as the extreme lighting environment, the electronic device may not store the image being captured by the front camera 2001, or control the front camera 2001 so that the shooting function may not be enabled.

According to various embodiments of the present disclosure, if the lighting environment in which the electronic device is capturing an image using the front camera 2001 is determined as the abnormal lighting environment, the electronic device may calculate the white balance using the color balance card 2003 and apply the calculated white balance value to the image that is being captured by the front camera 2001.

Referring to FIG. 20C, it is assumed that the electronic device is capturing or shooting an image using the rear camera 2002. For example, the electronic device may analyze the image that is being captured by the rear camera 2002.

According to various embodiments of the present disclosure, the electronic device may determine whether the lighting environment in which the electronic device is capturing an image is the extreme lighting environment (e.g., backlighting, low illuminance, overly bright lighting, and the like), depending on the result of analyzing the image. For example, if the lighting environment in which the electronic device is capturing an image using the rear camera 2002 is determined as the extreme lighting environment, the electronic device may not store the image being captured by the rear camera 2002, or control the rear camera 2002 so that the shooting function may not be enabled.

According to various embodiments of the present disclosure, if the lighting environment in which the electronic device is capturing an image using the rear camera 2002 is determined as the abnormal lighting environment, the electronic device may calculate the white balance using the color balance card 2003 and apply the calculated white balance value to the image that is being captured by the rear camera 2002.

Figure 21:
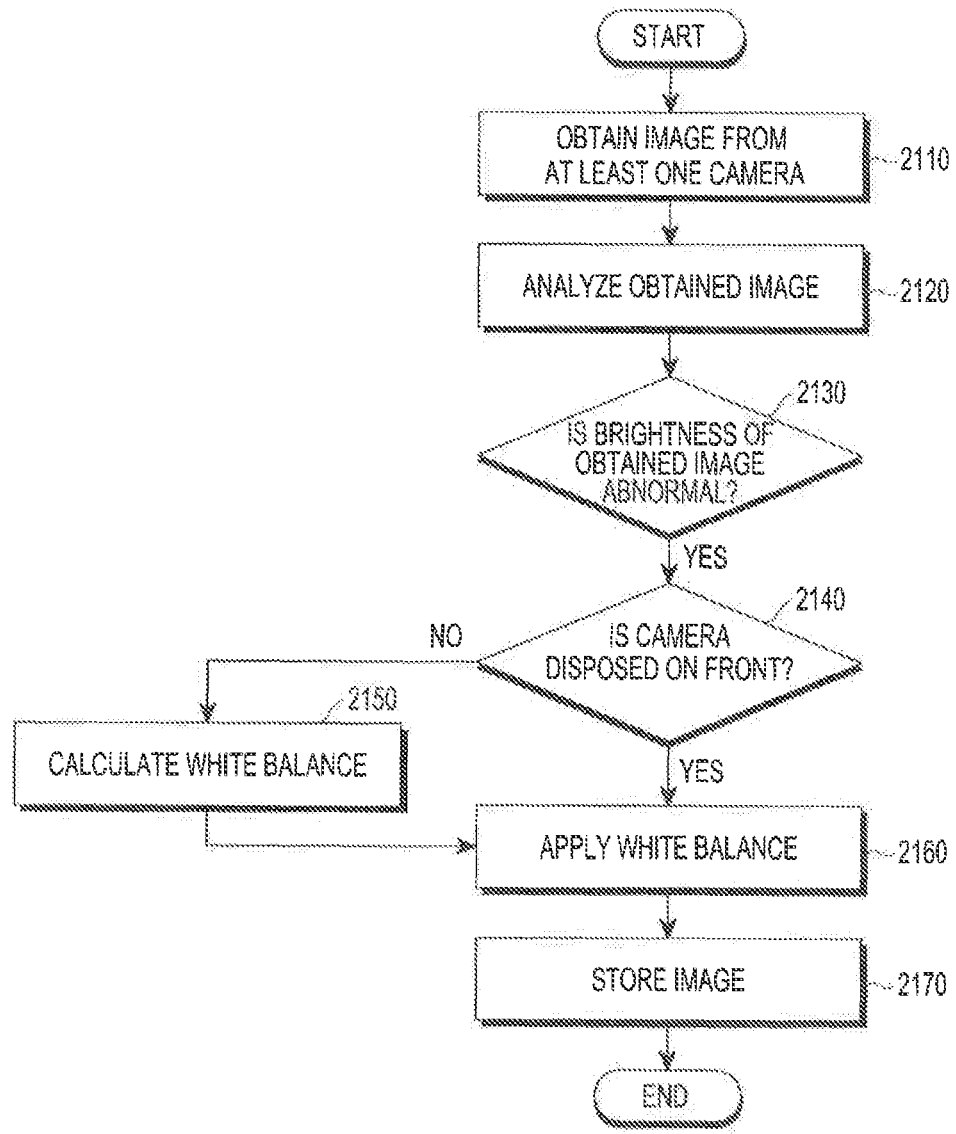
FIG. 21 is a flowchart illustrating an operation of analyzing skin information in an electronic device according to various embodiments of the present disclosure.

FIG. 21 is a flowchart illustrating an operation of analyzing skin information in an electronic device according to various embodiments of the present disclosure.

Referring to FIG. 21, in operation 2110, the electronic device may obtain an image from at least one camera.

In operation 2120, the electronic device may analyze the obtained image.

In operation 2130, the electronic device may determine whether the brightness of the obtained image is abnormal.

If it is determined in operation 2130 that the brightness of the obtained image is not abnormal, the electronic device may perform again operation 2110.

If it is determined in operation 2130 that the brightness of the obtained image is abnormal, the electronic device may determine in operation 2140 whether the camera that has captured the obtained image is a camera mounted on the front of the electronic device.

If it is determined in operation 2140 that the camera that has captured the obtained image is not a camera mounted on the front of the electronic device, the electronic device may calculate the white balance in operation 2150. For example, the white balance may be calculated using a module (e.g., the color balance card) capable of calculating the white balance, the module being provided in the camera that is not mounted on the front of the electronic device. In operation 2160, the electronic device may apply the white balance of the captured image as the calculated white balance, using the white balance calculated in operation 2150.

If it is determined in operation 2140 that the camera that has captured the obtained image is a camera mounted on the front of the electronic device, the electronic device may apply the white balance to the captured image in operation 2160. For example, the image to which the white balance is applied in operation 2160 may be an image to which a white balance value is applied, that is stored in advance because the color balance card is not provided in the camera mounted on the front of the electronic device.

In operation 2170, the electronic device may store the image. For example, the stored image may be an image to which the white balance is applied.

At least one of operations 2110 to 2170 shown in FIG. 21 may be omitted, or at least one other operation may be added in between operations 2110 to 2170. Further, operations 2110 to 2170 in FIG. 21 may be performed in the depicted order, or at least one of operations 2110 to 2170 may be changed in execution order.

Figure 22A:
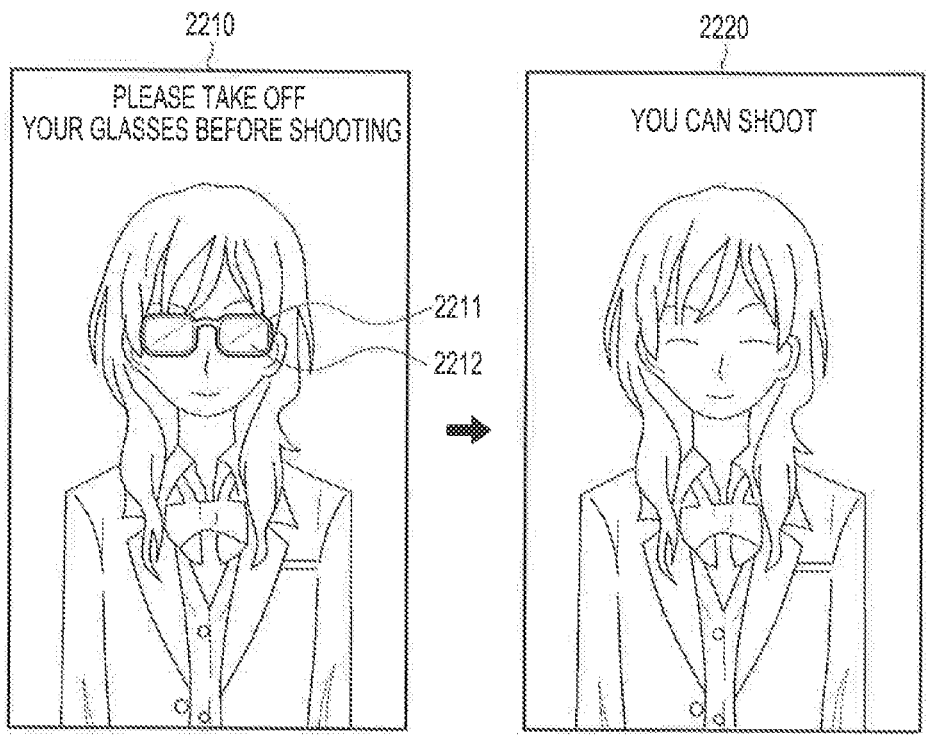
FIGS. 22A and 22B illustrate a shooting operation for a face analysis according to various embodiments of the present disclosure.
Figure 22B:
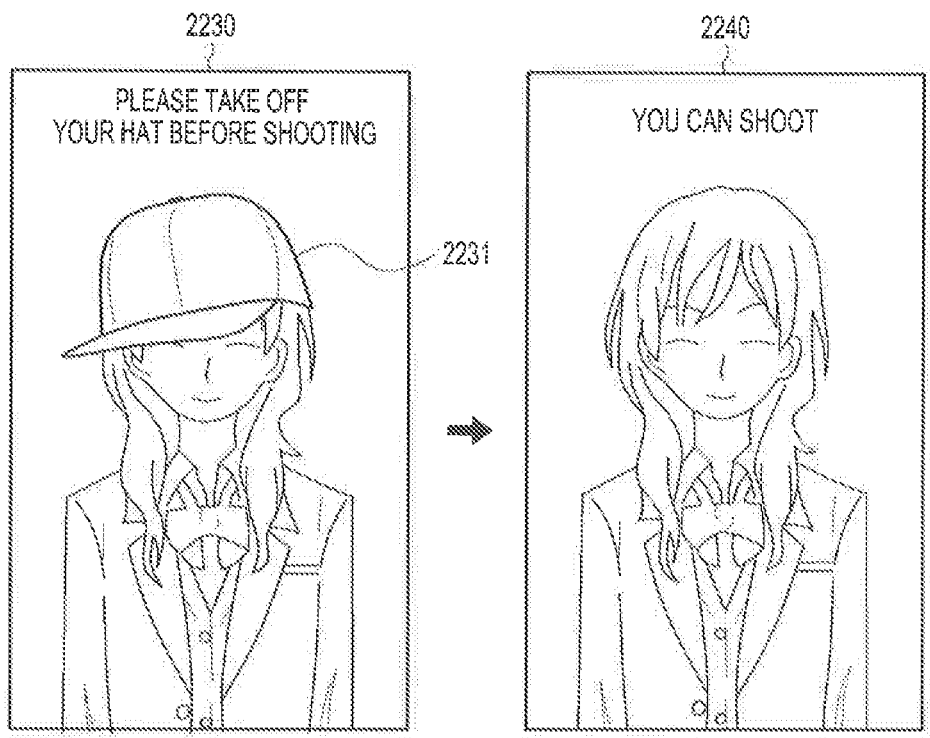

FIGS. 22A and 22B illustrate a shooting operation for a face analysis according to various embodiments of the present disclosure.

Referring to FIGS. 22A and 22B, according to various embodiments of the present disclosure, the electronic device may determine whether an accessory is worn in a face region being captured.

Referring to FIG. 22A, it is assumed that a high-school girl, whose face region is a shooting target, is wearing glasses.

According to various embodiments of the present disclosure, the electronic device may determine whether glasses are worn on the face region, depending on whether the face region being captured includes a line 2211 corresponding to the rim of the glasses, or a part 2212 indicating that the light is reflected on the glasses.

According to various embodiments of the present disclosure, if it is determined that the glasses are worn on the face region being captured, the electronic device may instruct the user or the high-school girl to take off the glasses. For example, the electronic device may display a wording, for example, "Please take off your glasses before shooting" in an image 2210 being captured.

At the sight of the wording, the user of the electronic device according to various embodiments of the present disclosure may take off the glasses. If the electronic device determines that the user has taken off the glasses, the electronic device may display a wording, for example, "You can shoot" in an image 2220 being captured.

Referring to FIG. 22B, it is assumed that a high-school girl, whose face region is a shooting target, is wearing a hat.

According to various embodiments of the present disclosure, the electronic device may determine whether a hat is worn on the face region, depending on whether the face region being captured includes a line 2231 corresponding to the shape of the hat.

According to various embodiments of the present disclosure, if it is determined that the hat is worn on the face region being captured, the electronic device may instruct the user or the high-school girl to take off the hat. For example, the electronic device may display a wording, for example, "Please take off your hat before shooting" in an image 2230 being captured.

At the sight of the wording, the user of the electronic device according to various embodiments of the present disclosure may take off the hat. If the electronic device determines that the user has taken off the hat, the electronic device may display a wording, for example, "You can shoot" in an image 2240 being captured.

Figure 23A:
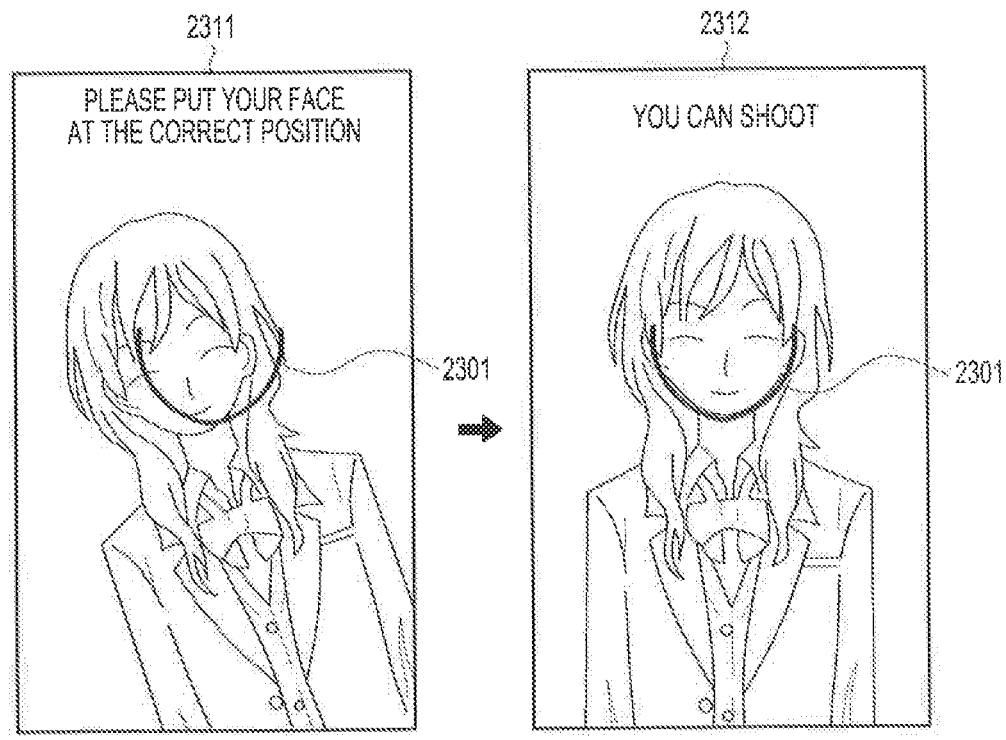
FIGS. 23A and 23B illustrate a shooting operation for a face analysis according to various embodiments of the present disclosure.
Figure 23B:
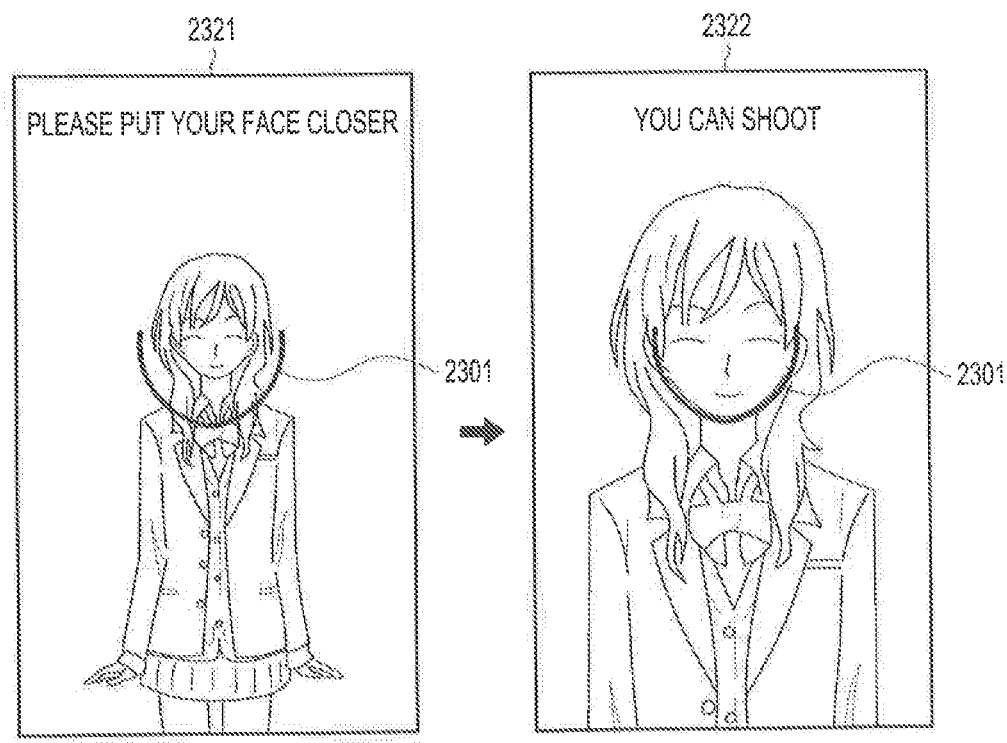

FIGS. 23A and 23B illustrate a shooting operation for a face analysis according to various embodiments of the present disclosure.

Referring to FIGS. 23A and 23B, according to various embodiments of the present disclosure, a line 2301 corresponding to the face region may be displayed on the electronic device so that the user may identify the direction or size of the face region being captured.

Referring to FIG. 23A, it is assumed that a high-school girl, whose face region is a shooting target, is shooting herself, with her face tilted.

According to various embodiments of the present disclosure, the electronic device may determine whether the face region is being captured at the correct position, depending on whether the face region being captured is out of the line 2301.

According to various embodiments of the present disclosure, if it is determined that the face region being captured is out of the line 2301, the electronic device may instruct the user or the high-school girl to put her face at the correct position. For example, the electronic device may display a wording, for example, "Please put your face at the correct position" in an image 2311 being captured.

At the sight of the wording, the user of the electronic device according to various embodiments of the present disclosure may put her face in line with the line 2301. If the electronic device determines that the user has put her face at the correct position, the electronic device may display a wording, for example, "You can shoot" in an image 2312 being captured.

Referring to FIG. 23B, it is assumed that a high-school girl, whose face region is a shooting target, is shooting herself at a distance.

According to various embodiments of the present disclosure, the electronic device may determine whether the face region is captured at a distance or at a close distance, depending on whether the size of the face region being captured matches the size of the line 2301.

According to various embodiments of the present disclosure, if it is determined that the face region being captured is captured at a distance since the size of the face region is smaller than the size of the line 2301, the electronic device may instruct the user or the high-school girl to put her face closer. For example, the electronic device may display a wording, for example, "Please put your face closer" in an image 2321 being captured.

At the sight of the wording, the user of the electronic device according to various embodiments of the present disclosure may put her face in line with the line 2301. If the electronic device determines that the user has put her face closer, the electronic device may display a wording, for example, "You can shoot" in an image 2322 being captured.

Figure 24:
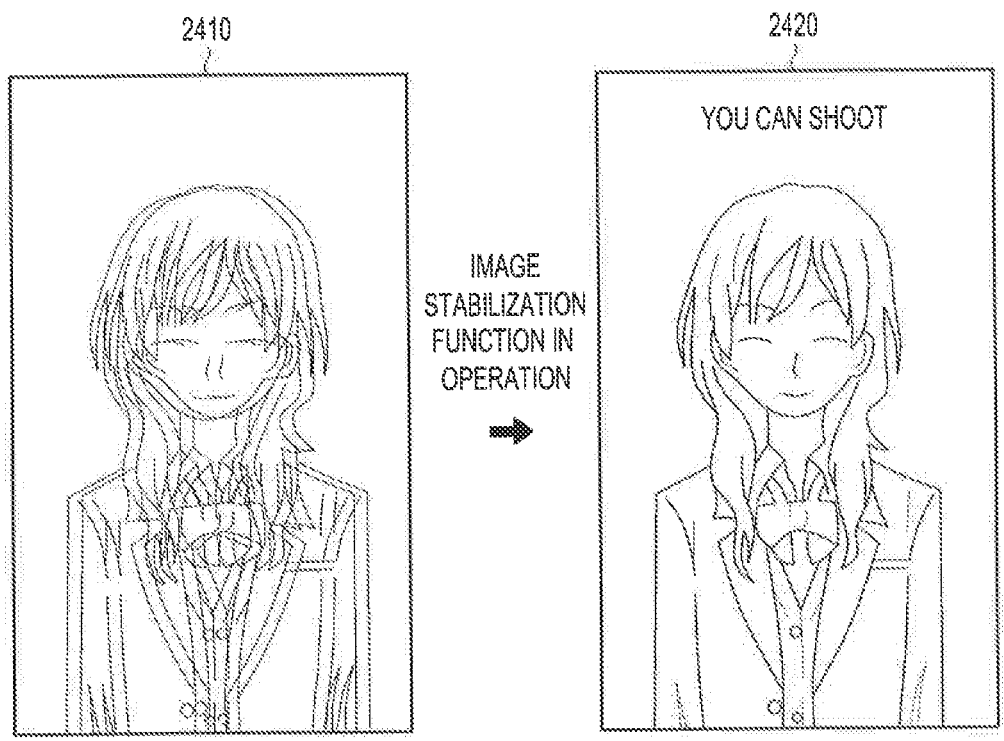
FIG. 24 illustrates a shooting operation for a face analysis according to various embodiments of the present disclosure.

FIG. 24 illustrates a shooting operation for a face analysis according to various embodiments of the present disclosure.

Referring to FIG. 24, it is assumed that an image 2410 is captured shaking in the electronic device.

According to various embodiments of the present disclosure, the electronic device may operate an image stabilization function, if the electronic device cannot identify the shape of the face region in the image being captured, or if the electronic device detects the shaking of the electronic device through the sensor, and the like. For example, the image stabilization function may include a function of preventing the image from being captured shaking, by adjusting the shutter speed or the aperture during image capturing.

According to various embodiments of the present disclosure, after the image stabilization function is set, the electronic device may display a wording, for example, "You can shoot" in an image 2420 being capture. For example, at the sight of the wording, the user may shoot her face.

Figure 25:
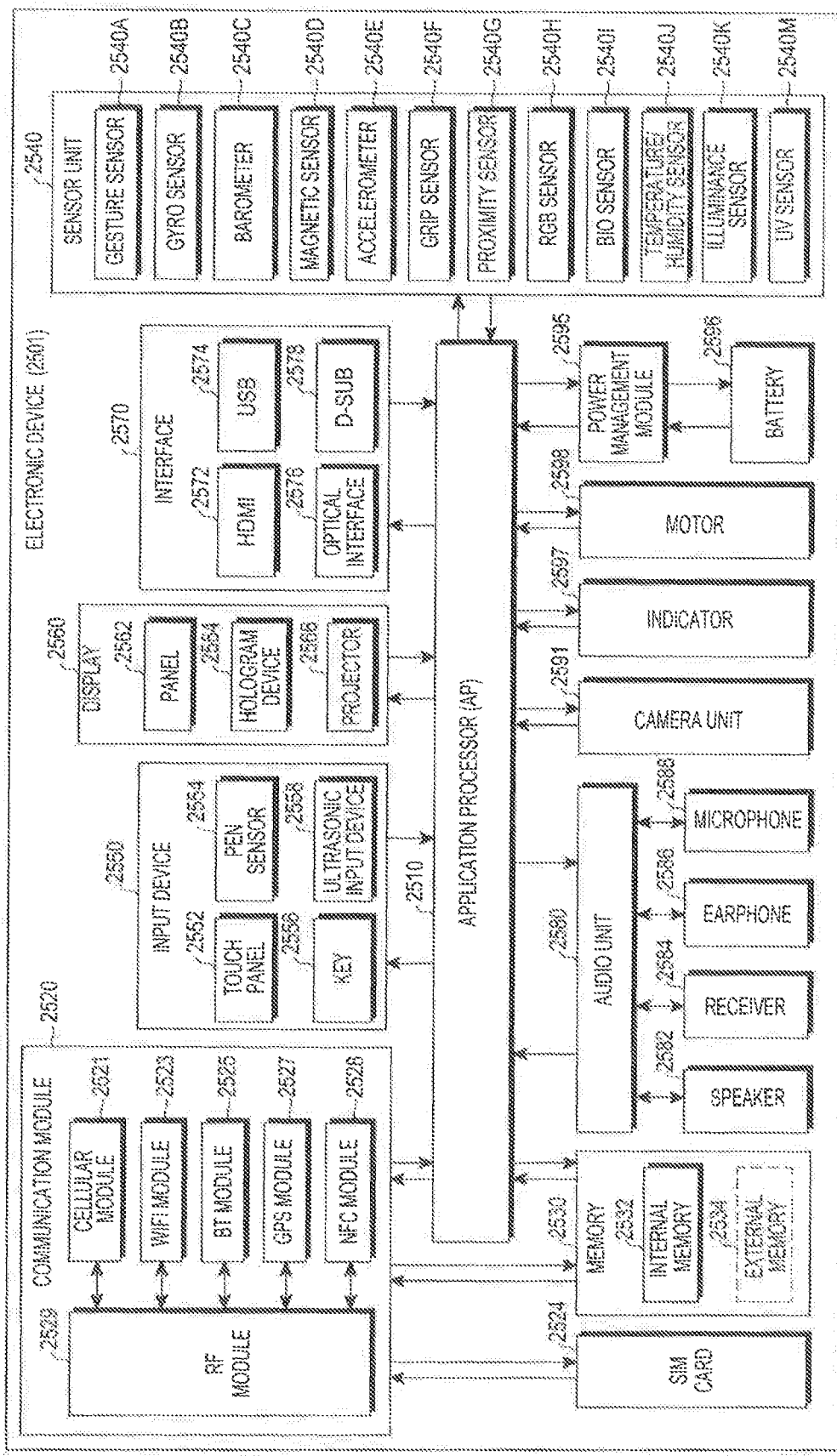
FIG. 25 is a block diagram illustrating a configuration of an electronic device according to various embodiments of the present disclosure.

FIG. 25 is a block diagram illustrating a configuration of an electronic device according to various embodiments of the present disclosure.

Referring to FIG. 25, an electronic device 2501 may constitute the whole or part of the electronic device 100 or 1901 shown in, for example, FIG. 1 or 19.

The electronic device 2501 may include at least one processor (e.g., an application processor (AP) 2510), a communication module 2520, a subscriber identification module (SIM) card 2524, a memory 2530, a sensor module 2540, an input device 2550, a display 2560, an interface 2570, an audio module 2580, a camera module 2591, a power management module 2595, a battery 2596, an indicator 2597, and a motor 2598.

The AP 2510 may control a plurality of hardware or software components connected to the AP 2510 by running the operating system or application program, and may process and calculate various data including multimedia data. The AP 2510 may be implemented as, for example, a system on chip (SoC). In one embodiment of the present disclosure, the AP 2510 may further include a graphics processing unit (GPU) (not shown).

The communication module 2520 (e.g., the communication interface 1960) may perform data transmission/reception in communication between the electronic device 2501 (e.g., the electronic device 100 or the electronic device 1901) and other electronic devices (e.g., the electronic device 1904 or the server 1906) connected to the electronic device 2501 over the network. In one embodiment of the present disclosure, the communication module 2520 may include a cellular module 2521, a Wi-Fi module 2523, a BT module 2525, a GPS module 2527, an NFC module 2528, and a radio frequency (RF) module 2529.

The cellular module 2521 may provide a voice call service, a video call service, a messaging service or an Internet service over a communication network (e.g., LTE, LTE-A, CDMA, WCDMA, UMTS, WiBro, GSM, and the like). Further, the cellular module 2521 may perform identification and authentication of an electronic device in the communication network by using, for example, a SIM (e.g., the SIM card 2524). In one embodiment of the present disclosure, the cellular module 2521 may perform at least some of the functions that can be provided by the AP 2510. For example, the cellular module 2521 may perform at least a part of the multimedia control function.

In an embodiment of the present disclosure, the cellular module 2521 may include a communication processor (CP). Further, the cellular module 2521 may be implemented as, for example, an SoC. Although the components, such as the cellular module 2521 (e.g., the CP), the memory 2530 or the power management module 2595 are shown as separate components from the AP 2510 in FIG. 25, the AP 2510 may be implemented to include at least some (e.g., the cellular module 2521) of the above-described components according to an embodiment of the present disclosure.

In an embodiment of the present disclosure, the AP 2510 or the cellular module 2521 (e.g., the CP) may load, on a volatile memory, the command or data that is received from at least one of a non-volatile memory or another component connected thereto, and process the loaded command or data. Further, the AP 2510 or the cellular module 2521 may store, in a non-volatile memory, the data that is received from or generated by at least one of other components.

Each of the Wi-Fi module 2523, the BT module 2525, the GPS module 2527 or the NFC module 2528 may include, for example, a processor for processing the data transmitted or received through the corresponding module. Although the cellular module 2521, the Wi-Fi module 2523, the BT module 2525, the GPS module 2527 or the NFC module 2528 are shown as their separate blocks in FIG. 25, at least some (e.g., two or more) of the cellular module 2521, the Wi-Fi module 2523, the BT module 2525, the GPS module 2527 or the NFC module 2528 may be included in one integrated chip (IC) or IC package according to an embodiment of the present disclosure. For example, at least some (e.g., a CP corresponding to the cellular module 2521 or a Wi-Fi processor corresponding to the Wi-Fi module 2523) of processors corresponding to the cellular module 2521, the Wi-Fi module 2523, the BT module 2525, the GPS module 2527 or the NFC module 2528 may be implemented as one SoC.

The RF module 2529 may perform transmission/reception of data, for example, transmission/reception of RF signals. The RF module 2529, although not shown, may include, for example, a transceiver, a power amplifier module (PAM), a frequency filter, a low noise amplifier (LNA), and the like. The RF module 2529 may further include the part (e.g., conductor or conducting wire) for transmitting and receiving electromagnetic waves in the free space in wireless communication. Although the cellular module 2521, the Wi-Fi module 2523, the BT module 2525, the GPS module 2527 and the NFC module 2528 are shown to share one RF module 2529 with each other in FIG. 25, at least one of the cellular module 2521, the Wi-Fi module 2523, the BT module 2525, the GPS module 2527 or the NFC module 2528 may perform transmission/reception of RF signals through a separate RF module according to an embodiment of the present disclosure.

The SIM card 2524 may be a card with a SIM, and may be inserted into a slot that is formed in a specific position of the electronic device. The SIM card 2524 may include unique identification information (e.g., integrated circuit card identifier (ICCID)) or subscriber information (e.g., international mobile subscriber identity (IMSI)).

The memory 2530 (e.g., the storage 150 or the memory 1930) may include an internal memory 2532 or an external memory 2534. The internal memory 2532 include at least one of, for example, a volatile memory (e.g., a dynamic random access memory (DRAM), a static RAM (SRAM), a synchronous dynamic RAM (SDRAM), and the like) or a non-volatile memory (e.g., a one time programmable read only memory (OTPROM), a programmable ROM (PROM), an erasable and programmable ROM (EPROM), an electrically erasable and programmable ROM (EEPROM), a mask ROM, a flash ROM, a NAND flash memory, a NOR flash memory, and the like).

In an embodiment of the present disclosure, the internal memory 2532 may be a solid state drive (SSD). The external memory 2534 may further include a flash drive, for example, compact flash (CF), secure digital (SD), micro-SD, mini-SD, extreme digital (xD), a memory stick, and the like. The external memory 2534 may be functionally connected to the electronic device 2501 through various interfaces. In one embodiment of the present disclosure, the electronic device 2501 may further include a storage device (or a storage medium), such as a hard drive.

The sensor module 2540 may measure the physical quantity or detect the operating status of the electronic device 2501, and convert the measured or detected information into an electrical signal. The sensor module 2540 may include at least one of, for example, a gesture sensor 2450A, a gyro sensor 2540B, a barometer 2540C, a magnetic sensor 2540D, an accelerometer 2540E, a grip sensor 2540F, a proximity sensor 2540G, a color sensor (e.g., red, green, blue (RGB) sensor) 2450H, a biosensor 2450I, a temperature/humidity sensor 2540J, an illuminance sensor 2540K, or a ultra violet (UV) sensor 2540M. Additionally or alternatively, the sensor module 2540 may include, for example, an E-nose sensor (not shown), an electromyography (EMG) sensor (not shown), an electroencephalogram (EEG) sensor (not shown), an electrocardiogram (ECG) sensor (not shown), an infrared (IR) sensor (not shown), an iris sensor (not shown), a fingerprint sensor (not shown), and the like. The sensor module 2540 may further include a control circuit for controlling at least one or more sensors belonging thereto.

The input device 2550 may include a touch panel 2552, a (digital) pen sensor 2554, a key 2556, or an ultrasonic input device 2558. The touch panel 2552 may recognize a touch input in at last one of, for example, capacitive, resistive, IR or ultrasonic manner. The touch panel 2552 may further include a control circuit. In the case of the capacitive scheme, the touch panel 2552 may recognize the physical contact or proximity. The touch panel 2552 may further include a tactile layer. In this case, the touch panel 2552 may provide a tactile or haptic feedback to the user.

The (digital) pen sensor 2554 may be implemented by using, for example, the method same as or similar to receiving a user's touch input, or a separate recognition sheet. The key 2556 may include, for example, a physical button, an optical key or a keypad. The ultrasonic input device 2558 is a device by which the electronic device 2501 can determine data by detecting sound waves with a microphone (e.g., a microphone 2588) through an input tool for generating an ultrasonic signal. The ultrasonic input device 2558 enables wireless recognition. In one embodiment of the present disclosure, the electronic device 2501 may receive a user input from the external device (e.g., a computer or a server) connected thereto using the communication module 2520.

The display 2560 (e.g., the display 140 or the display 1950) may include a panel 2562, a hologram device 2564, or a projector 2566. The panel 2562 may be, for example, a liquid-crystal display (LCD) panel or an active-matrix organic LED (AM-OLED) panel. The panel 2562 may be implemented to be, for example, flexible, transparent or wearable. The panel 2562, together with the touch panel 2552, may be implemented as one module. The hologram device 2564 may show stereoscopic images in the air using the interference of the light. The projector 2566 may display images by projecting the light on the screen. The screen may be disposed on the inside or outside of, for example, the electronic device 2501. In one embodiment of the present disclosure, the display 2560 may further include a control circuit for controlling the panel 2562, the hologram device 2564, or the projector 2566.

The interface 2570 may include, for example, an HDMI 2572, a USB 2574, an optical interface 2576 or D-subminiature (D-sub) 2578. The interface 2570 may be included in, for example, the communication interface 1960 shown in FIG. 19. Additionally or alternatively, the interface 2570 may include, for example, a mobile high-definition link (MHL) interface, a SD card/multi-media card (MMC) interface or an infrared data association (IrDA) interface.

The audio module 2580 may convert the sound and electrical signals bi-directionally. At least some components of the audio module 2580 may be included in, for example, the I/O interface 1940 shown in FIG. 19. The audio module 2580 may process the sound information that is received or output through, for example, a speaker 2582, a receiver 2584, an earphone 2586 or the microphone 2588.

The camera module 2591, which is a device capable of capturing still images and videos, may include one or more image sensors (e.g., a front image sensor or a rear image sensor), a lens (not shown), an image signal processor (ISP) (not shown), or a flash (not shown) (e.g., an LED or xenon lamp) according to an embodiment of the present disclosure.

The power management module 2595 may manage the power of the electronic device 2501. Although not shown, the power management module 2595 may include, for example, a power management integrated circuit (PMIC), a charger IC, or a battery or fuel gauge.

The PMIC may be mounted in, for example, an integrated circuit or an SoC semiconductor chip. A charging scheme may be divided into a wired charging scheme and a wireless charging scheme. The charger IC may charge a battery, and prevent the inflow of over voltage or over current from the charger. In one embodiment of the present disclosure, the charger IC may include a charger IC for at least one of the wired charging scheme or the wireless charging scheme. The wireless charging scheme may include, for example, a magnetic resonance scheme, a magnetic induction scheme, or an electromagnetic scheme. An additional circuit (e.g., a coil loop, a resonance circuit, a rectifier, and the like) for wireless charging may be added.

The battery or fuel gauge may measure, for example, the remaining capacity, charging voltage, charging current or temperature of the battery 2596. The battery 2596 may store or generate the electricity, and supply the power to the electronic device 2501 using the stored or generated electricity. The battery 2596 may include, for example, a rechargeable battery or a solar battery.

The indicator 2597 may indicate specific status (e.g., a boot status, a message status, a charging status, and the like) of the electronic device 2501 or a part (e.g., the AP 2510) thereof. The motor 2598 may convert an electrical signal into mechanical vibrations. Although not shown, the electronic device 2501 may include a processing device (e.g., a GPU) for mobile TV support. The processing device for mobile TV support may process media data based on the standards, such as, for example, digital multimedia broadcasting (DMB), digital video broadcasting (DVB), or mediaFLO, and the like.

Each of above-described components of the electronic device according to various embodiments of the present disclosure may be configured with one or more components, and names of the components may vary depending on the type of the electronic device. The electronic device according to various embodiments of the present disclosure may include at least one of the above-described components, some of which may be omitted, or may further include additional other components. Further, some of the components of the electronic device according to various embodiments of the present disclosure may be configured as one entity by being combined, thereby performing the previous functions of the components in the same manner.

The term 'module' used in various embodiments of the present disclosure may refer to a unit that includes, for example, one or a combination of hardware, software or firmware. The term 'module' may be interchangeably used with terms, such as, for example, unit, logic, logical block, component, or circuit. The module may be the minimum unit of an integrally constructed part or a part thereof. The module may be the minimum unit for performing one or more functions, or a part thereof. The module may be implemented mechanically or electronically. For example, the module according to various embodiments of the present disclosure may include at least one of an application-specific integrated circuit (ASIC) chip, field-programmable gate arrays (FPGAs), or a programmable-logic device, which are known or will be developed in the future, and which perform certain operations.

At least a part of the device (e.g., modules or functions thereof) or method (e.g., operations) according to various embodiments of the present disclosure may be implemented by a command that is stored in computer-readable storage media in the form of, for example, a programming module. If the command is executed by one or more processors (e.g., the controller 110 or the processor 1920), the one or more processors may perform a function corresponding to the command. The computer-readable storage media may be, for example, the storage 150 or the memory 1930. At least a part of the programming module may be implemented (e.g., executed) by, for example, the controller 110 or the processor 1920. At least a part of the programming module may include, for example, a module, a program, a routine, a set of instructions, or a processor for performing one or more functions.

Certain aspects of the present disclosure can also be embodied as computer readable code on a non-transitory computer readable recording medium. A non-transitory computer readable recording medium is any data storage device that can store data which can be thereafter read by a computer system. Examples of the non-transitory computer readable recording medium include a Read-Only Memory (ROM), a Random-Access Memory (RAM), Compact DiscROMs (CD-ROMs), magnetic tapes, floppy disks, and optical data storage devices. The non-transitory computer readable recording medium can also be distributed over network coupled computer systems so that the computer readable code is stored and executed in a distributed fashion. In addition, functional programs, code, and code segments for accomplishing the present disclosure can be easily construed by programmers skilled in the art to which the present disclosure pertains.

At this point it should be noted that the various embodiments of the present disclosure as described above typically involve the processing of input data and the generation of output data to some extent. This input data processing and output data generation may be implemented in hardware or software in combination with hardware. For example, specific electronic components may be employed in a mobile device or similar or related circuitry for implementing the functions associated with the various embodiments of the present disclosure as described above. Alternatively, one or more processors operating in accordance with stored instructions may implement the functions associated with the various embodiments of the present disclosure as described above. If such is the case, it is within the scope of the present disclosure that such instructions may be stored on one or more non-transitory processor readable mediums. Examples of the processor readable mediums include a ROM, a RAM, CD-ROMs, magnetic tapes, floppy disks, and optical data storage devices. The processor readable mediums can also be distributed over network coupled computer systems so that the instructions are stored and executed in a distributed fashion. In addition, functional computer programs, instructions, and instruction segments for accomplishing the present disclosure can be easily construed by programmers skilled in the art to which the present disclosure pertains.

A module or a programming module according to various embodiments of the present disclosure may include at least one of the above-described components, some of which may be omitted, or may further include additional other components. Operations performed by a module, a programming module or other components according to various embodiments of the present disclosure may be performed in a sequential, parallel, iterative or heuristic way. Some operations may be performed in a different order or omitted, or other operations may be added.

According to various embodiments of the present disclosure, in a storage medium storing instructions, when the instructions are executed by at least one processor, the instructions are set to allow the at least one processor to perform at least one operation. The at least one operation may include an operation of detecting at least one face region from an image that is being captured by a camera module, an operation of zooming in the at least one detected face region, and an operation of analyzing the zoomed in face region according to at least one analysis item.

According to various embodiments of the present disclosure, the at least one operation may include an operation of detecting a face region from at least one stored image, and an operation of analyzing the at least one detected face region according to at least one analysis item.

According to various embodiments of the present disclosure, the operation of analyzing face information may be performed based on a previously stored image. For example, the stored image may be an image that was captured in a preset distance or at a preset angle according to a preset fixed focus value. If a user's face is in a position corresponding to the set distance or angle, the electronic device may capture a face image, or display a screen for requesting the user to capture a face region to correspond to the distance or angle.

According to various embodiments of the present disclosure, the stored image may be captured and stored in a predetermined situation so that the user may not execute the shooting operation. For example, in a situation where the user watches the electronic device for a predetermined time or more (e.g., the user determines the web browser, or views a media file (e.g., video)), or in a situation where the electronic device is located at an angle at which the electronic device can capture the user's face image (e.g., in a situation where the electronic device can capture the user's face in the front direction depending on the angle of the front camera), the electronic device may capture the user's face image by operating the camera module in the background.

According to various embodiments of the present disclosure, the electronic device may determine a stored image, remove, from the image, the portions (e.g., shadows or hairs), analysis of which is unnecessary, and set at least one reference point in the region where the unnecessary portions are removed, thereby to determine the face region. For example, the reference point may be set on the entire face region in the image, and may be set based on the pre-analyzed data base or the previously analyzed specific user's face image so that each face region (e.g., a C zone, an M zone, a U zone, eyes, nose, cheeks, mouth, and the like) may be identified.

According to various embodiments of the present disclosure, upon identifying a face region in a previously stored image, the electronic device may output the result of analyzing skin conditions of each region through an analysis result screen.

According to various embodiments of the present disclosure, an operation of analyzing face information may be performed based on the previously stored image. For example, the electronic device may set at least one reference point on an image, and determine a face region based on the set reference point.

According to various embodiments of the present disclosure, upon determining a face region in a previously stored image, the electronic device may output the result of analyzing skin conditions of each region through an analysis result screen.

Figure 26:
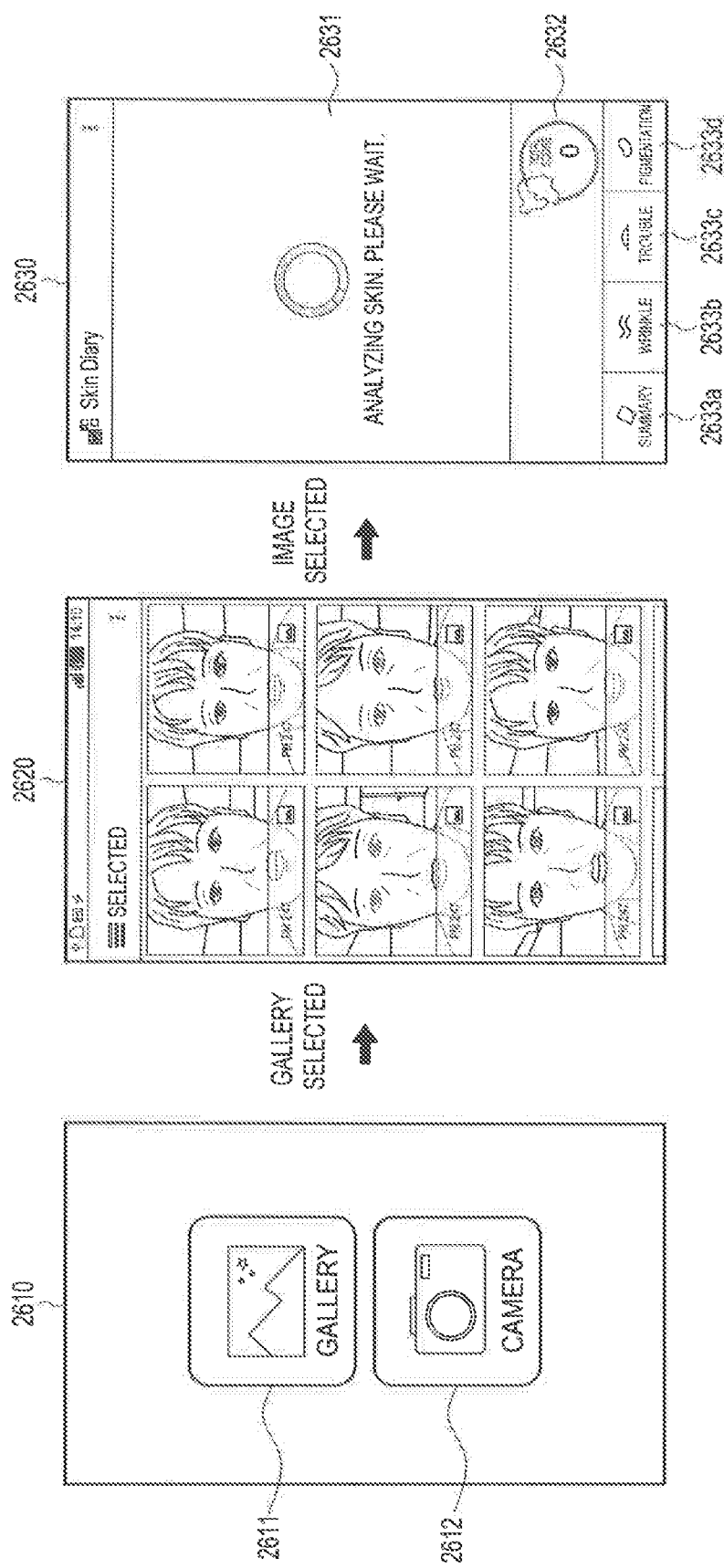
FIG. 26 illustrates a screen of an application for analyzing face information based on a stored image according to various embodiments of the present disclosure.

FIG. 26 illustrates a screen of an application for analyzing face information based on a stored image according to various embodiments of the present disclosure.

Referring to FIG. 26, if an application for analyzing face information is run, an execution screen 2610 may include a Gallery button 2611 for running a gallery application for displaying images stored in the electronic device, or a Camera button 2612 for enabling the camera module to switch to a screen for capturing an image.

According to various embodiments of the present disclosure, the images that are displayed as the Gallery button 2611 is selected may include a selection item by which the user may select the images, or may include filtered images, face information of which can be analyzed, among the images stored in the electronic device. The images, face information of which can be analyzed, may be images in which the face region is captured to correspond to a predetermined angle or size.

According to various embodiments of the present disclosure, if the Gallery button 2611 is selected, an image selection screen 2620 may be displayed, on which the user can select at least one image, face information of which is to be analyzed. For example, the images displayed on the image selection screen 2620 may be arranged in the last captured or stored order.

According to various embodiments of the present disclosure, if the user selects at least one of the images included in the image selection screen 2620 as an image whose face information is to be analyzed, an analysis result screen 2630 for displaying the result of analyzing the selected images may be displayed.

According to various embodiments of the present disclosure, the analysis result screen 2630 may include a region 2631 in which the result of analyzing face information is displayed in the image, a region 2632 in which the result of analyzing face information is displayed numerically or in a graph, or buttons by which the user can select the analysis results for each analysis item, and may also include various other items related to face analysis. For example, the buttons by which the user can select the analysis results for each analysis item may include a Summary button 2633a for displaying the analysis results for the entire face region, a Wrinkle button 2633b for displaying the analysis results for wrinkles, a Trouble button 2633c for displaying the analysis results for skin troubles, or a Pigmentation button 2633d for displaying the analysis results for pigmentation, and may also include other selection items for displaying the analysis results for various other analysis items.

Figure 27:
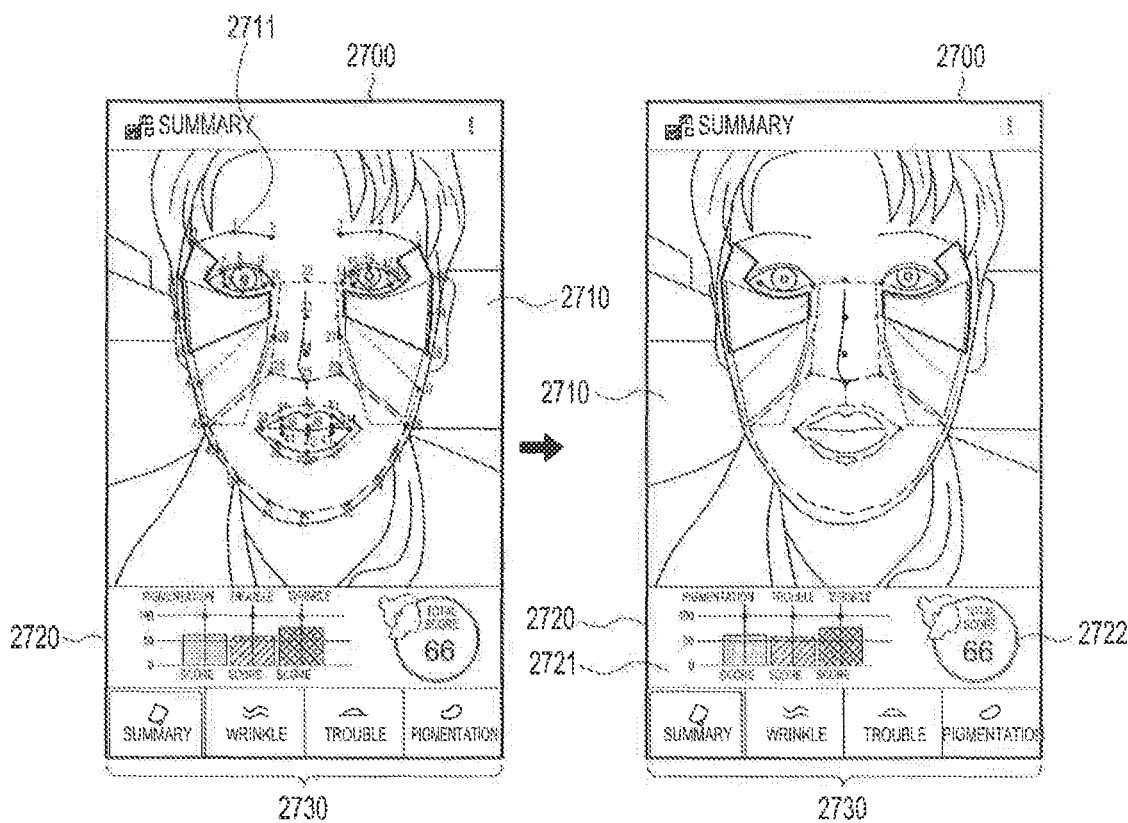
FIGS. 27, 28, 29, 30, 31, 32, 33, 34, and 35 illustrate a screen showing the face analysis results according to various embodiments of the present disclosure.

FIG. 27 illustrates a screen showing face analysis results according to various embodiments of the present disclosure.

Referring to FIG. 27, an analysis result screen 2700 may include an image region 2710 in which the analyzed face region is displayed, an analysis result region 2720 in which the analysis results are displayed, or an analysis item selection region 2730 for selecting the analysis results for each analysis item.

In the image region 2710, a face region may be detected from an image stored in the electronic device and at least one reference point 2711 may be set in the detected face region. Based on the at least one reference point 2711, a face region (e.g., 2712, 2713, 2714, 2715, or 2716) to be analyzed may be set according to at least one analysis item. The region 2712 may include a region of outer parts of both eyes as a C zone. The region 2713 may include a nose region, the region 2714 may include a cheek region, the region 2715 may include a region around the nose, and the region 2716 may include a region around the mouth.

According to various embodiments of the present disclosure, each of the face regions may be selected as a user input (e.g., a touch gesture) is made, and as for the selected face region, a screen obtained by analyzing the face region may be zoomed in and displayed.

In the analysis result region 2720, the result of analyzing the skin conditions may be displayed numerically (e.g., may be displayed in the state of a score 2722 or a graph 2721). For example, the graph 2721 may represent the score of the skin conditions for each analysis item by analyzing a specific face region for each analysis item. The score 2722 may be a value obtained by averaging a score of each analysis item for a specific face region, and as the score 2722 is higher, the skin conditions may be better.

The analysis item selection region 2730 may include at least one button for displaying the analysis results of each analysis item, and depending on the selected button, the analysis results for a specific face region may be displayed in the image region 2710 or the analysis result region 2720. For example, if the Summary button is selected, the entire face region may be displayed in the image region 2710, and the analysis results for the entire face region may be displayed in the analysis result region 2720.

Figure 28:
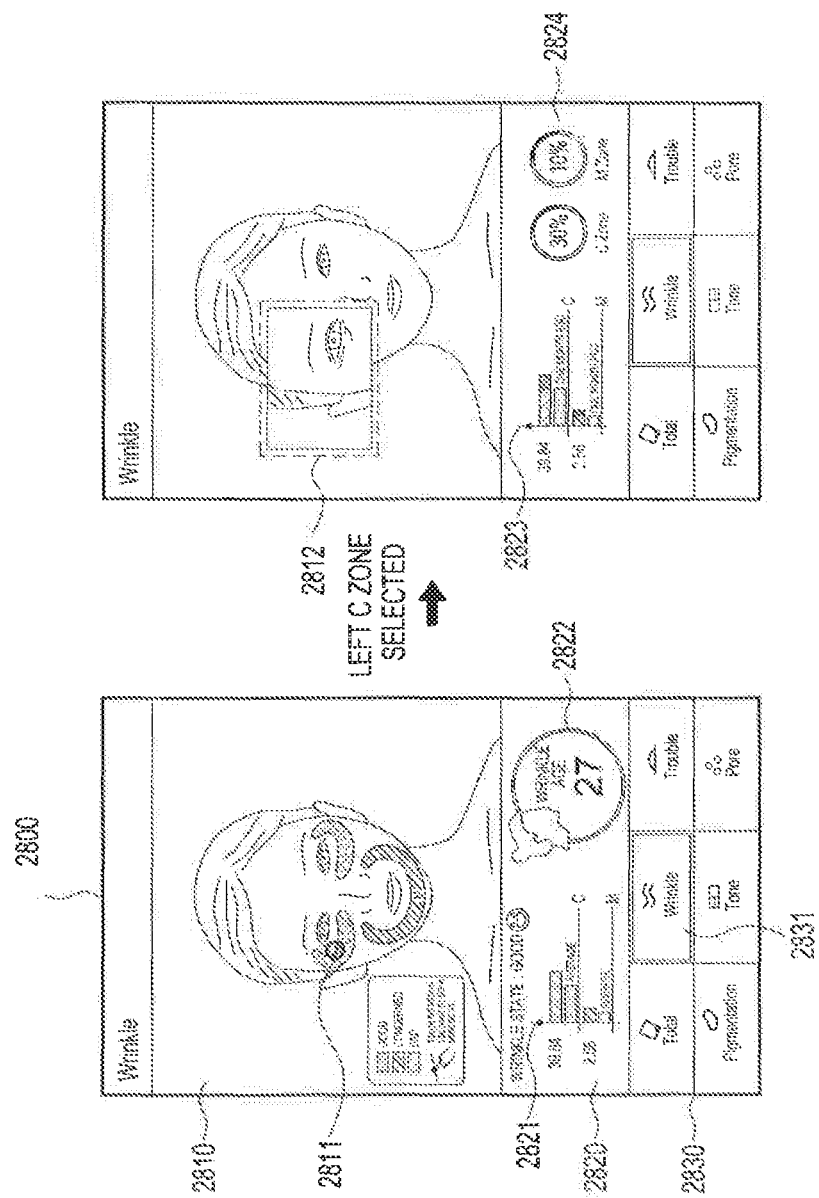

FIG. 28 illustrates a screen showing face analysis results according to various embodiments of the present disclosure.

Referring to FIG. 28, an analysis result screen 2800 may include an image region 2810 in which at least one of analyzed face regions can be selected, an analysis result region 2820, or an analysis item selection region 2830.

According to various embodiments of the present disclosure, if a Wrinkle button 2831 is selected in the analysis item selection region 2830, the result of analyzing wrinkles among various analysis items may be displayed in the image region 2810 or the analysis result region 2820.

In the image region 2810, based on the images stored in the electronic device, the result of analyzing wrinkles in at least one face region (e.g., a region of the C zone or U zone) may be displayed in an image. For example, since each face region is displayed in a different color depending on the skin conditions, the user may determine the skin conditions based on the displayed skin color.

In the analysis result region 2820, a graph 2821 obtained by comparing the result of analyzing wrinkles with an average score for each of the C zone or M zone, or a score 2822 for wrinkles in the entire face region may be displayed.

According to various embodiments of the present disclosure, if the user makes a user input 2811 in a specific region (e.g., a left C-zone region) to determine the analysis results, a zoomed in screen 2812 may be displayed, on which the region (e.g., the left C-zone region) where the user input is made, is analyzed.

According to various embodiments of the present disclosure, the analysis result region 2820 may provide the history of a change in wrinkles for the entire face region. For example, the analysis result region 2820 may include a graph 2823 obtained by comparing the wrinkle state measured one month ago with the currently measured wrinkle state, or a graph 2824 indicating how much the wrinkle state of the C zone or M zone has been improved than before.

Figure 29:
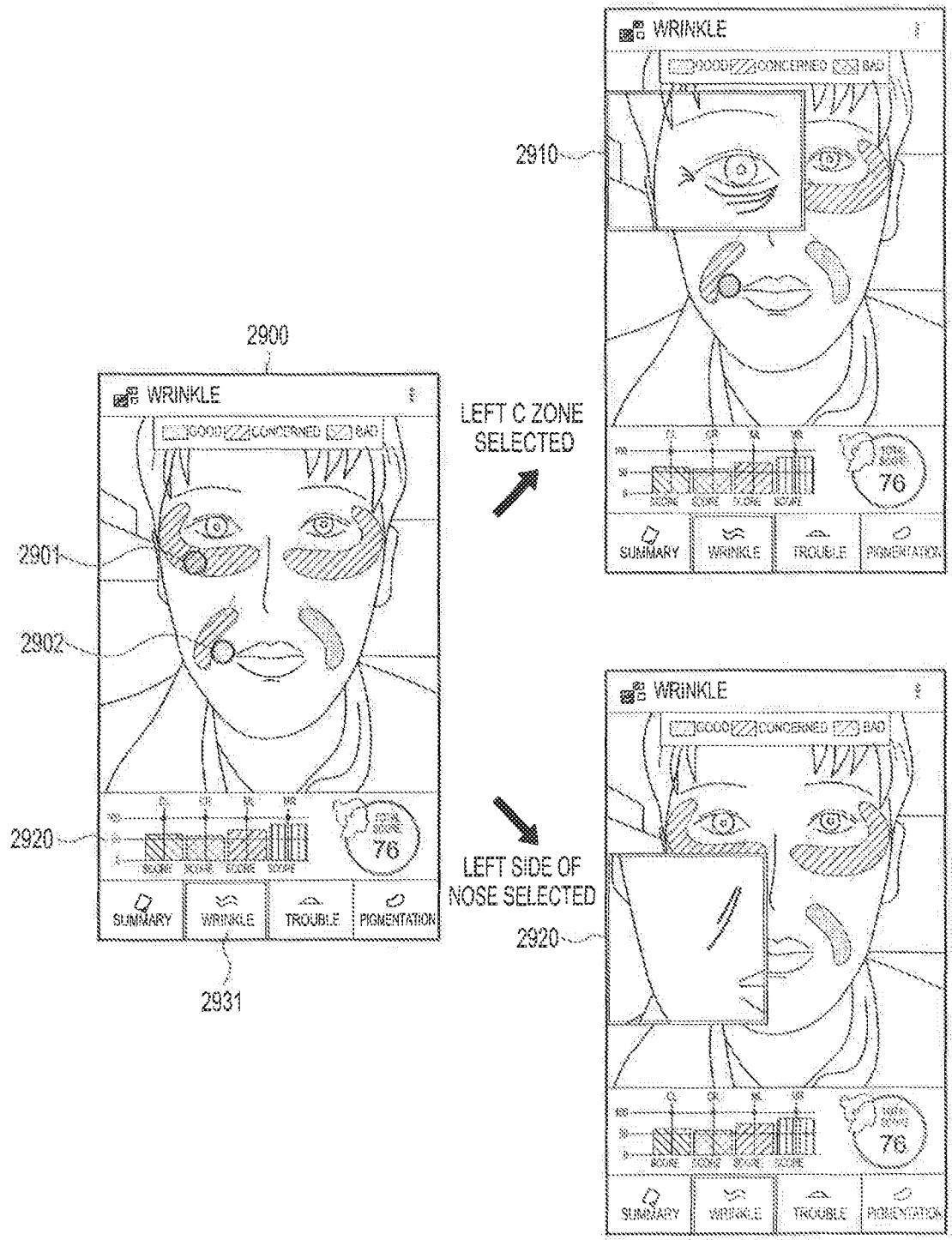

FIG. 29 illustrates a screen showing face analysis results according to various embodiments of the present disclosure.

Referring to FIG. 29, the user has selected a Wrinkle button 2931 in the analysis item selection region. Accordingly, an analysis result screen 2900 may include an image obtained by analyzing the wrinkles, or an analysis result region 2920.

In the analysis result region 2920, the wrinkle state for each of specific regions (e.g., the left CL or right CR of the C zone, or the left ML or right MR of the M zone) or the wrinkle state in the entire face region may be displayed in score.

According to various embodiments of the present disclosure, the user may select a region where the user desires to determine the zoomed in or detailed screen among the analyzed face regions. For example, if the left C-zone region is selected by a user input 2901, a screen 2910 may be displayed, on which the left region of the C zone is zoomed in the face. If the left region of the nose is selected by a user input 2902, a screen 2920 may be displayed, on which the left region of the nose is zoomed in the face.

Figure 30:
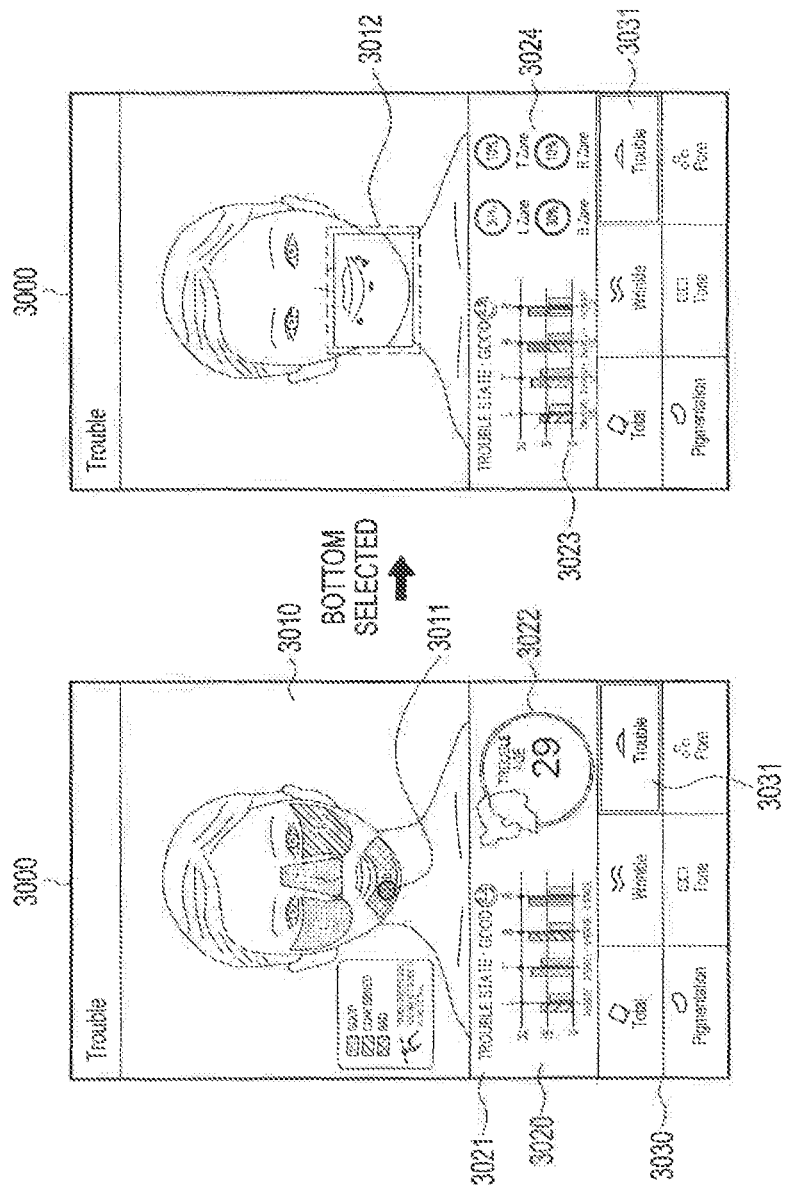

FIG. 30 illustrates a screen showing face analysis results according to various embodiments of the present disclosure.

Referring to FIG. 30, if the user selects a Trouble button 3031 in an analysis item selection region 3030 of an analysis result screen 3000, the result of analyzing troubles among various analysis items may be displayed in an image region 3010 or an analysis result region 3020 of the analysis result screen 3000.

In the image region 3010, based on the images stored in the electronic device, the result of analyzing at least one face region (e.g., a right region R, a left region L, a top region T or a bottom region B) analyzed for troubles may be displayed in an image. For example, since each face region is displayed in a different color depending on the skin conditions, the user may determine the skin conditions of the face region based on the displayed skin color.

In the analysis result region 3020, a graph 3021 obtained by comparing the result of analyzing troubles with an average score for each of the right region R, the left region L, the top region T or the bottom region B, or a score 3022 for troubles in the entire face region may be displayed.

According to various embodiments of the present disclosure, if the bottom of the face is selected by a user input 3011, a zoomed in screen 3012 may be displayed, on which the bottom region is analyzed. For example, based on the zoomed in screen 3012, the user may determine the position and size of the troubles in the bottom region.

According to various embodiments of the present disclosure, the analysis result region 3020 may provide the history of a change in troubles for the entire face region. For example, the analysis result region 3020 may include a graph 3023 obtained by comparing the trouble state measured one month ago with the currently measured trouble state, or a graph 3024 indicating how much the trouble state of each region (e.g., the right region R, the left region L, the top region T or the bottom region B) has been improved than before.

Figure 31:
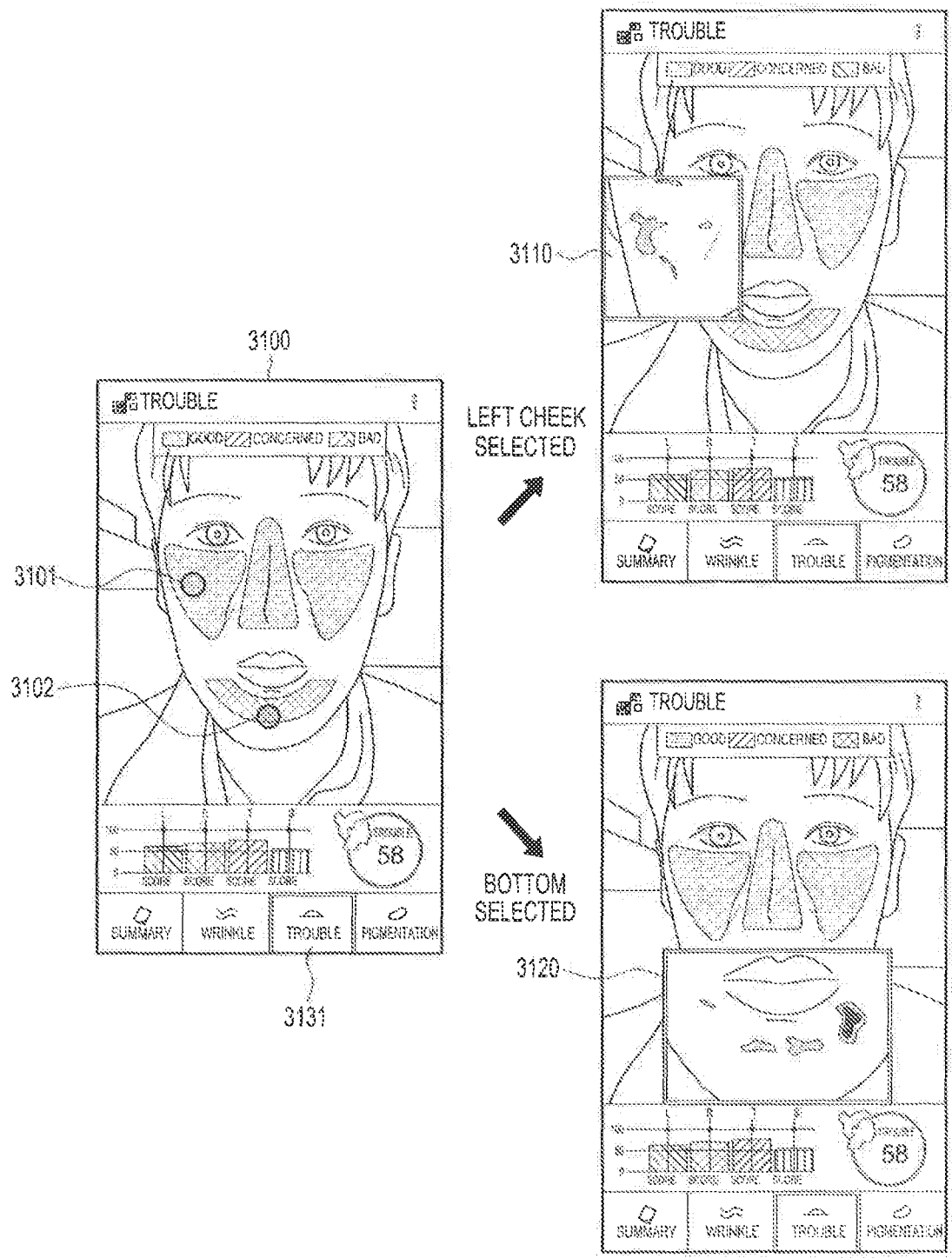

FIG. 31 illustrates a screen showing face analysis results according to various embodiments of the present disclosure.

Referring to FIG. 31, the user has selected a Trouble button 3131 in the analysis item selection region. Accordingly, an analysis result screen 3100 may include an image obtained by analyzing the troubles, or an analysis result region 3120.

According to various embodiments of the present disclosure, the user may select a region where the user desires to determine the zoomed in or detailed screen among the analyzed face regions. For example, if the left cheek region is selected by a user input 3101, a screen 3110 may be displayed, on which the left cheek of the face is zoomed in. If the bottom is selected by a user input 3102, a screen 3120 may be displayed, on which the bottom of the face is zoomed in.

Figure 32:
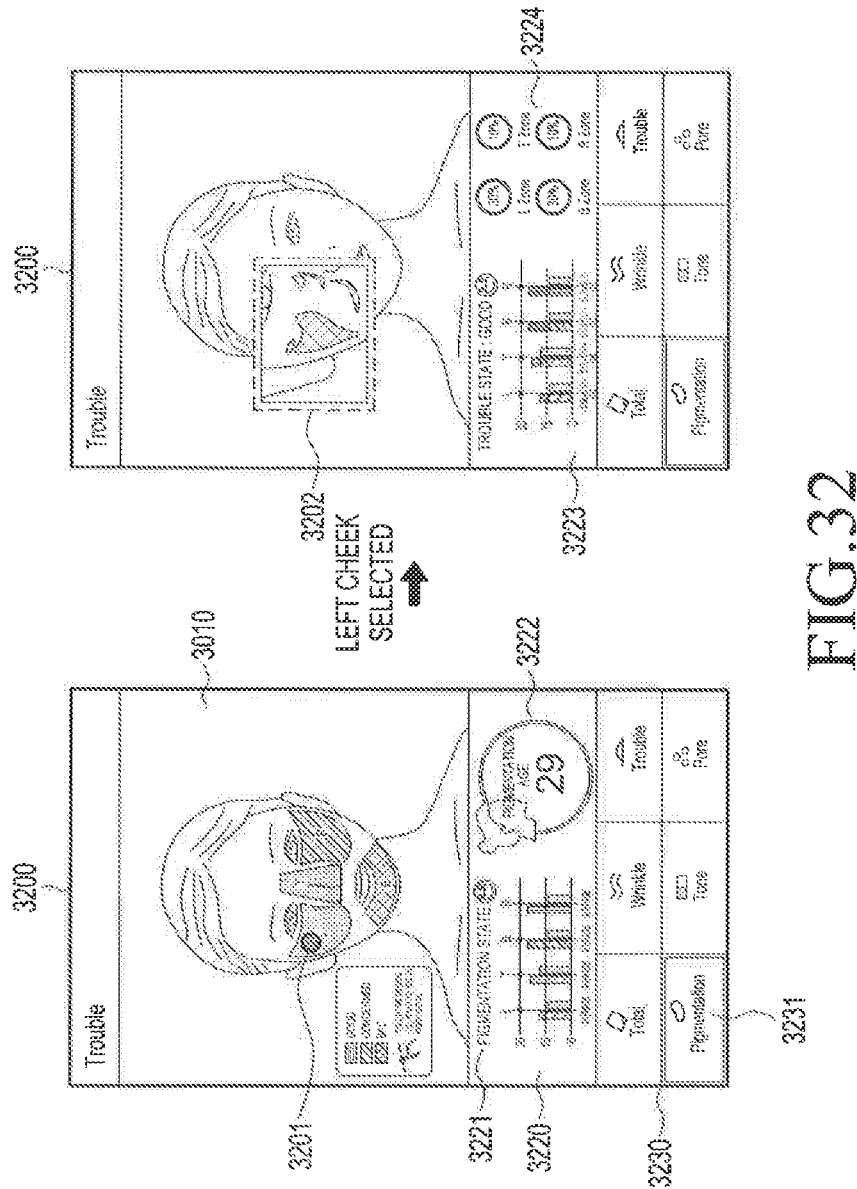

FIG. 32 illustrates a screen showing face analysis results according to various embodiments of the present disclosure.

Referring to FIG. 32, if the user selects a Pigmentation button 3231 in an analysis item selection region 3230 of an analysis result screen 3200, the result of analyzing the pigmentation among various analysis items may be displayed in an image region 3210 or an analysis result region 3220 of the analysis result screen 3200.

In the image region 3210, based on the images stored in the electronic device, the result of analyzing at least one face region (e.g., the right region R, the left region L, the top region T or the bottom region B) analyzed for pigmentation may be displayed in an image. For example, since each face region is displayed in a different color depending on the skin conditions, the user may determine the skin conditions of the face region based on the displayed skin color.

In the analysis result region 3220, a graph 3221 obtained by comparing the result of analyzing the pigmentation with an average score for each of the right region R, the left region L, the top region T or the bottom region B, or a score 3222 for pigmentation in entire face region may be displayed.

According to various embodiments of the present disclosure, if the left cheek is selected by a user input 3201, a zoomed in screen 3202 may be displayed, on which the left cheek region is analyzed. For example, based on the zoomed in screen 3202, the user may determine the position and size of the pigmentation spots in the left cheek region.

According to various embodiments of the present disclosure, the analysis result region 3220 may provide the history of a change in pigmentation for the entire face region. For example, the analysis result region 3220 may include a graph 3223 obtained by comparing the pigmentation state measured one month ago with the currently measured pigmentation state, or a graph 3224 indicating how much the pigmentation state of each region (e.g., the right region R, the left region L, the top region T or the bottom region B) has been improved than before.

Figure 33:
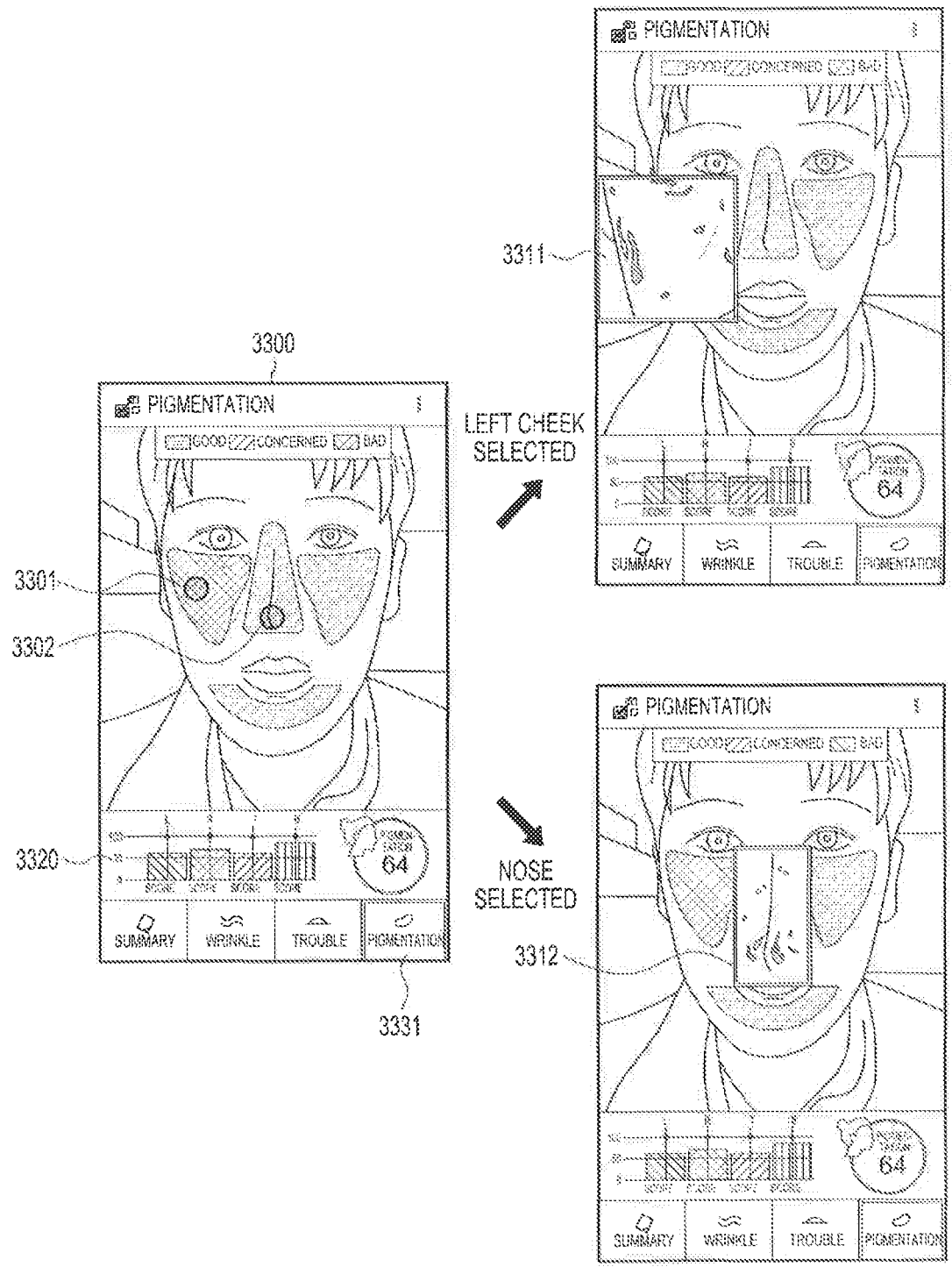

FIG. 33 illustrates a screen showing face analysis results according to various embodiments of the present disclosure.

Referring to FIG. 33, the user has selected a Pigmentation button 3331 in the analysis item selection region. Accordingly, an analysis result screen 3300 may include an image obtained by analyzing the pigmentation, or an analysis result region 3320.

According to various embodiments of the present disclosure, the user may select a region where the user desires to determine the zoomed in or detailed screen among the analyzed face regions. For example, if the left cheek region is selected by a user input 3301, a screen 3311 may be displayed, on which the left cheek of the face is zoomed in. If the nose region is selected by a user input 3302, a screen 3312 may be displayed, on which the nose region is zoomed in.

Figure 34:
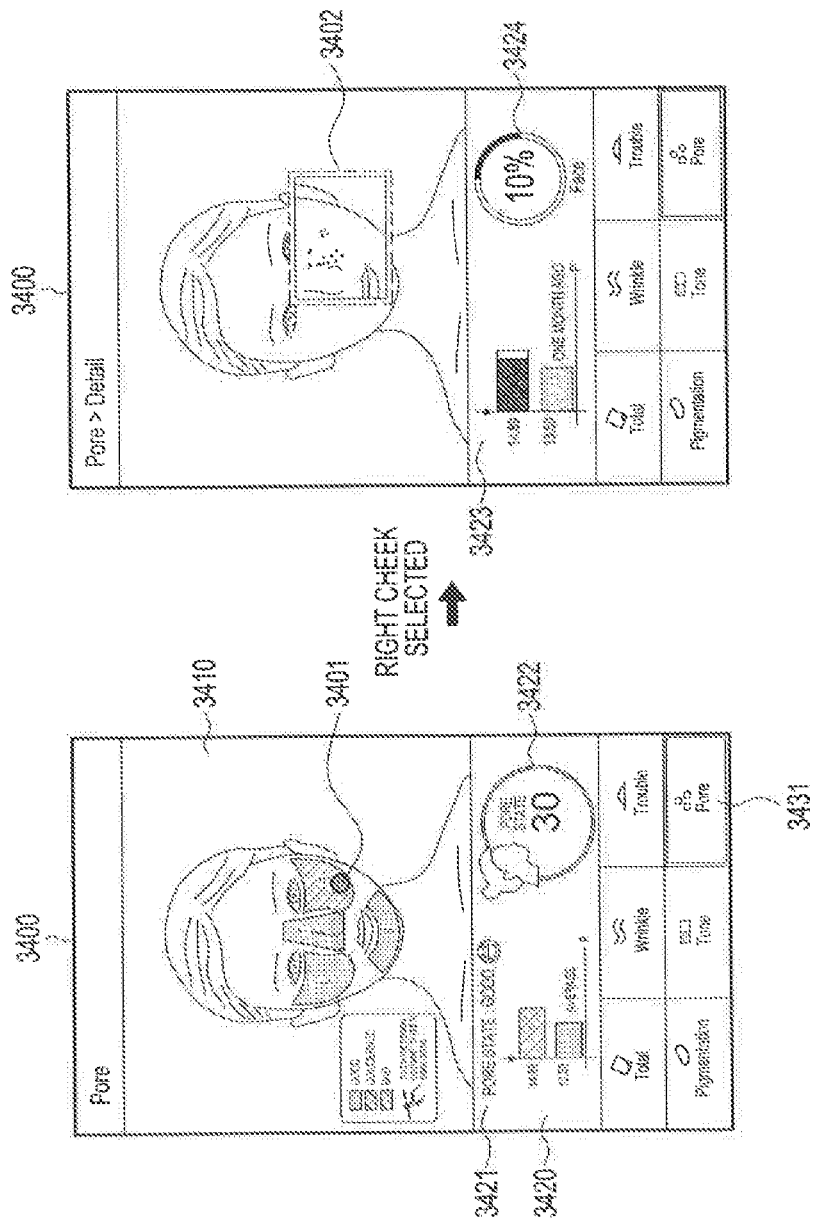

FIG. 34 illustrates a screen showing face analysis results according to various embodiments of the present disclosure.

Referring to FIG. 34, if the user selects a Pore button 3431 in an analysis item selection region 3430 of an analysis result screen 3400, the result of analyzing the pores among various analysis items may be displayed in an image region 3410 or an analysis result region 3420 of the analysis result screen 3400.

In the image region 3410, based on the images stored in the electronic device, the result of analyzing at least one face region (e.g., the right region R, the left region L, the top region T or the bottom region B) analyzed for pores may be displayed in an image. For example, since each face region is displayed in a different color depending on the skin conditions, the user may determine the skin conditions of the face region based on the displayed skin color.

In the analysis result region 3420, a graph 3421 obtained by comparing the result of analyzing the pores with an average score for each of the right region R, the left region L, the top region T or the bottom region B, or a score 3422 for pores in the entire face region may be displayed.

According to various embodiments of the present disclosure, if the right cheek is selected by a user input 3401, a zoomed in screen 3402 may be displayed, on which the right cheek region of the face is analyzed. For example, based on the zoomed in screen 3402, the user may determine the position and size of the pores in the right cheek region.

According to various embodiments of the present disclosure, the analysis result region 3420 may provide the history of a change in pores for the entire face region. For example, the analysis result region 3420 may include a graph 3423 obtained by comparing the pore state measured one month ago with the currently measured pore state, or a graph 3424 indicating how much the pore state of the entire face region has been improved than before.

Figure 35:
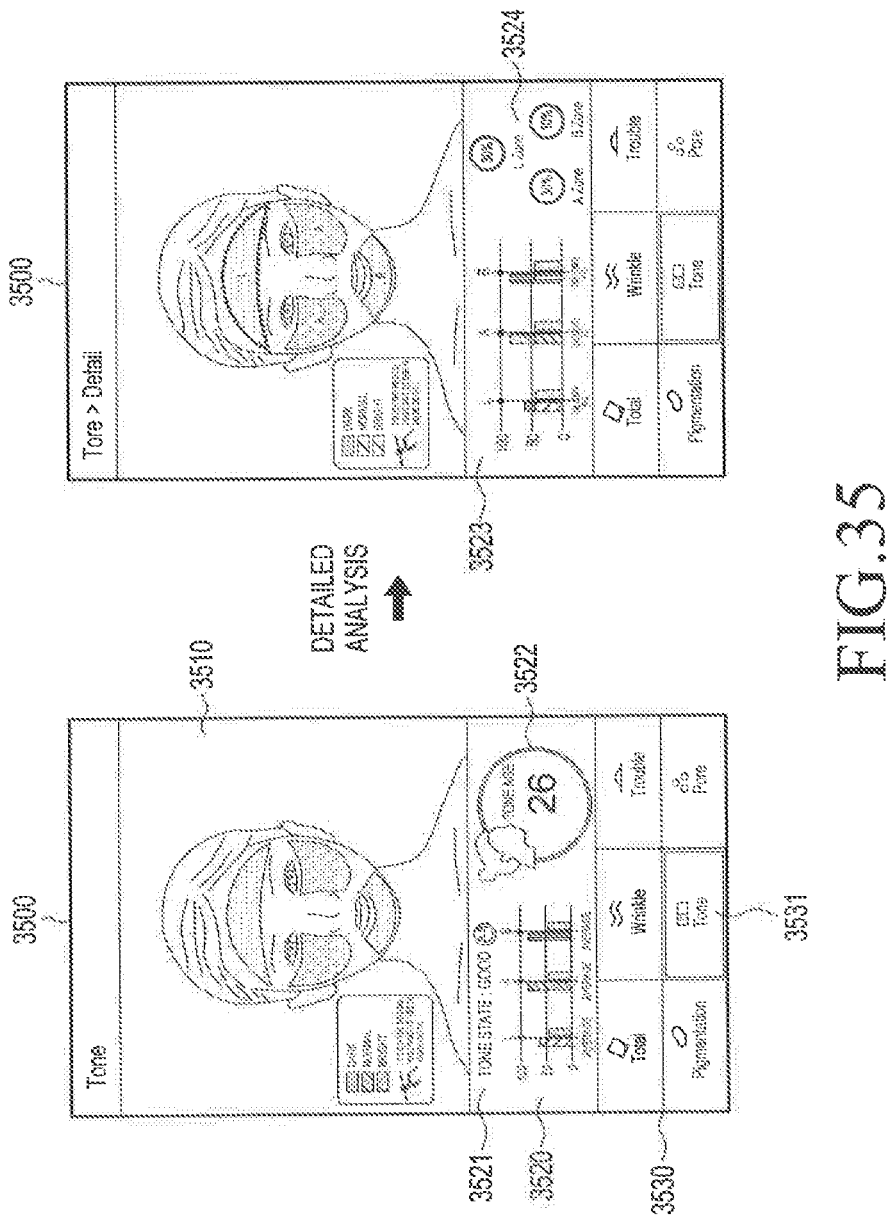

FIG. 35 illustrates a screen showing face analysis results according to various embodiments of the present disclosure.

Referring to FIG. 35, if the user selects a Tone button 3531 in an analysis item selection region 3530 of an analysis result screen 3500, the result of analyzing skin tones among various analysis items may be displayed in an image region 3510 or an analysis result region 3520 of the analysis result screen 3500.

In the image region 3510, based on the images stored in the electronic device, the result of analyzing at least one face region (e.g., a brow region L, a cheek region A, or a jaw region B) analyzed for skin tones may be displayed in an image. For example, since each face region is displayed in a different color depending on the skin conditions, the user may determine the skin conditions of the face region based on the displayed skin color.

In the analysis result region 3520, a graph 3521 obtained by comparing the result of analyzing the uniformity of skin tones with an average score for each of the brow region L, the cheek region A or the jaw region B, or a score 3522 for the uniformity of pores in the entire face region may be displayed.

According to various embodiments of the present disclosure, if the user selects the score 3522, the analysis result region 3520 may provide the analysis results for the change in skin tones for the entire face region. For example, the analysis result region 3520 may include a graph 3523 obtained by comparing the tone state (or the uniformity state of tone) measured one month ago with the currently measured tone state for each face region (e.g., the brow region L, the cheek region A or the jaw region B), or a graph 3524 indicating how much the tone state of each face region has been improved than before.

Figure 36:
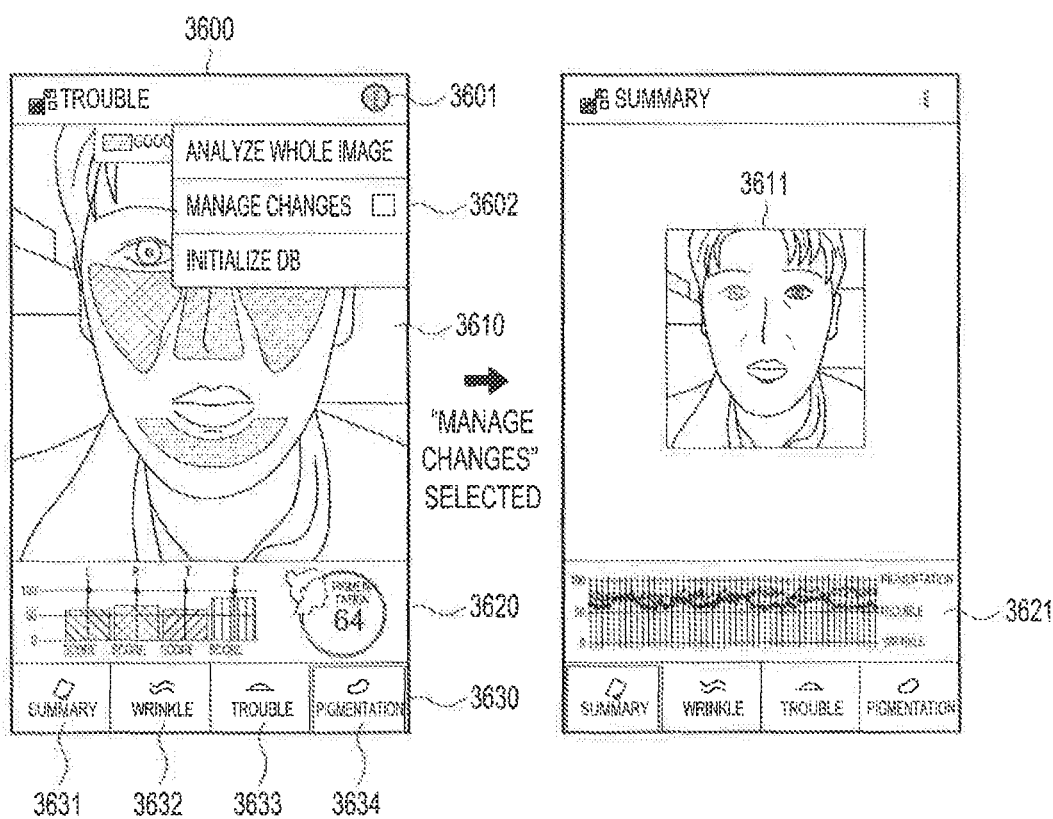
FIG. 36 illustrates an application screen showing a history of face information analyzed based on a stored image according to various embodiments of the present disclosure.

FIG. 36 illustrates an application screen showing a history of face information analyzed based on a stored image according to various embodiments of the present disclosure.

Referring to FIG. 36, if an analysis result screen 3600 including the result of analyzing face information using an application for analyzing face information is displayed, a menu 3601 including a function related to the analyzed face information may be displayed. For example, if the menu 3601 is selected, selection items may be displayed, by which the user can select an Analyze Whole Image function of analyzing at least one selected image on a trial basis, a Manage Changes function 3602 of displaying the history of the analyzed face information, or an Initialize DB function of initializing the data in the previously analyzed face information. Various other functions related to the analysis of face information may be included in the menu 3601.

According to various embodiments of the present disclosure, if the user selects the Manage Changes function 3602, a change in the previously analyzed face information may be displayed in an image region 3610 or an analysis result region 3620 of the analysis result screen 3600. For example, the analysis result region 3620 may display the result of the face analysis for each analysis item using a graph 3621 for a time period in which the face information is analyzed. In the image region 3610, an image may be displayed that is obtained by analyzing the face information at a specific time when the user input is made in the graph 3621. A display section of analysis items 3630 may display analysis items, such as Summary 3631, Wrinkle 3632, Trouble 3633, and Pigmentation 3634.

Figure 37:
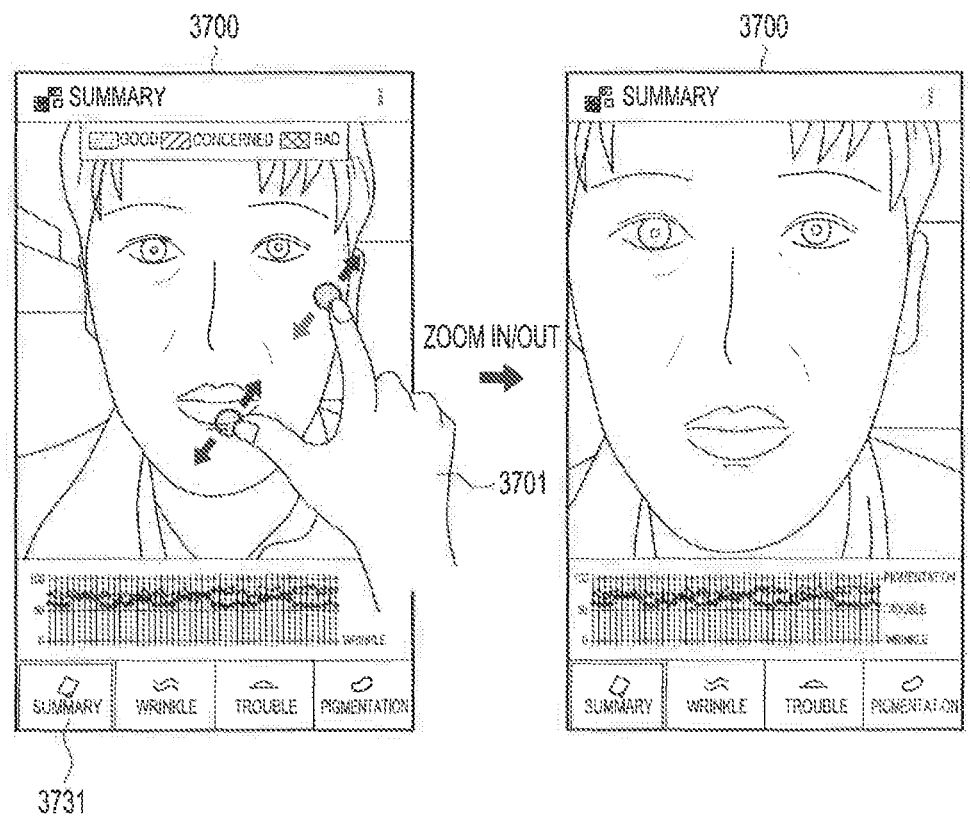
FIGS. 37, 38, 39, 40, 41, 42, 43, 44, and 45 illustrate a screen showing the history of analyzed face information according to various embodiments of the present disclosure.

FIG. 37 illustrates a screen showing a history of analyzed face information according to various embodiments of the present disclosure.

Referring to FIG. 37, the user may select an analysis item or an image region where the user desires to determine a change in the analysis result, on an analysis result screen 3700. For example, in order to determine a change in the analysis result of the pigmentation, the user may select a button of Summary among analysis items (e.g., Summary, Wrinkle, Trouble, or Pigmentation).

According to various embodiments of the present disclosure, the user may make a user input (e.g., pinch in/out, or tap-and-drag) 3701 to zoom in/out an image displayed in the image region, or may move the image to set an image region where the user desires to determine a change in the analysis result.

According to various embodiments of the present disclosure, the analysis result screen 3700 may display the set image region, and display a change in the result of analyzing the displayed image region according to at least one analysis item (e.g., pigmentation, troubles or wrinkles), using a graph. For example, the graph shows the time in which the face information is analyzed, and the analysis results corresponding to the time. If a user input is made as a specific time, an image whose face information is analyzed at the time may be displayed.

Figure 38:
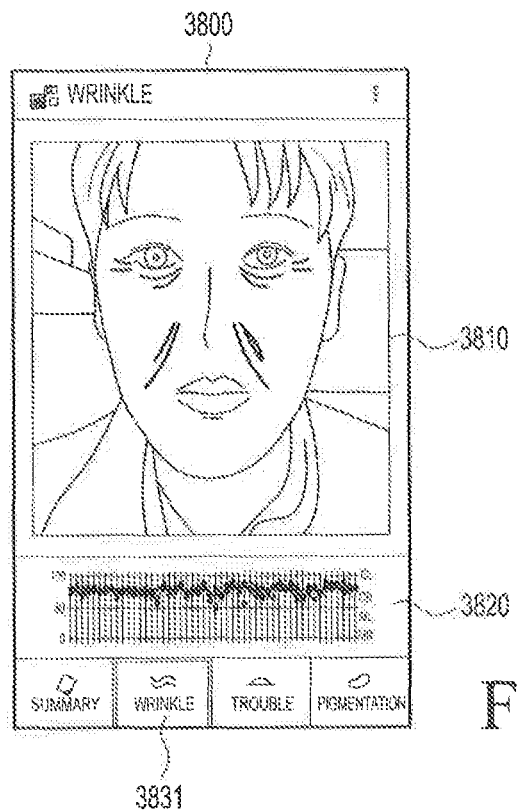

FIG. 38 illustrates a screen showing a history of analyzed face information according to various embodiments of the present disclosure.

Referring to FIG. 38, an analysis result screen 3800 may include an image region 3810 or an analysis result region 3820.

According to various embodiments of the present disclosure, in order to determine a change in the analysis result of the wrinkles, the user may select Wrinkle 3831 among analysis items (e.g., Summary, Wrinkle, Trouble, or Pigmentation).

In the image region 3810, the result of analyzing the wrinkles in the face region of the image may be displayed. For example, the result of analyzing the wrinkles may be displayed in the form of a line, and the depth or length of the wrinkles may be represented depending on the thickness or length of the line.

The analysis result region 3820 may represent the previously analyzed time-based wrinkle state for each face region (e.g., the right region CR or left region CL of the C zone, or the right region MR or left region ML of the M zone) as the result of analyzing the wrinkles, using a graph.

According to various embodiments of the present disclosure, if the user makes a user input (e.g., tap or swipe) as a specific time on the graph, an image used to analyze wrinkles at the time may be displayed in the image region 3810, and the result of analyzing the wrinkles at the time may be displayed on the displayed image.

Figure 39:
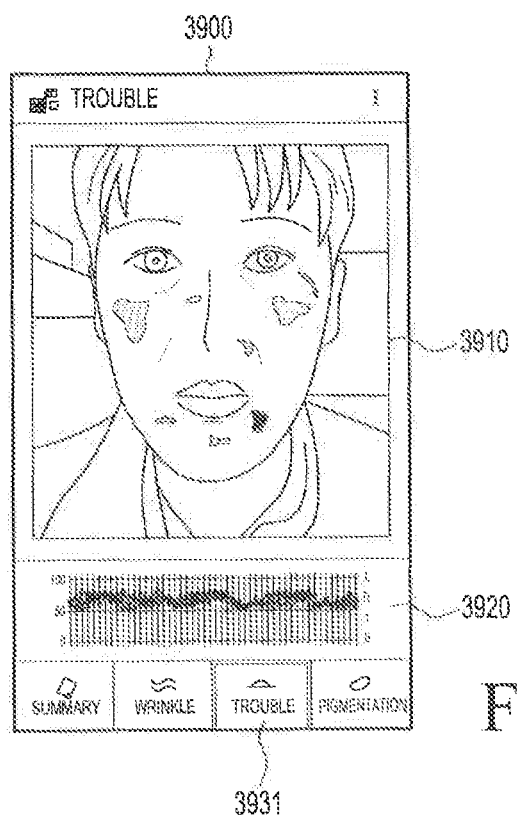

FIG. 39 illustrates a screen showing a history of analyzed face information according to various embodiments of the present disclosure.

Referring to FIG. 39, an analysis result screen 3900 may include an image region 3910 or an analysis result region 3920.

According to various embodiments of the present disclosure, in order to determine a change in the analysis result of the troubles, the user may select Trouble 3931 among analysis items (e.g., Summary, Wrinkle, Trouble, or Pigmentation).

In the image region 3910, the result of analyzing the troubles in the face region of the image may be displayed. For example, the result of analyzing the troubles may be displayed in the form corresponding to the troubles, and the size or state of the troubles may be represented depending on the size or color of the troubles.

The analysis result region 3920 may represent the previously analyzed time-based trouble state for each face region (e.g., the right region R, the left region L, the top region T or the bottom region B) as the result of analyzing the troubles, using a graph.

According to various embodiments of the present disclosure, if the user makes a user input (e.g., tap or swipe) as a specific time on the graph, an image used to analyze troubles at the time may be displayed in the image region 3910, and the result of analyzing the troubles at the time may be displayed on the displayed image.

Figure 40:
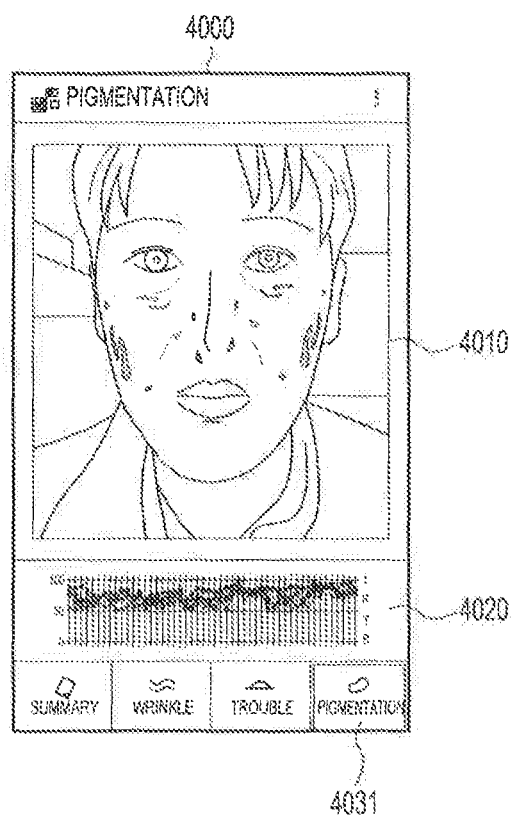

FIG. 40 illustrates a screen showing a history of analyzed face information according to various embodiments of the present disclosure.

Referring to FIG. 40, an analysis result screen 4000 may include an image region 4010 or an analysis result region 4020.

According to various embodiments of the present disclosure, in order to determine a change in the analysis result of the pigmentation, the user may select Pigmentation 4031 among analysis items (e.g., Summary, Wrinkle, Trouble, or Pigmentation).

In the image region 4010, the result of analyzing the pigmentation in the face region of the image may be displayed. For example, the result of analyzing the pigmentation may be displayed in the form corresponding to the pigmentation, and the size or state of the pigmentation may be represented depending on the size or color of the pigmentation.

The analysis result region 4020 may represent the previously analyzed time-based pigmentation state for each face region (e.g., the right region R, the left region L, the top region T or the bottom region B) as the result of analyzing the pigmentation, using a graph.

According to various embodiments of the present disclosure, if the user makes a user input (e.g., tap or swipe) as a specific time on the graph, an image used to analyze pigmentation at the time may be displayed in the image region 4010, and the result of analyzing the pigmentation at the time may be displayed on the displayed image.

Figure 41:
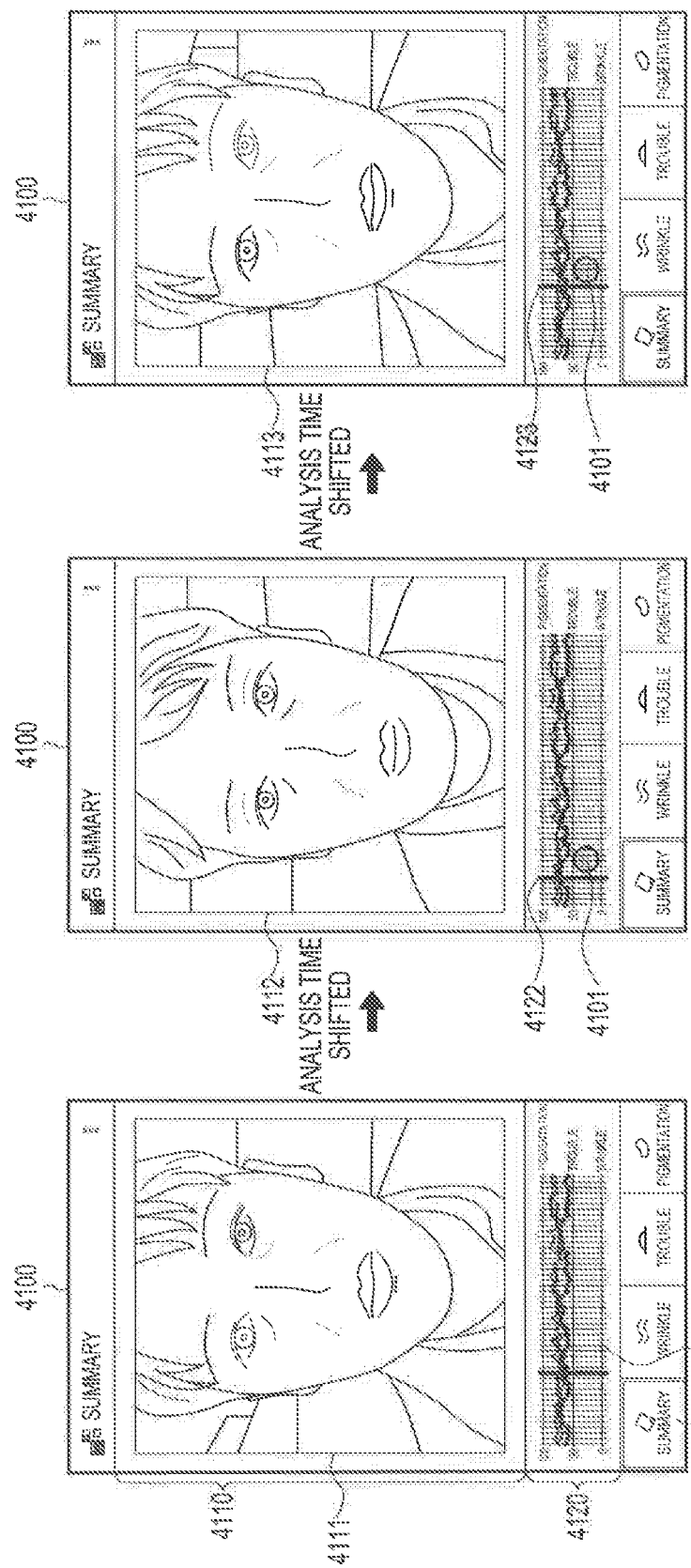

FIG. 41 illustrates a screen showing a history of analyzed face information according to various embodiments of the present disclosure.

Referring to FIG. 41, if a Manage Changes function (e.g., 3602) is selected in a menu (e.g., 3601) of an application for analyzing face information, an analysis result screen 4100 may display the history of the analysis results for various analysis items.

According to various embodiments of the present disclosure, the analysis result screen 4100 may include an image region 4110 including an image obtained by analyzing face information at a specific time for a selected analysis item, or an analysis result region 4120 including a graph representing the previously analysis results as a score of the skin conditions at the time each analysis item (e.g., pigmentation, troubles or wrinkles) is analyzed.

According to various embodiments of the present disclosure, if the user selects Summary 4131 among analysis items (e.g., Summary, Wrinkle, Trouble, or Pigmentation), an image 4111 analyzed at a first time 4121 among the images whose face information is analyzed may be displayed in the image region 4110. The result of analyzing face information for the image 4111 may be displayed in the analysis result region 4120, using a graph.

According to various embodiments of the present disclosure, if a user input 4101 is made as a position corresponding to a specific analysis time of the graph, an image analyzed at the time the user input 4101 is made may be displayed in the image region 4110. For example, in the image region 4110, if the user input 4101 is made as a position corresponding to a second time 4122, an image 4112 whose face information is analyzed may be displayed at the second time 4122, and if the user input 4101 is made as a position corresponding to a third time 4123, an image 4113 whose face information is analyzed may be displayed at the third time 4123.

According to various embodiments of the present disclosure, the displayed images 4111, 4112 or 4113 are used to analyze face information at the time (e.g., the first time 4121, the second time 4122 or the third time 4123) the user input 4101 is made. Since the result of analyzing each analysis item at the time is displayed overlapping with the displayed image, the user may determine the skin conditions for the analysis item.

Figure 42:
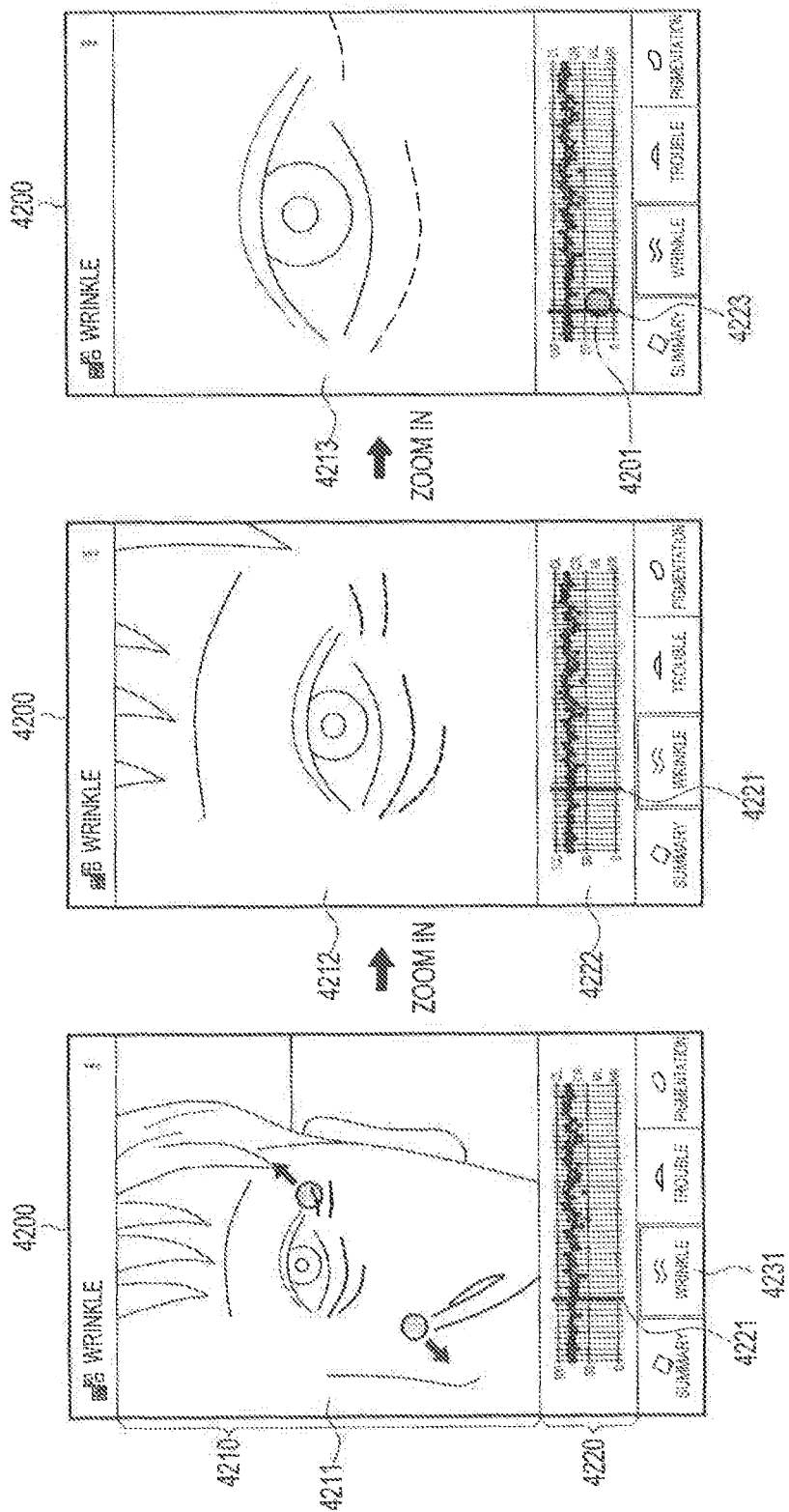

FIG. 42 illustrates a screen showing a history of analyzed face information according to various embodiments of the present disclosure.

Referring to FIG. 42, if a Manage Changes function (e.g., 3602) is selected in a menu (e.g., 3601) of an application for analyzing face information, the history of the analysis results for an analysis item (e.g., Wrinkle 4231) may be displayed on an analysis result screen 4200. For example, the analysis result screen 4200 may include an image region 4210 or an analysis result region 4220.

According to various embodiments of the present disclosure, an image displayed in the image region 4210 is an image 4211 whose face information is analyzed at a first time 4221, and the image 4211 may be changed in size (e.g., zoomed in) in response to a user input (e.g., pinch in/out). For example, based on the resized image, the user may determine the skin conditions in the image that was analyzed at a specific time 4223.

According to various embodiments of the present disclosure, in the image region 4210, setting of the image whose size or position is changed in response to a user input may be maintained at other times. For example, if the image is zoomed in as a user input is made on the image 4211, setting of the zoom may be applied even to an image 4212 whose face information is analyzed at a second time 4222. The image 4212 whose face information is analyzed at the second time 4222 may be displayed to correspond to a region where the image was zoomed in previously. According to various embodiments of the present disclosure, if a user input 4201 is made as a position corresponding to a specific analysis time of the graph, an image analyzed at the time the user input 4201 is made may be displayed in the image region 4110. For example, an image 4213 whose face information is analyzed at a third 4223 may be displayed to correspond to a region where the image 4212 was zoomed in previously.

Figure 43:
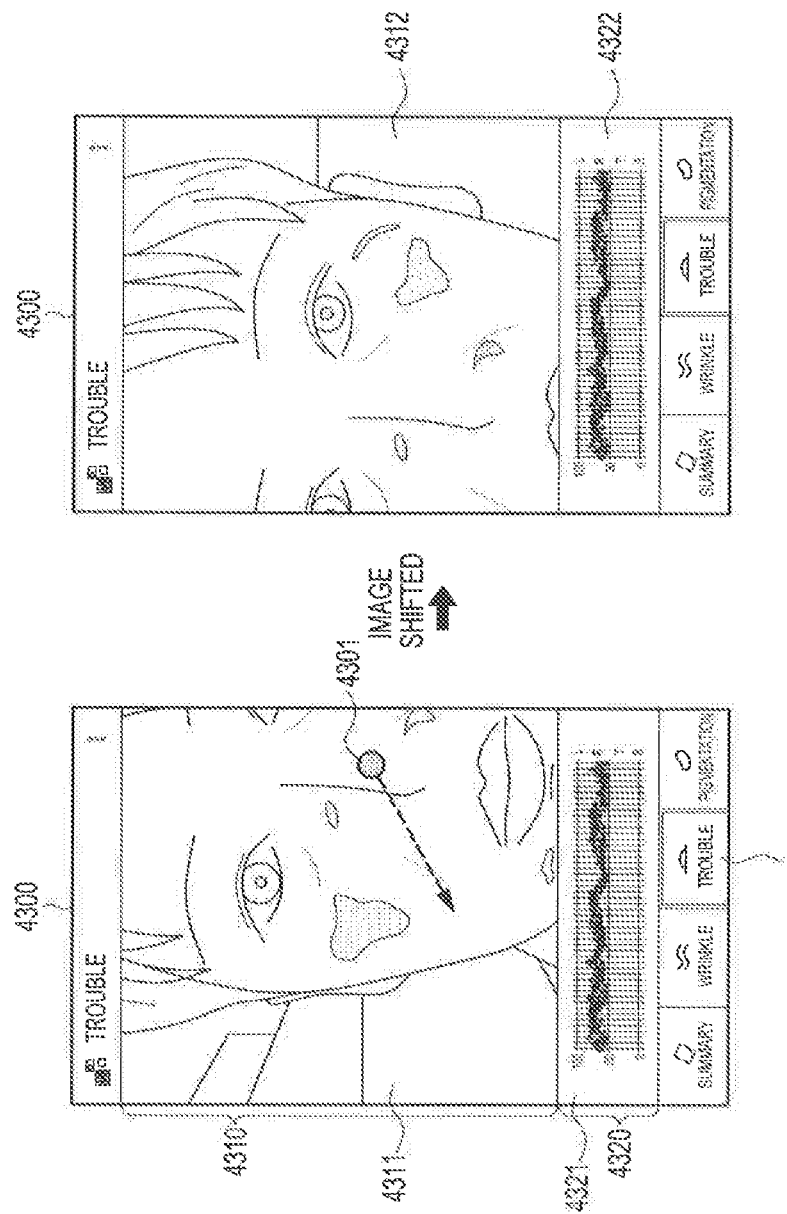

FIG. 43 illustrates a screen showing a history of analyzed face information according to various embodiments of the present disclosure.

Referring to FIG. 43, if one of various analysis items is selected, an analysis result screen 4300 may display the analysis results of the selected analysis item in an image region 4310 or an analysis result region 4320.

According to various embodiments of the present disclosure, if the user selects Trouble 4331 among analysis items (e.g., Summary, Wrinkle, Trouble, or Pigmentation), an image 4311 whose face information is analyzed for troubles may be displayed in the image region 4310. The result of analyzing the troubles for the image 4311 may be displayed in the analysis result region 4320, using a graph 4321.

According to various embodiments of the present disclosure, the displayed image 4311 is an image used to analyze face information at the time a user input is made. Since shapes corresponding to the analyzed troubles are displayed overlapping with the displayed image, the user may determine the position or conditions of the troubles.

According to various embodiments of the present disclosure, by making a user input (e.g., tap-and-drag) 4301, the user may move the region that he/she desires to determine in the image, to the image region 4310. For example, the result of analyzing the troubles in the image region 4312 may be displayed in the analysis result region 4320, using a graph 4322.

According to various embodiments of the present disclosure, as for the image displayed in the image region 4310, setting of the size or position displayed in response to a user input may be maintained, and even if a specific time is selected, the image analyzed at the time may be displayed according to the setting of the changed size or position.

Figure 44:
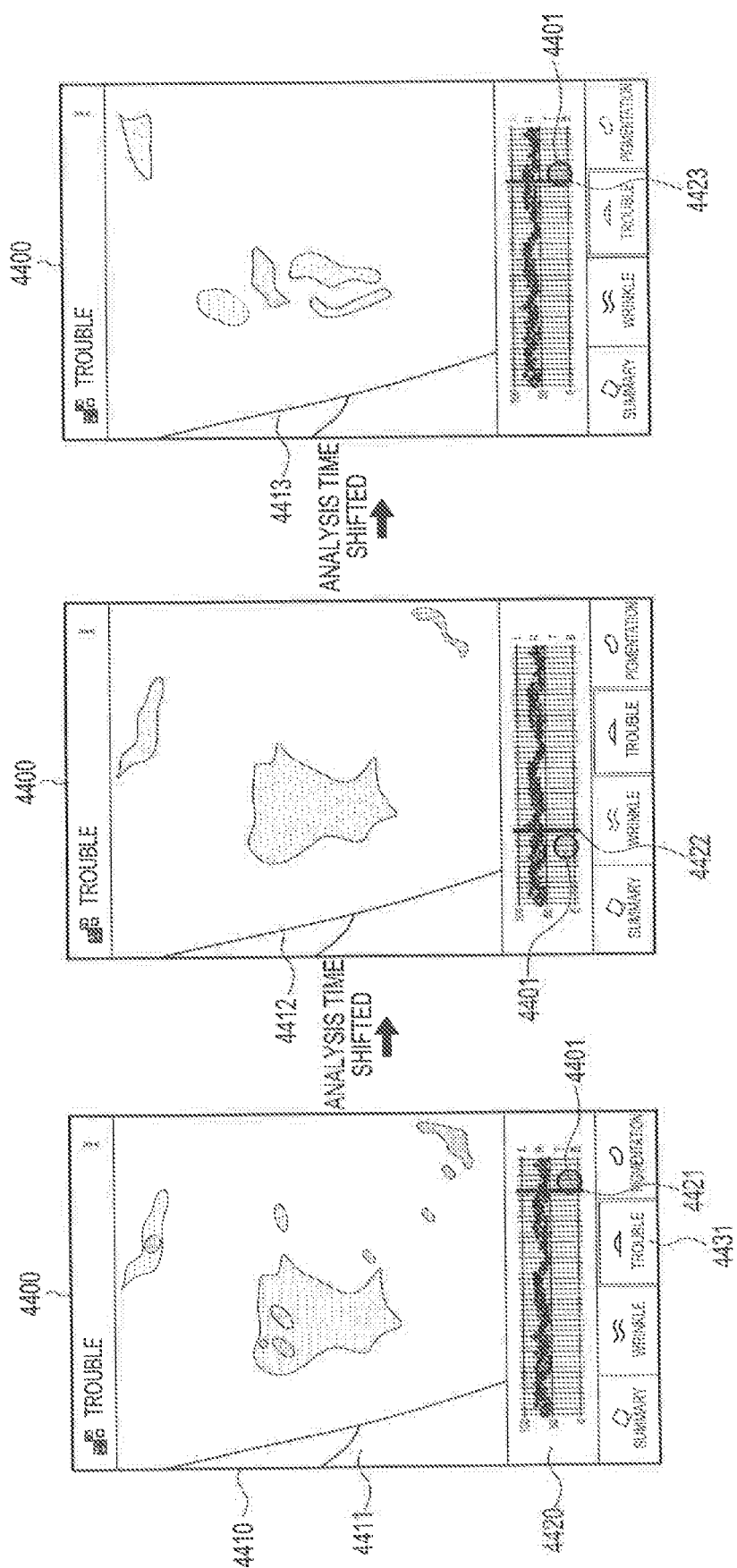

FIG. 44 illustrates a screen showing a history of analyzed face information according to various embodiments of the present disclosure.

Referring to FIG. 44, if one (e.g., Trouble 4431) of various analysis items is selected, an analysis result screen 4400 may display the history of face information for the selected analysis item in an image region 4410 or an analysis result region 4420.

According to various embodiments of the present disclosure, the image region 4410 may be moved or zoomed in a specific image, and the position where the image region 4410 is moved or zoomed in may be maintained, even when an image analyzed at another time is displayed. For example, the user may make a user input (e.g., a touch gesture) in the image region 4410, to move the image region 4410 to the region that the user desires to determine, or to zoom in the region to which the image region 4410 is moved.

According to various embodiments of the present disclosure, the user may select Trouble 4431 among analysis items, and position or zoom in the position of the image region 4410 in the left cheek region. In the image region 4410, the image analyzed at the earliest time among the images analyzed for Trouble 4431 may be displayed.

According to various embodiments of the present disclosure, as the user makes a user input 4401 as a first time 4421, a first image 4411 analyzed at the first image 4421 may be displayed in the image region 4410. For example, in response to the action that the user has moved or zoomed in the image region 4410, the corresponding region in the position where the image region 4410 is moved or zoomed in, in the first image 4411 may be displayed.

According to various embodiments of the present disclosure, if the user input 4401 is made as a second time 4422, a second image 4412 analyzed at the second time 4422 may be displayed in the image region 4410. For example, in response to the action that the user has moved or zoomed in the image region 4410, the corresponding region in the position where the image region 4410 is moved or zoomed in, in the second image 4412 may be displayed.

According to various embodiments of the present disclosure, if the user input 4401 is made as a third time 4423, a third image 4413 analyzed at the third time 4423 may be displayed in the image region 4410. For example, in response to the action that the user has moved or zoomed in the image region 4410, the corresponding region in the position where the image region 4410 is moved or zoomed in, in the third image 4413 may be displayed.

Figure 45:
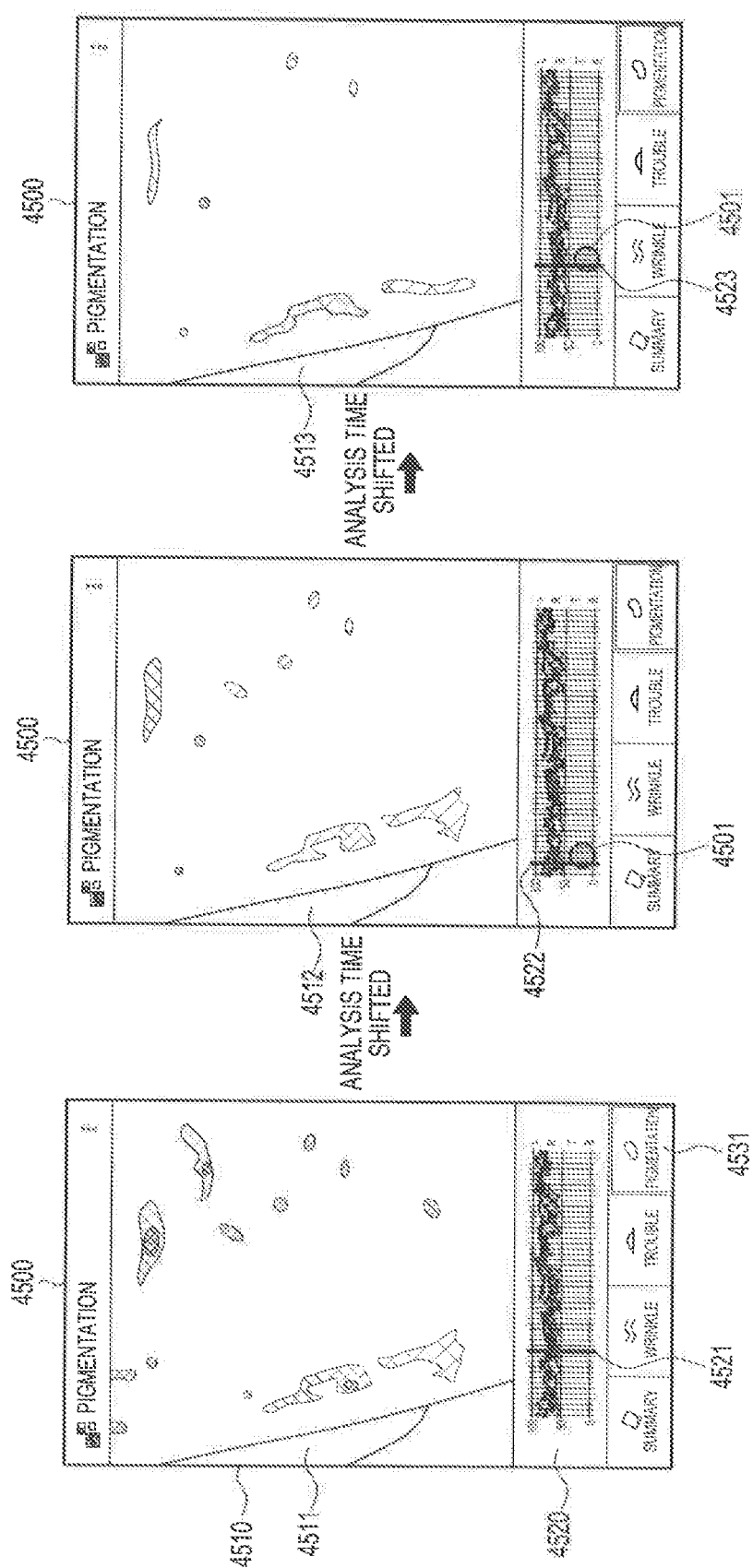

FIG. 45 illustrates a screen showing a history of analyzed face information according to various embodiments of the present disclosure.

Referring to FIG. 45, if one (e.g., Pigmentation 4531) of various analysis items is selected, an analysis result screen 4500 may display the history of face information for the selected analysis item in an image region 4510 or an analysis result region 4520.

According to various embodiments of the present disclosure, the image region 4510 may be moved or zoomed in a specific image, and the position where the image region 4510 is moved or zoomed in may be maintained, even when an image analyzed at another time is displayed. For example, the user may make a user input (e.g., a touch gesture) in the image region 4510, to move the image region 4510 to the region that the user desires to determine, or to zoom in the region to which the image region 4510 is moved.

According to various embodiments of the present disclosure, the user may select Pigmentation 4531 among analysis items, and position or zoom in the position of the image region 4510 in the left cheek region. In the image region 4510, the image analyzed at the earliest time among the images analyzed for Pigmentation 4531 may be displayed.

According to various embodiments of the present disclosure, as the user makes a user input 4501 as a first time 4521, a first image 4511 analyzed at the first image 4521 may be displayed in the image region 4510. For example, in response to the action that the user has moved or zoomed in the image region 4510, the corresponding region in the position where the image region 4510 is moved or zoomed in, in the first image 4511 may be displayed.

According to various embodiments of the present disclosure, if the user input 4501 is made as a second time 4522, a second image 4512 analyzed at the second time 4522 may be displayed in the image region 4510. For example, in response to the action that the user has moved or zoomed in the image region 4510, the corresponding region in the position where the image region 4510 is moved or zoomed in, in the second image 4512 may be displayed.

According to various embodiments of the present disclosure, if the user input 4501 is made as a third time 4523, a third image 4513 analyzed at the third time 4523 may be displayed in the image region 4510. For example, in response to the action that the user has moved or zoomed in the image region 4510, the corresponding region in the position where the image region 4510 is moved or zoomed in, in the third image 4513 may be displayed.

Figure 46:
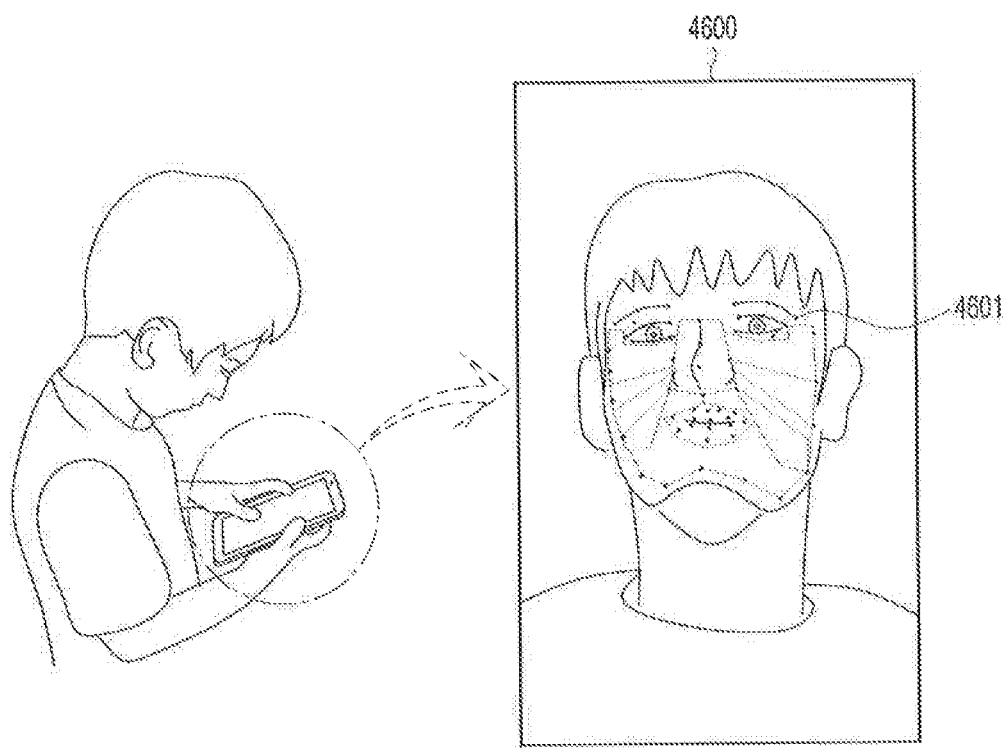
FIG. 46 illustrates a shooting operation for a face analysis according to various embodiments of the present disclosure.

FIG. 46 illustrates a shooting operation for a face analysis according to various embodiments of the present disclosure.

Referring to FIG. 46, an electronic device may obtain the user's face image by enabling the camera module mounted on the front of the electronic device. For example, the electronic device may obtain the image at regular intervals in various situations, such as a case where the user's face is captured at a specific angle, or a case where the electronic device is tilted at a specific angle.

According to various embodiments of the present disclosure, while the user is watching the web browser screen using the electronic device, the electronic device may run the camera module in the background, making it possible to capture a user's face image 4600 regardless of the web browser screen.

According to various embodiments of the present disclosure, the electronic device may determine at least one reference point 4601 in the captured face image 4600 and identify a face region using the reference point, thereby to analyze face information.

Figure 47A:
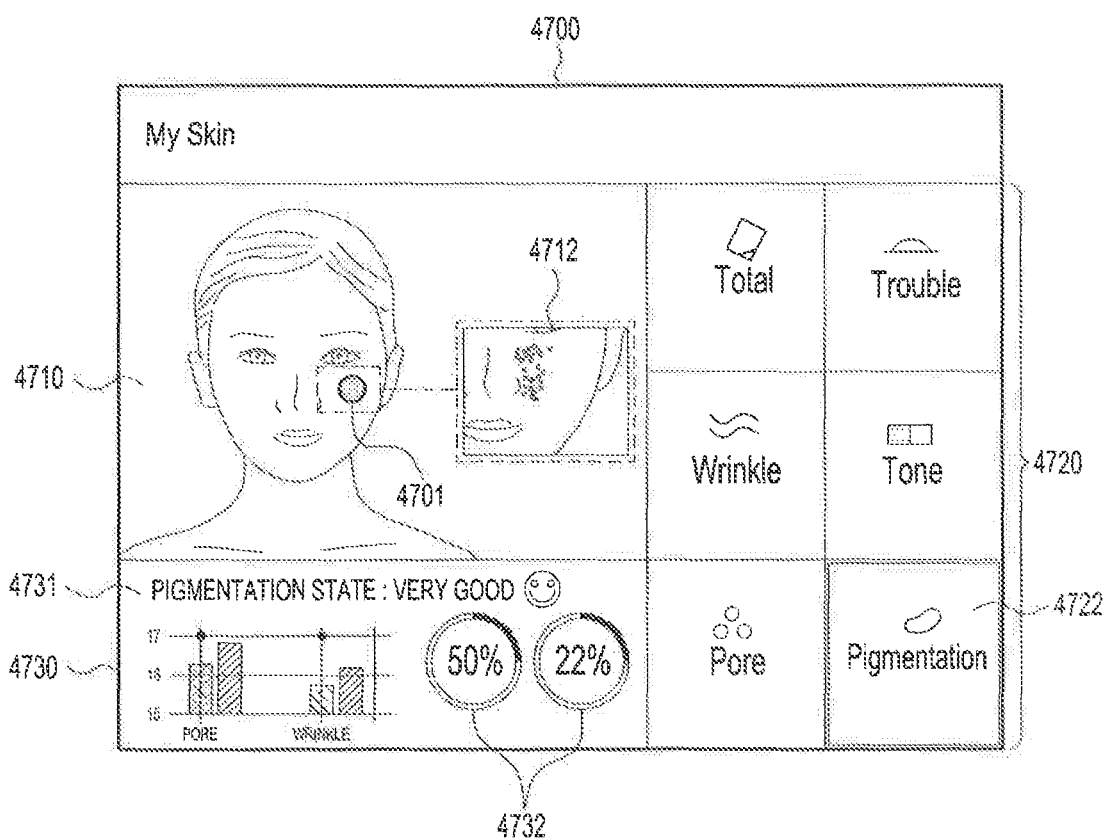
FIGS. 47A and 47B illustrate a screen showing results of skin analysis according to various embodiments of the present disclosure.
Figure 47B:
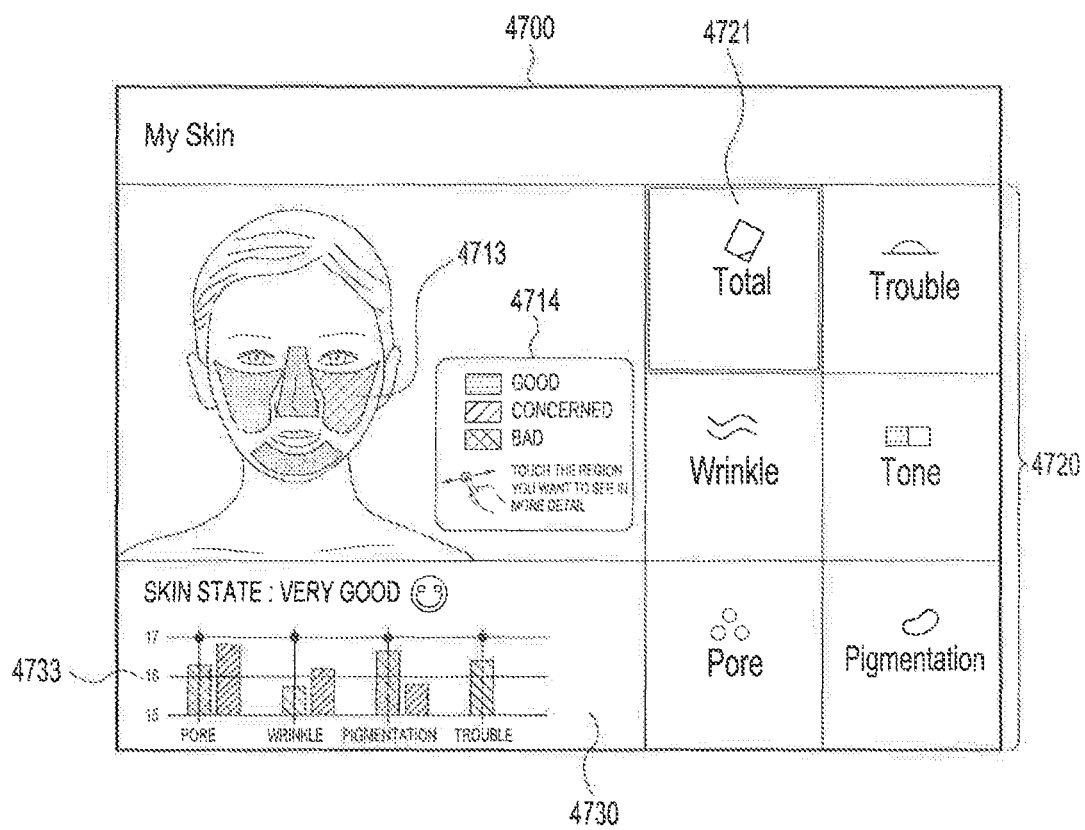

FIGS. 47A and 47B illustrate a screen showing results of a skin analysis according to various embodiments of the present disclosure.

According to various embodiments of the present disclosure, an analysis result screen 4700 may be configured in various layouts depending on the size or rotation direction of the display.

Referring to FIGS. 47A and 47B, if the display is positioned horizontally or the electronic device is a tablet PC, an image region 4710 and an analysis item region 4720 may be horizontally arranged on the analysis result screen 4700.

According to various embodiments of the present disclosure, if the user selects Pigmentation 4722 in the analysis item region 4720, the result of analyzing the pigmentation in at least one face region may be displayed in the image region 4710 or an analysis result region 4730.

In the image region 4710, as a user input 4701 is made in a specific face region (e.g., the cheek region), the analysis result for the face region in which the user input 4701 is made may be zoomed in and displayed in a separate window 4712.

According to various embodiments of the present disclosure, as a specific analysis item is selected in the analysis item region 4720, the analysis result for the face information may be displayed in the analysis result region 4730. For example, the analysis result region 4730 may include an emoticon 4731 indicating the analysis result for the selected pigmentation, a graph showing the score of each item, or an improvement 4732 of the pigmentation compared with before.

According to various embodiments of the present disclosure, if the user selects Total 4721 in the analysis item region 4720, the result of analyzing various analysis items in at least one face region may be displayed in the image region 4710 or the analysis result region 4730.

In the image region 4710, at least one face region 4713 analyzed according to various analysis items may be displayed, and a legend 4714 representing the skin conditions corresponding to the color of each face region may be included. For example, the user may determine the skin conditions of a specific part by determining the color of each face region.

According to various embodiments of the present disclosure, the analysis result region 4730 may include a graph 4733 that represents the score by comparing the analysis results for various analysis items (e.g., pores, wrinkles, pigmentation or troubles) with the previous analysis results.

As is apparent from the foregoing description, an aspect of various embodiments of the present disclosure may provide an electronic device and a method for analyzing face information in the electronic device, in which the user may obtain an image, a part of face information of which is zoomed in or finely captured by the electronic device without any user's action, and may determine the analysis results of the obtained image.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:
1. An electronic device comprising:
a camera;
a display; and
at least one processor configured to:
control the camera to obtain an image,
identify an analysis item among a plurality of analysis items for a skin analysis,
based on the identified analysis item, detect at least one face region among a plurality of face regions of a face in the obtained image, the detected at least one face region being associated with the identified analysis item, analyze a skin condition corresponding to the identified analysis item in the detected at least one face region, and control the display to display a result of analyzing the skin condition corresponding to the identified analysis item.

2. The electronic device of the claim 1, wherein the identified analysis item comprises one of wrinkles, acne, pigmentation, skin tone, dark circles, or pores.

3. The electronic device of the claim 1, wherein the at least one face region comprises at least one of a region around a nose, a region around a mouth, a region around eyes, a region around cheeks, or a region around a forehead.

4. The electronic device of the claim 1,
wherein the processor is further configured to:
control the display to display an object representing analysis times to identify skin analysis history corresponding to the at least one face region,
obtain information related to the skin analysis history corresponding to a selected time among the analysis times, and
control the display to display the information related to the skin analysis history, and
wherein the information related to the skin analysis history corresponds to a skin condition corresponding to the identified analysis item analyzed at the selected time.

5. The electronic device of the claim 1, wherein the processor is further configured to:
enlarge the at least one face region, and
control the display to display the result of analyzing the skin condition on the enlarged at least one face region.

6. The electronic device of the claim 1,
wherein the processor is further configured to control the display to display at least one object corresponding to the result of analyzing the skin condition, and
wherein the at least one object corresponding to the result of analyzing the skin condition includes at least one of a graph or a score corresponding to the skin condition.

7. The electronic device of claim 1, wherein the processor is further configured to:
when a case where the electronic device is positioned at a predetermined angle, or when a case where a predetermined user input is made, control the camera to capture another image.

8. A method for analyzing face information in an electronic device, the method comprising:
controlling a camera of the electronic device to obtain an image;
identifying an analysis item among a plurality of analysis items for a skin analysis;
based on the identified analysis item, detecting at least one face region among a plurality of face regions of a face in the obtained image, the detected at least one face region being associated with the identified analysis item;
analyzing a skin condition corresponding to the identified analysis item in the detected at least one face region; and
controlling a display of the electronic device to display a result of analyzing the skin condition corresponding to the identified analysis item.

9. The method of claim 8, wherein the identified analysis item comprises one of wrinkles, acne, pigmentation, skin tone, dark circles, or pores.

10. The method of claim 8, wherein the at least one face region comprises at least one of a region around a nose, a region around a mouth, a region around eyes, a region around cheeks, or a region around a forehead.

11. The method of claim 8, further comprising:
controlling the display to display an object representing analysis times to identify skin analysis history corresponding to the at least one face region;
obtaining information related to the skin analysis history corresponding to a selected time among the analysis times; and
controlling the display to display the information related to the skin analysis history,
wherein the information related to the skin analysis history corresponds to a skin condition corresponding to the identified analysis item analyzed at the selected time.

12. The method of claim 8, further comprising:
enlarging the at least one face region; and
controlling the display to display the result of analyzing the skin condition on the enlarged at least one face region.

13. The method of claim 8, further comprising:
controlling the display to display at least one object corresponding to the result of analyzing the skin condition,
wherein the at least one object corresponding to the result of analyzing the skin condition includes at least one of a graph or a score corresponding to the skin condition.

14. The method of claim 8, further comprising:
when a case where the electronic device is positioned at a predetermined angle, or when a case where a predetermined user input is made, controlling the camera to capture another image.

15. A non-transitory storage medium storing commands that, when executed by at least one processor, cause the at least one processor to perform at least one operation comprising:
controlling a camera of an electronic device to obtain an image;
identifying an analysis item among a plurality of analysis items for a skin analysis;
based on the identified analysis item, detecting at least one face region among a plurality of face regions of a face in the obtained image, the detected at least one face region being associated with the identified analysis item;
analyzing a skin condition corresponding to the identified analysis item in the detected at least one face region; and
controlling a display of the electronic device to display a result of analyzing the skin condition corresponding to the identified analysis item.

* * * * *